(12) United States Patent
Jacobson et al.

(10) Patent No.: US 7,825,126 B2
(45) Date of Patent: Nov. 2, 2010

(54) PURINE DERIVATIVES AS A3 AND A1 ADENOSINE RECEPTOR AGONISTS

(75) Inventors: Kenneth A. Jacobson, Silver Spring, MD (US); Bhalchandra V. Joshi, Rockville, MD (US); Susanna Tchilibon, Jerusalem (IL)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 735 days.

(21) Appl. No.: 11/574,779

(22) PCT Filed: Sep. 2, 2005

(86) PCT No.: PCT/US2005/031678

§ 371 (c)(1), (2), (4) Date: Mar. 29, 2007

(87) PCT Pub. No.: WO2006/031505

PCT Pub. Date: Mar. 23, 2006

(65) Prior Publication Data

US 2007/0232626 A1 Oct. 4, 2007

Related U.S. Application Data

(60) Provisional application No. 60/608,823, filed on Sep. 9, 2004.

(51) Int. Cl.
C07D 473/40 (2006.01)
C07D 473/34 (2006.01)
C07D 473/18 (2006.01)
A61K 31/52 (2006.01)
A61K 31/522 (2006.01)
A61P 9/02 (2006.01)
C07D 473/36 (2006.01)
C07D 317/70 (2006.01)
C07D 317/28 (2006.01)

(52) U.S. Cl. .............. 514/263.4; 514/263.22; 514/263.23; 514/263.37; 544/276; 544/277; 544/264; 544/265; 549/433; 549/450; 549/451; 549/454

(58) Field of Classification Search ............ 514/263.22, 514/263.23, 263.37, 263.4; 544/276, 277
See application file for complete search history.

(56) References Cited

U.S. PATENT DOCUMENTS
5,688,774 A 11/1997 Jacobson et al.
(Continued)

FOREIGN PATENT DOCUMENTS
WO WO 01/51490 A1 7/2001

OTHER PUBLICATIONS

Bradford et al., A Rapid and Sensitive Method for the Quantitation of Microgram Quantities of Protein Utilizing the Principle of Protein-Dye Binding, *Anal. Biochem.*, 72, 248-254 (1976).
(Continued)

*Primary Examiner*—Mark L Berch
(74) *Attorney, Agent, or Firm*—Leydig, Voit & Mayer, Ltd.

(57) ABSTRACT

Disclosed are (N)-methanocarba adenine nucleosides of the formula:

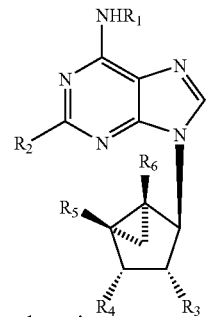

as highly potent $A_3$ adenosine receptor agonists, pharmaceutical compositions comprising such nucleosides, and a method of use of these nucleosides, wherein $R_1$-$R_6$ are as defined in the specification. These nucleosides are contemplated for use in the treatment a number of diseases, for example, inflammation, cardiac ischemia, stroke, asthma, diabetes, and cardiac arrhythmias. The invention also provides compounds that are agonists of both $A_1$ and $A_3$ adenosine receptors for use in cardioprotection.

57 Claims, 8 Drawing Sheets

U.S. PATENT DOCUMENTS

| | | | |
|---|---|---|---|
| 5,773,423 | A | 6/1998 | Jacobson et al. |
| 2003/0092668 | A1* | 5/2003 | Liang et al. ............... 514/46 |
| 2003/0216412 | A1 | 11/2003 | Jacobson et al. |
| 2005/0261237 | A1* | 11/2005 | Boojamra et al. ............... 514/47 |
| 2008/0312180 | A1* | 12/2008 | Liang et al. ............... 514/46 |
| 2009/0192077 | A1* | 7/2009 | Sei et al. ............... 514/8 |

OTHER PUBLICATIONS

Brun et al., Cyclin-dependent kinase (CDK) inhibitors: development of a general strategy for the construction of 2,6,9-trisubstituted purine libraries. Part 1, *Tet. Lett.*, 42, 8161-8164 (2001).

Cohen et al., Enantiospecific Syntheses of Leukotrienes $C_4$, $D_4$, and $E_4$ and [14,15-$^3H_2$] Leukotriene $E_4$ Dimethyl Ester, *J. Amer. Chem. Soc.*, 105, 3661-3672 (1983).

Elzein et al., 2-Pyrazolyl-$N^6$-Substituted Adenosine Derivatives as High Affinity and Selective Adenosine $A_3$ Receptor Agonists, *J. Med. Chem.*, 47, 4766-4773 (2004).

Fishman et al., An agonist to the $A_3$ adenosine receptor inhibits colon carcinoma growth in mice via modulation of GSK-3β and NF-κB, *Oncogene*, 23, 2465-2471 (2004).

Fredholm et al., International Union of Pharmacology. XXV. Nomenclature and Classification of Adenosine Receptors, *Pharmacol. Rev.*, 53, 527-552 (2001).

Gallo-Rodriguez et al., Structure-Activity Relationships of $N^6$-Benzyladenosine-5'—uronamides as $A_3$-Selective Adenosine Agonists, *J. Med. Chem.*, 37, 636-646 (1994).

Gao et al., $N^6$-Substituted adenosine derivatives: selectivity, efficacy, and species differences at $A_3$ adenosine receptors, *Biochem. Pharmacol.*, 65(10), 1675-1684 (2003).

Gao et al., Structural Determinants of $A_3$ Adenosine Receptor Activation: Nucleoside Ligands at the Agonist/Antagonist Boundary, *J. Med. Chem.*, 45, 4471-4484 (2002).

Jacobson et al., Engineering of $A_3$ Adenosine and P2Y Nucleotide Receptors and their Ligands, *Drug. Devel. Res.*, 58, 330-339 (2003).

Joshi et al., New Synthetic Route to (N)Methanocarba Nucleosides Acting as Potent A3 Adenosine Receptors Agonists, $227^{th}$ *ACS National Meeting*, Boston, MA, Abstract MEDI 256 (2004).

Kim et al, 2-Substitution of $N^6$-Benzyladenosine-5'-uronamides Enhances Selectivity for $A_3$ Adenosine Receptors, *J. Med. Chem.*, 37, 3614-3621 (1994).

Kim et al., 2-Substitution of Adenine Nucleotide Analogues Containing a Bicyclo[3.1.0]hexane Ring System Locked in a Northern Conformation: Enhanced Potency as $P2Y_1$ Receptor Antagonists, *J. Med. Chem.*, 46, 4974-4987 (2003).

Lee et al., Ring-Constrained (N)-Methanocarba Nucleosides as Adenosine Receptor Agonists: Independent 5'-Uronamide and 2'-Deoxy Modifications, *Bioorg. Med. Chem. Lett.*, 11, 1333-1337 (2001).

Liu et al., Evidence that the adenosine $A_3$ receptor may mediate the protection afforded by preconditioning in the isolated rabbit heart, *Cardiovasc Res.*, 28, 1057-1061 (1994).

Nordstedt et al., A Modification of a Protein-Binding Method for Rapid Quantification of cAMP in Cell-Culture Supernatants and Body Fluid, *Anal. Biochem.*, 189, 231-234 (1990).

Ohno et al., Modulation of adenosine receptor affinity and intrinsic efficacy in adenine nucleosides substituted at the 2-position, *Bioorg. Med. Chem.*, 12, 2995-3007 (2004).

Ohta et al., Role of G-protein-coupled adenosine receptors in downregulation of inflammation and protection from tissue damage, *Nature*, 414, 916-920 (2001).

Olah et al., $^{125}$I-4-Aminobenzyl-5'-N-methylcarboxamidoadenosine, a High Affinity Radioligand for the Rat $A_3$ Adenosine Receptor, *Mol. Pharmacol.*, 45, 978-982 (1994).

Post et al., Biochemical Methods for Detection and Measurement of Cyclic AMP and Adenylyl Cyclase Activity, *Methods Mol. Biol.*, 126, 363-374 (2000).

Ramkumar et al., The $A_3$ Adenosine Receptor Is the Unique Adenosine Receptor Which Facilitates Release of Allergic Mediators in Mast Cells, *J. Biol. Chem.*, 268, 16887-16890 (1993).

Rao et al., Stereoselective Transformations Leading to Pentono -1, 4-Lactones, *J. Carbohydr. Chem.*, 15, 975-984 (1996).

Ravi et al., Synthesis and Purine Receptor Affinity of 6-Oxopurine Nucleosides and Nucleotides Containing (N)-Methanocarba-pseudoribose Rings, *Bioorganic & Medicinal Chemistry Letters*, 11, 2295-2300 (2001).

Richer et al., Equilibration d'imines cyclaniques, *Can. J. Chem.*, 48(4), 570 (1970).

Strickler et al., Direct Preconditioning of Cultured Chick Ventricular Myocytes, *J. Clin. Invest.*, 98, 1773-1779 (1996).

Tchilibon et al., Exploring distal regions of the $A_3$ adenosine receptor binding site: sterically constrained $N^6$-(2-phenylethyl)adenosine derivatives as potent ligands, *Bioorg. Med. Chem.*, 12, 2021-2034 (2004).

Tchilibon et al., (N)-methanocarba 2,$N^6$-Disubstituted Adenine Nucleosides as Highly Potent and Selective $A_3$ Adenosine Receptor Agonists, *J. Medicinal Chemistry*, 48, 1745-1758 (2005).

Tucker et al., Design and synthesis of a series of potent and orally bioavailable noncovalent thrombin inhibitors that utilize nonbasic groups in the P1 position, *J. Med. Chem.*, 41. 3210-3219 (1998).

Von Lubitz et al., Adenosine $A_3$ receptor stimulation and cerebral ischemia, *Eur. J. Pharmacol.*, 263, 59-67 (1994).

Zwart et al., A functional screening of adenosine analogues at the adenosine $A_{2B}$ receptor: a search for potent agonists, *Nucleosides and Nucleotides*, 17, 969-986 (1998).

\* cited by examiner

US 7,825,126 B2

PURINE DERIVATIVES AS A3 AND A1 ADENOSINE RECEPTOR AGONISTS

CROSS-REFERENCE TO RELATED APPLICATION

This application claims the benefit of U.S. Provisional Patent Application No. 60/608,823, filed Sep. 9, 2004, the disclosure of which is incorporated by reference.

FIELD OF THE INVENTION

This invention pertains to $A_3$ and $A_1$ adenosine receptor agonists, pharmaceutical compositions comprising such agonists, and a method of use thereof, for example, in treating various medical disorders.

BACKGROUND OF THE INVENTION

Extracellular adenosine acts as a local modulator at four subtypes of adenosine receptors, namely, $A_1$, $A_{2A}$, $A_{2B}$, and $A_3$, which are involved in numerous physiological and pathophysiological processes. Fredholm et al., *Pharmacol. Rev.* 2001; 53:527-52. For example, adenosine attenuates the effects of ischemia in the heart and brain. Acting through the $A_{2A}$ adenosine receptor, it suppresses prolonged inflammation; Ohta et al., *Nature* 2001; 414:916-920; and causes vasodilation and inhibits platelet aggregation, thus increasing the amount of oxygen available to an organ under stress. Adenosine agonists selective for the $A_3$ adenosine receptor are of interest as cerebroprotective, cardioprotective, and anticancer agents. von Lubitz et al., *Eur. J. Pharmacol.*, 1994, 263:59-67; Liu et al., *Cardiovasc Res.*, 1994, 28:1057-61; Strickler et al., *J. Clin. Invest.*, 1996, 98:1773-9; Fishman et al., *Oncogene*, 2004, 23:2465-71. It is believed that $A_3$-selective compounds will have utility in the therapeutic and/or prophylactic treatment of cardiac disease, infertility, kidney disease, and central nervous system (CNS) disorders.

The potential utility of $A_1$ and $A_2$-selective agents in therapeutic applications has been limited by accompanying side effects, given the ubiquitous nature of the $A_1$ and $A_2$ receptors. The distribution of the $A_3$ adenosine receptor, by contrast, is fairly limited, being found primarily in the CNS, brain, testes, and immune system, where it appears to be involved in the modulation of release from mast cells of mediators of the immediate hypersensitivity reaction (Ramkumar et al., *J. Biol. Chem.*, 268, 16887-16890 (1993)). The limited distribution of the $A_3$ adenosine receptor provides a basis for predicting that $A_3$-selective compounds may be more useful than $A_1$- and $A_2$-selective compounds as potential therapeutic agents.

Accordingly, there is a great interest for finding $A_3$ adenosine receptor agonists, as shown by the patenting activity in this area; see, for example, U.S. Pat. Nos. 5,773,423 and 5,688,774; and U.S. Published Patent Application No. 2003/0216412 A1. Therefore, there is a great need for $A_3$ adenosine receptor agonists, especially those that are selective to $A_3$ adenosine receptor over the $A_1$ and $A_2$ adenosine receptors. There further exists a need for compounds that activate both $A_3$ and $A_1$ receptors.

The invention provides such adenosine receptor agonists. The advantages of the invention, as well as additional inventive features, will be apparent from the description of the invention provided herein.

BRIEF SUMMARY OF THE INVENTION

The invention provides $A_3$ selective agonists, particularly N-methanocarba adenine nucleosides, for example, with selected substituents at the 2, $N^6$, 2', 3', 4', and 5'-positions, pharmaceutical compositions comprising such nucleosides, and methods of use thereof, for example, in a method for selectively activating an $A_3$ adenosine receptor of a mammal comprising administering to the mammal an effective amount of a nucleoside of the invention.

The invention also provides dual acting $A_3$ and $A_1$ receptor agonists for use in cardioprotection, e.g., in a method of treating patients suffering from ischemic damage or at risk for the same.

DETAILED DESCRIPTION OF THE INVENTION

Figure 1:
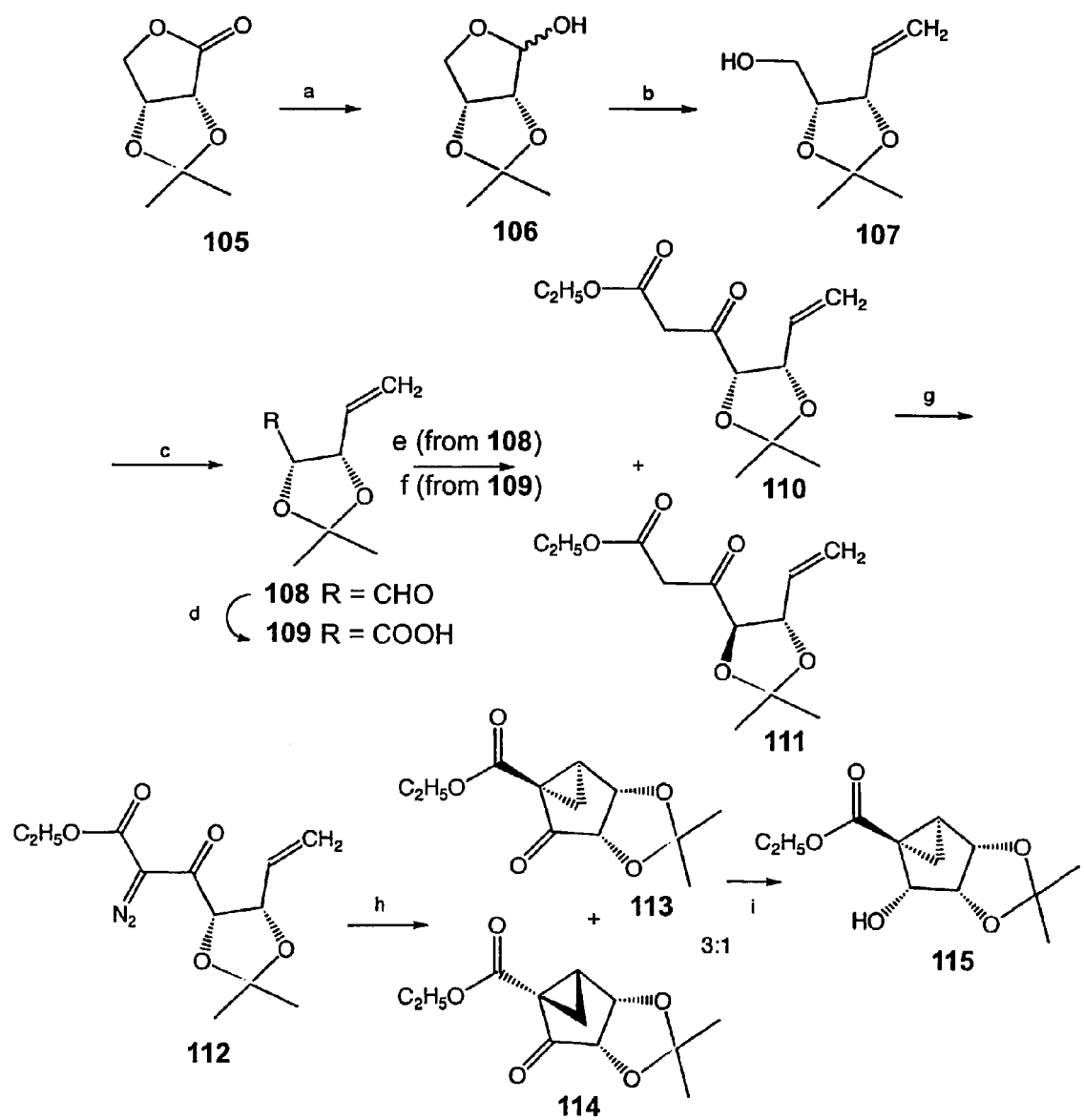
FIG. 1 depicts a reaction scheme for the synthesis of intermediate compound 115 useful for preparing compounds in accordance with an embodiment of the invention. Reagents and conditions: (a) DIBAL-H, $CH_2Cl_2$, $-78°$ C.; (b) methyl-triphenyl-phosphonium bromide, $KOBu^t$, THF, $-78°$ C. to room temperature; (c) DMSO, $(COCl)_2$, $CH_2Cl_2$, $-78°$ C.; (d) NaOCl; (e) $N_2CHCOOEt$, $SnCl_2$, $CH_2Cl_2$, room temperature; (f) 1,1'-carbonyldiimidazole, LDA, $CH_3COOEt$, THF, $-78°$ C.; (g) $TsN_3$, $CH_3CN$, TEA, room temperature; (h) CuI, toluene, reflux; (i) $NaBH_4$, MeOH, room temperature.

The present invention is predicated on the concept that adenine nucleoside analogues having a ring constraint provide enhanced binding affinity and improved selectivity to $A_3$ adenosine receptors. The analogues contain the (N)-methanocarba (bicyclo[3.1.0]hexane) ring system, which is a rigid ribose substitute lacking the ether oxygen.

Accordingly, the present invention provides compounds of the formula:

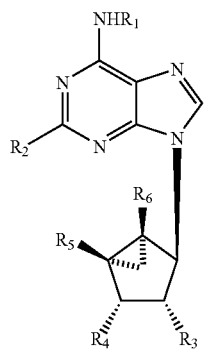

wherein:

$R_1$ is selected from the group consisting of $C_1$-$C_6$ alkyl, $C_1$-$C_6$ alkoxy, hydroxy, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkoxy, heterocyclyl $C_1$-$C_6$ alkyl, heterocyclyl, 4-[[[4-[[[(2-amino $C_1$-$C_6$ alkyl)amino]-carbonyl]-$C_1$-$C_6$ alkyl]aniline]carbonyl]$C_1$-$C_6$ alkyl]$C_6$-$C_{14}$ aryl, and $C_6$-$C_{14}$ aryl $C_3$-$C_8$ cycloalkyl, wherein the aryl or heterocyclyl portion of $R_1$ is optionally substituted with one or more substituents selected from the group consisting of halo, amino, $C_1$-$C_6$ alkyl, $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, aminocarbonyl $C_1$-$C_6$ alkoxy, and $C_6$-$C_{14}$ aryl $C_1$-$C_6$ alkoxy, and any combination thereof; and the alkyl or cycloalkyl portion of $R_1$ is optionally substituted with one or more substituents selected from the group consisting of halo, hydroxy, and amino, and any combination thereof;

$R_2$ is selected from the group consisting of hydrogen, halo, amino, $C_1$-$C_6$ alkoxy, $C_1$-$C_6$ alkylthio, $C_2$-$C_6$ alkenyloxy, $C_2$-$C_6$ alkynyloxy, $C_3$-$C_8$ cycloalkyl $C_1$-$C_6$ alkoxy, $C_3$-$C_8$ cycloalkenyloxy, $C_7$-$C_{12}$ bicycloalkyl $C_1$-$C_6$ alkoxy, $C_7$-$C_{12}$ bicycloalkenyl $C_1$-$C_6$ alkoxy, $C_6$-$C_{14}$ aryloxy, $C_6$-$C_{14}$ aryl $C_1$-$C_6$ alkoxy, $C_6$-$C_{14}$ aryl $C_3$-$C_6$ cycloalkoxy, $C_6$-$C_{14}$ aryl $C_1$-$C_6$ alkylamino, $C_6$-$C_{14}$ aryl Cl-$C_6$ alkylthio, $C_1$-$C_6$ alkyl $C_6$-$C_{14}$ aryl $C_1$-$C_6$ alkoxy, $C_1$-$C_6$ alkoxy $C_6$-$C_{14}$ aryl $C_1$-$C_6$ alkoxy, halo $C_6$-$C_{14}$ aryloxy, halo $C_6$-$C_{14}$ aryl $C_1$-$C_6$ alkoxy, $C_6$-$C_{14}$ aryl $C_1$-$C_6$ alkylamino, $C_1$-$C_6$ dialkoxy $C_6$-$C_{14}$ aryl $C_1$-$C_6$ alkoxy, heterocyclyl $C_1$-$C_6$ alkoxy, hydrazinyl, and pyrazolyl, said pyrazolyl being optionally substituted with one or more substituents selected from the group consisting of $C_1$-$C_6$ alkyl, $C_6$-$C_{14}$ aryl $C_1$-$C_6$ alkyl, $C_6$-$C_{14}$ haloaryl $C_1$-$C_6$ alkyl, aminocarbonyl, $C_1$-$C_6$ alkyl aminocarbonyl, $C_1$-$C_6$ alkoxyphenyl, $C_6$-$C_{14}$ haloaryl, and heterocyclyl, and any combination thereof;

$R_3$ and $R_4$ are independently selected from the group consisting of hydroxy, amino, thiol, ureido, $C_1$-$C_6$ alkyl carbonylamino, hydroxy $C_1$-$C_6$ alkyl, and hydrazinyl;

$R_5$ is selected from the group consisting of $C_1$-$C_3$ alkyl aminocarbonyl, $C_1$-$C_3$ alkylthio $C_1$-$C_3$ alkyl, halo $C_1$-$C_3$ alkyl, hydrazinyl, amino $C_1$-$C_3$ alkyl, hydroxy $C_1$-$C_3$ alkyl, $C_3$-$C_6$ cycloalkylamino, hydroxylamino, and $C_2$-$C_3$ alkenyl; and $R_6$ is hydrogen or fluorine;

or a pharmaceutically acceptable salt thereof;

with the provisos that (i) when $R_1$ is methyl, $R_2$ is chloro, $R_3$ and $R_4$ are hydroxyl, and $R_5$ is methylaminocarbonyl, $R_6$ is not hydrogen; (ii) when $R_1$ is 3-iodobenzyl, $R_2$ is hydrogen or chloro, $R_3$ and $R_4$ are hydroxyl, and $R_5$ is methylaminocarbonyl, $R_6$ is not hydrogen; and (iii) when $R_1$ is $C_1$-$C_6$ alkyl, $C_3$-$C_8$ cycloalkyl, $C_1$-$C_6$ alkoxy, $C_6$-$C_{14}$ aryl, $C_6$-$C_{14}$ aryl $C_1$-$C_6$ alkyl, heterocyclyl, or $C_7$-$C_{12}$ bicycloalkyl, $R_2$ is hydrogen or halo, $R_3$ and $R_4$ are hydroxy, and $R_6$ is hydrogen, $R_5$ is not alkylamino carbonyl.

The term "aryl" refers to aromatic moieties such as phenyl, naphthyl, anthracenyl, and biphenyl. The term "heterocyclyl" refers to 3-7 membered rings comprising carbon and one or more heteroatoms such as O, N, and S, and optionally hydrogen; optionally in combination with one or more aromatic rings. Examples of heterocyclyl groups include pyridyl, piperidinyl, piperazinyl, pyrazinyl, pyrolyl, pyronyl, pyronyl, tetrahydropyranyl, tetrahydrothiopyranyl, pyrrolidinyl, furanyl, tetrahydrofuranyl, thiophenyl, tetrahydrothiophenyl, purinyl, pyrimidinyl, thiazolyl, thiazolidinyl, thiazolinyl, oxazolyl, tetrazolyl, tetrazinyl, benzoxazolyl, morpholinyl, thiophorpholinyl, quinolinyl, and isoquinolinyl. The alkyl, alkoxy, alkylamino groups can be linear or branched. When an aryl group is substituted with a substituent, e.g., halo, amino, alkyl, hydroxy, alkoxy, and others, the aromatic ring hydrogen is replaced with the substituent and this can take place in any of the available hydrogens, e.g., 2, 3, 4, 5, and/or 6-position wherein the 1-position is the point of attachment of the aryl group to the compound of the present invention. The term "halo" refers to fluorine, chlorine, bromine, and iodine. Examples of bicycloalkyls include norbornyl, s-endonorbornyl, carbamethylcylopentyl, and bicyclohexyl. An example of a tricycloalkyl is adamantyl.

In an embodiment, $R_1$ is selected from the group consisting of $C_1$-$C_6$ alkyl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_3$-$C_8$ cycloalkyl, and heterocyclyl $C_1$-$C_6$ alkyl, wherein the aryl or heterocyclyl portion of $R_1$ is optionally substituted with one or more substituents selected from the group consisting of halo, amino, $C_1$-$C_6$ alkyl, $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, aminocarbonyl $C_1$-$C_6$ alkoxy, and $C_6$-$C_{14}$ aryl $C_1$-$C_6$ alkoxy, and any combination thereof.

In a further embodiment, $R_1$ is selected from the group consisting of $C_1$-$C_6$ alkyl, phenyl $C_1$-$C_6$ alkyl, diphenyl $C_1$-$C_6$ alkyl, phenyl $C_3$-$C_8$ cycloalkyl, diphenyl $C_3$-$C_8$ cycloalkyl, and heterocyclyl $C_1$-$C_6$ alkyl, wherein the phenyl or heterocyclyl portion of $R_1$ is optionally substituted with one or more substituents selected from the group consisting of halo, amino, $C_1$-$C_6$ alkyl, $C_1$-$C_6$ alkoxy, phenoxy, hydroxy $C_1$-$C_6$ alkyl, hydroxy $C_2$-$C_6$ alkenyl, hydroxy $C_2$-$C_6$ alkynyl, aminocarbonyl $C_1$-$C_6$ alkoxy, and phenyl $C_1$-$C_6$ alkoxy, and any combination thereof. Preferably, $R_1$ is selected from the group consisting of methyl, benzyl, diphenyl ethyl, phenyl cyclopropyl, diphenyl cyclopropyl, and pyridyl methyl, wherein the phenyl or pyridyl portion of $R_1$ is optionally substituted with one or more substituents selected from the group consisting of halo, amino, $C_1$-$C_6$ alkyl, $C_1$-$C_6$ alkoxy, phenoxy, hydroxy $C_1$-$C_6$ alkyl, hydroxy $C_2$-$C_6$ alkenyl, hydroxy $C_2$-$C_6$ alkynyl, aminocarbonyl $C_1$-$C_6$ alkoxy, and phenyl $C_1$-$C_6$ alkoxy, and any combination thereof.

More preferably, $R_1$ is benzyl which is optionally substituted with one or more substituents selected from the group consisting of halo, amino, $C_1$-$C_6$ alkyl, $C_1$-$C_6$ alkoxy, phenoxy, hydroxy $C_1$-$C_6$ alkyl, hydroxy $C_2$-$C_6$ alkenyl, hydroxy $C_2$-$C_6$ alkynyl, aminocarbonyl $C_1$-$C_6$ alkoxy, and phenyl $C_1$-$C_6$ alkoxy, and any combination thereof. In a specific embodiment, $R_1$ is benzyl.

In another embodiment, $R_1$ is methyl. In a further embodiment, $R_1$ is selected from the group consisting of cyclopentyl and 7-norbornyl, which are both $A_1$ and $A_3$ adenosine receptor agonists when $R_2$ is chloro, $R_3$ and $R_4$ are hydroxy, $R_5$ is methylamino carbonyl, and $R_6$ is hydrogen.

A specific example of $R_1$ is benzyl substituted with one or more substituents selected from the group consisting of halo, amino, methyl, methoxy, phenoxy, hydroxymethyl, hydroxypropynyl, aminocarbonyl methoxy, and benzyloxy, and any combination thereof; preferably halo. Specific examples of substituted benzyl groups are 3-iodobenzyl, 3-bromobenzyl, 3-chlorobenzyl, 3-fluorobenzyl, 2,5-dichlorobenzyl, 2-chloro-5-iodobenzyl, 5-chloro-2-methoxybenzyl, 5-chloro-2-(aminocarbonyl methoxy)benzyl, 5-chloro-2-benzyloxybenzyl, 5-iodo-2-methoxybenzyl, 2,5-dimethoxybenzyl, 2-methylbenzyl, 3-(3-hydroxypropynyl)benzyl, 2-chloro-5-(3-hydroxypropynyl)benzyl, 4-aminobenzyl, and 4-amino-3-iodo-benzyl. Other examples of $R_1$ are cyclopentyl, 3-pyridylmethyl, trans-2-phenyl-1-cyclopropyl, and 2,2-diphenylethyl.

In any of the embodiments discussed above, $R_2$ is preferably selected from the group consisting of halo, amino, and $C_1$-$C_6$ alkylthio, and more preferably from the group consisting of chloro, iodo, amino, and methylthio. Where $R_2$ is a pyrazolyl substituted with a heterocyclyl, it is substituted with any heterocyclyl group, for example, one selected from the group consisting of pyridyl, quiloninyl, isoquinolinyl, pyrimidinyl, and benzoxazolyl.

In any of the embodiments discussed above, $R_3$ and $R_4$ are preferably selected from the group consisting of hydroxy, amino, thiol, and ureido, and more preferably $R_3$ and $R_4$ are hydroxy.

In any of the embodiments discussed above, $R_5$ is preferably selected from the group consisting of $C_1$-$C_3$ alkyl aminocarbonyl, $C_1$-$C_3$ alkylthio $C_1$-$C_3$ alkyl, halo $C_1$-$C_3$ alkyl, amino $C_1$-$C_3$ alkyl, hydroxy $C_1$-$C_3$ alkyl, and $C_3$-$C_6$ cycloalkylamino, more preferably from the group consisting of methylamino carbonyl, methylthio methyl, halomethyl, aminomethyl, hydroxymethyl, and cyclopropylamino, and even more preferably $R_5$ is methylamino carbonyl.

In any of the embodiments discussed above, $R_6$ is preferably hydrogen.

Specific examples of the compounds of the invention are compounds wherein $R_1$ is methyl, $R_2$ is amino, $R_3$ and $R_4$ are hydroxy, $R_5$ is methylamino carbonyl, and $R_6$ is hydrogen; $R_1$ is cyclopentyl, $R_2$ is chloro, $R_3$ and $R_4$ are hydroxy, $R_5$ is methylamino carbonyl, and $R_6$ is hydrogen; $R_1$ is 7-norbornyl, $R_2$ is chloro, $R_3$ and $R_4$ are hydroxy, $R_5$ is methylamino carbonyl, and $R_6$ is hydrogen; $R_1$ is, 3-bromobenzyl, $R_2$ is chloro, $R_3$ and $R_4$ are hydroxy, $R_5$ is methylamino carbonyl, and $R_6$ is hydrogen; $R_1$ is 3-chlorobenzyl, $R_2$ is chloro, $R_3$ and $R_4$ are hydroxy, $R_5$ is methylamino carbonyl, and $R_6$ is hydrogen; $R_1$ is 3-fluorobenzyl, $R_2$ is chloro, $R_3$ and $R_4$ are hydroxy, $R_5$ is methylamino carbonyl, and $R_6$ is hydrogen; $R_1$ is 2,5-dichlorobenzyl, $R_2$ is chloro, $R_3$ and $R_4$ are hydroxy, $R_5$ is methylamino carbonyl, and $R_6$ is hydrogen; $R_1$ is 2-chloro-5-iodobenzyl, $R_2$ is chloro, $R_3$ and $R_4$ are hydroxy, $R_5$ is methylamino carbonyl, and $R_6$ is hydrogen; $R_1$ is 5-chloro-2-methoxybenzyl, $R_2$ is chloro, $R_3$ and $R_4$ are hydroxy, $R_5$ is methylamino carbonyl, and $R_6$ is hydrogen; $R_1$ is 5-chloro-2-(aminocarbonyl methoxy)benzyl, $R_2$ is chloro, $R_3$ and $R_4$ are hydroxy, $R_5$ is methylamino carbonyl, and $R_6$ is hydrogen; $R_1$ is 5-chloro-2-benzyloxybenzyl, $R_2$ is chloro, $R_3$ and $R_4$ are hydroxy, $R_5$ is methylamino carbonyl, and $R_6$ is hydrogen; $R_1$ is 5-iodo-2-methoxybenzyl, $R_2$ is chloro, $R_3$ and $R_4$ are hydroxy, $R_5$ is methylamino carbonyl, and $R_6$ is hydrogen; $R_1$ is 2,5-dimethoxybenzyl, $R_2$ is chloro, $R_3$ and $R_4$ are hydroxy, $R_5$ is methylamino carbonyl, and $R_6$ is hydrogen; $R_1$ is 2-methylbenzyl, $R_2$ is chloro, $R_3$ and $R_4$ are hydroxy, $R_5$ is methylamino carbonyl, and $R_6$ is hydrogen; $R_1$ is 3-methylbenzyl, $R_2$ is chloro, $R_3$ and $R_4$ are hydroxy, $R_5$ is methylamino carbonyl, and $R_6$ is hydrogen; $R_1$ is 3-(3-hydroxypropynyl)benzyl, $R_2$ is chloro, $R_3$ and $R_4$ are hydroxy, $R_5$ is methylamino carbonyl, and $R_6$ is hydrogen; $R_1$ is 2-chloro-5-(3-hydroxypropynyl)benzyl, $R_2$ is chloro, $R_3$ and $R_4$ are hydroxy, $R_5$ is methylamino carbonyl, and $R_6$ is hydrogen; $R_1$ is 4-aminobenzyl, $R_2$ is chloro, $R_3$ and $R_4$ are hydroxy, $R_5$ is methylamino carbonyl, and $R_6$ is hydrogen; $R_1$ is 4-amino-3-iodobenzyl, $R_2$ is chloro, $R_3$ and $R_4$ are hydroxy, $R_5$ is methylamino carbonyl, and $R_6$ is hydrogen; $R_1$ is 3-pyridylmethyl, $R_2$-is-chloro, $R_3$ and $R_4$ are hydroxy, $R_5$ is methylamino carbonyl, and $R_6$ is hydrogen; $R_1$ is trans-2-phenyl-1-cyclopropyl, $R_2$ is chloro, $R_3$ and $R_4$ are hydroxy, $R_5$ is methylamino carbonyl, and $R_6$ is hydrogen; $R_1$ is 2,2-diphenylethyl, $R_2$ is chloro, $R_3$ and $R_4$ are hydroxy, $R_5$ is methylamino carbonyl, and $R_6$ is hydrogen; $R_1$ is 3-chlorobenzyl, $R_2$ is iodo, $R_3$ and $R_4$ are hydroxy, $R_5$ is methylamino carbonyl, and $R_6$ is hydrogen; and $R_1$ is 3-chlorobenzyl, $R_2$ is methylthio, $R_3$ and $R_4$ are hydroxy, $R_5$ is methylamino carbonyl, and $R_6$ is hydrogen.

Among the 2-chloro, 5'-N-methylamide substituted compounds of the invention, the $N^6$-(3-chlorobenzyl) and $N^6$-(3-bromobenzyl) analogues displayed $K_i$ values at the human $A_3$ adenosine receptor of 0.29 and 0.38 nM, respectively. Other subnanomolar affinities were observed for the following $N^6$ derivatives: 2,5-dichlorobenzyl, 5-iodo-2-methoxybenzyl, trans-2-phenyl-1-cyclopropyl, and 2,2-diphenylethyl. Selectivity for the human $A_3$ adenosine receptor in comparison to the $A_1$ adenosine receptor was (fold): the $N^6$-(2,2-diphenylethyl) analogue 34 (1900), the $N^6$-(2,5-dimethoxybenzyl) analogue 26 (1200), the $N^6$-(2,5-dichlorobenzyl) and $N^6$-(2-phenyl-1-cyclopropyl) analogues 20 and 33 (1000), and the $N^6$-(3-substituted benzyl) analogues 17, 18, 28, and 29 (700-900). Typically, even greater selectivity ratios were obtained in comparison with the $A_{2A}$ and $A_{2B}$ adenosine receptors. The above (N)-methanocarba-5'-uronamide analogues are full agonists at the $A_3$ adenosine receptor, as indicated by the inhibition of forskolin-stimulated adenylate cyclase at a concentration of 10 μM. The $N^6$-(2,2-diphenylethyl) derivative was, surprisingly an $A_3$ adenosine receptor agonist in the (N)-methanocarba-5'-uronamide series, although it was an antagonist in the ribose series.

The present invention also provides compounds of the formula:

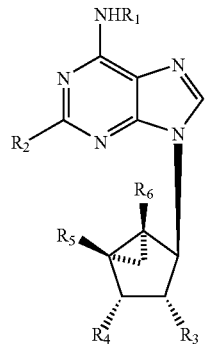

wherein:
(a) $R_1$ is $C_3$-$C_8$ cycloalkyl substituted with aminocarbonylamino;
$R_2$ is selected from the group consisting of hydrogen, halo, $C_1$-$C_6$ alkoxy, $C_1$-$C_6$ alkylthio, $C_1$-$C_6$ alkylamino;
$R_3$ is hydroxy;
$R_4$ is selected from the group consisting of amino, hydroxy, and halo;
$R_5$ is a $C_1$-$C_3$ alkyl aminocarbonyl; and
$R_6$ is hydrogen or halo;
(b) $R_1$ is $C_3$-$C_8$ cycloalkyl, optionally substituted with one or more substituents selected from the group consisting of halo, hydroxy, amino, aminocarbonylamino, and any combination thereof;
$R_2$ is selected from the group consisting of $C_1$-$C_6$ alkoxy and $C_1$-$C_6$ alkylamino;
$R_3$ is hydroxy;
$R_4$ is selected from the group consisting of amino, hydroxy, and halo;
$R_5$ is a $C_1$-$C_3$ alkyl aminocarbonyl; and
$R_6$ is hydrogen or halo;
(c) $R_1$ is $C_3$-$C_8$ cycloalkyl, optionally substituted with one or more substituents selected from the group consisting of halo, hydroxy, amino, aminocarbonylamino, and any combination thereof;
$R_2$ is selected from the group consisting of hydrogen, halo, $C_1$-$C_6$ alkoxy, $C_1$-$C_6$ alkylthio, $C_1$-$C_6$ alkylamino;
$R_3$ is hydroxy;
$R_4$ is halo;
$R_5$ is a $C_1$-$C_3$ alkyl aminocarbonyl; and
$R_6$ is hydrogen or halo; or
(d) $R_1$ is $C_3$-$C_8$ cycloalkyl, optionally substituted with one or more substituents selected from the group consisting of halo, hydroxy, amino, aminocarbonylamino, and any combination thereof;
$R_2$ is selected from the group consisting of $C_1$-$C_6$ alkoxy and $C_1$-$C_6$ alkylamino;
$R_3$ is hydroxy;
$R_4$ is selected from the group consisting of amino, hydroxy, and halo;
$R_5$ is a $C_1$-$C_3$ alkyl aminocarbonyl; and
$R_6$ is halo;
or a pharmaceutically acceptable salt thereof.

In the embodiments, the invention provides compounds wherein $R_1$ is cyclopentyl, optionally substituted with hydroxy, amino, or aminocarbonylamino.

The present invention further provides, in certain embodiments, compounds of the formula:

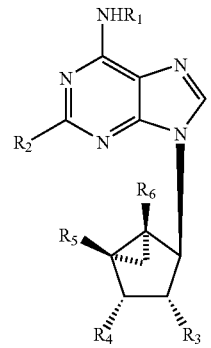

wherein $R_1$ is selected from the group consisting of

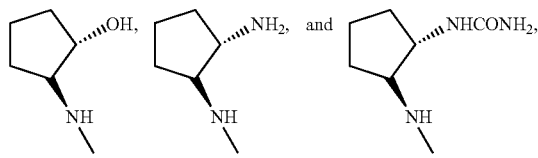

wherein $R_1$ is shown along with the $N^6H$ of the compound;
$R_2$ is selected from the group consisting of hydrogen, halo, $C_1$-$C_6$ alkylthio, $C_1$-$C_6$ alkoxy, and $C_1$-$C_6$ alkylamino;
$R_3$ is hydroxy;
$R_4$ is selected from the group consisting of amino, hydroxy, and halo;
$R_5$ is a $C_1$-$C_3$ alkyl aminocarbonyl; and
$R_6$ is hydrogen or halo; or a pharmaceutically acceptable salt thereof.

In the embodiments, the present invention provides compounds wherein $R_2$ is chloro, $R_3$ and $R_4$ are hydroxy, $R_5$ is methylaminocarbonyl, and $R_6$ is hydrogen.

In some other embodiments, the present invention provides compounds of the formula

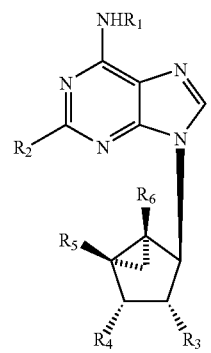

wherein $R_1$ is heterocyclyl;
$R_2$ is selected from the group consisting of hydrogen, halo, $C_1$-$C_6$ alkylthio, $C_1$-$C_6$ alkoxy, and $C_1$-$C_6$ alkylamino;
$R_3$ is hydroxy;
$R_4$ is selected from the group consisting of amino, hydroxy, and halo;

$R_5$ is a $C_1$-$C_3$ alkyl aminocarbonyl; and
$R_6$ is hydrogen or halo; or a pharmaceutically acceptable salt thereof.

In the embodiments, the present invention provides compounds wherein $R_1$ is tetrahydrofuranyl, for example, compounds wherein $R_1$ is

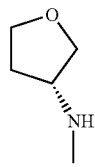

wherein $R_1$ is shown along with $N^6H$. In particular embodiments, the compounds have the following substituents: $R_2$ is chloro, $R_3$ and $R_4$ are hydroxy, $R_5$ is methylaminocarbonyl, and $R_6$ is hydrogen.

Compounds of the invention wherein $R_1$ is cycloalkyl or heterocyclyl act as activators of both $A_1$ and $A_3$ adenosine receptors. Activation of $A_1$ and $A_3$ adenosine receptors could lead to activation of PLC and PLD (phospholipase C and D). PLC and PLD converge on activation of protein kinase C (PKC), which mediates cardioprotection. Agonist of $A_1$ and $A_3$ adenosine receptors show anti-ischemic cardioprotective effect in an intact mouse heart model of global ischemia and reperfusion injury.

The compounds of the present invention can be prepared by any suitable method, for example, the method of Joshi et al., 227th *ACS National Meeting*, August 2002, Boston, Mass., Abstract MEDI 256, which is based on two key steps: (1) intramolecular cyclopropanation reaction performed on an appropriately substituted carbohydrate chiral synthon and (2) a key acid-catalyzed isomerization of an isopropylidene group. See also FIGS. 1-6. The substituents $R_1$-$R_6$ can be introduced or incorporated into the molecule by any suitable method; see, for example, U.S. Pat. Nos. 5,773,423 and 5,688,774 and U.S. Published Application No. 2003/0216412 A1.

Further, *Can. J. Chem.*, 1970, 48, 570 discloses a method to convert a cyclic ketone to aminocycloalkane by transamination, and Hughes, D. L., *Org. Reac.* 1992, 42, 335-656 discloses aspects of the Mitsunobu reaction, which performs a stereospecific conversion of an alcohol to a primary amine with inversion of configuration. The alcohol is treated with triphenylphosphine, diethyl azodicarboxylate and usually, phthalimide, followed by hydrazinolysis. These methods can be used to introduce a 3'-amino group in the compounds of the present invention. Pyrazolyl groups can be introduced into the 2-position of the adenine ring by the methods shown in Elzein et al., *J. Med. Chem.*, 2004, 47, 4766-4773.

The present invention further provides a pharmaceutical composition comprising a compound as described above and a pharmaceutically acceptable carrier. The present invention provides a pharmaceutical composition comprising a pharmaceutically acceptable carrier and an effective amount, e.g., a therapeutically effective amount, including a prophylactically effective amount, of one or more of the aforesaid compounds, or salts thereof, of the present invention.

Examples of pharmaceutically acceptable salts for use in the present inventive pharmaceutical composition include those derived from mineral acids, such as hydrochloric, hydrobromic, phosphoric, metaphosphoric, nitric and sulphuric acids, and organic acids, such as tartaric, acetic, citric, malic, lactic, fumaric, benzoic, glycolic, gluconic, succinic, and arylsulphonic, for example p-toluenesulphonic, acids.

The pharmaceutically acceptable carrier can be any of those conventionally used and is limited only by chemico-physical considerations, such as solubility and lack of reactivity with the compound, and by the route of administration. It will be appreciated by one of skill in the art that, in addition to the following described pharmaceutical compositions, the compounds of the present invention can be formulated as inclusion complexes, such as cyclodextrin inclusion complexes, or liposomes.

The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard-or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing; in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty-acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The present invention provides a method of selectively activating $A_3$ adenosine receptors in a mammal, which method comprises administering to a mammal in need of selective activation of its $A_3$ adenosine receptors a therapeutically effective amount, including a prophylactically effective amount, of a compound which binds with the $A_3$ receptor so as to stimulate an $A_3$ receptor-dependent response. The compound can be administered acutely or chronically.

The method of the present invention has particular usefulness in in vivo applications. For example, $A_3$ adenosine receptor agonists can be used in the treatment of any disease state or condition involving the release of inositol-1,4,5-triphosphate (IP3), diacylglycerol (DAG), and free radicals and subsequent arachidonic acid cascades. Thus, high blood pressure, locomotor hyperactivity, hypertension, acute hypoxia, depression, and infertility can be treated in accordance with the present inventive method, wherein one of the above-described compounds is acutely administered, e.g., within about a few minutes to about an hour of the onset or realization of symptoms. The method also has utility in the treatment of chronic disease states and conditions, in particular those conditions and disease states wherein chronic prophylactic or therapeutic administration of one of the above-described compounds will prevent the onset of symptoms or will reduce recovery time. Examples of disease states and conditions that may be chronically treated in accordance with the present inventive method include inflammatory disorders, such as vascular inflammation and arthritis, allergies, asthma, wound healing, stroke, cardiac failure, acute spinal cord injury, acute head injury or trauma, seizure, neonatal hypoxia (cerebral palsy; prophylactic treatment involves, chronic exposure through placental circulation), chronic hypoxia due to arteriovenous malformations and occlusive cerebral artery disease, severe neurological disorders related to excitotoxicity, Parkinson's disease, Huntington's chorea, and other diseases of the CNS, cardiac disease, kidney disease, and contraception.

These compounds of the invention can be significant cerebral protectants. As such, the above compounds can be used to treat and/or protect against a variety of disorders, including, for example, seizures, transient ischemic shock, strokes, focal ischemia originating from thrombus or cerebral hemorrhage, global ischemia originating from cardiac arrest, trauma, neonatal palsy, hypovolemic shock, and hyperglycemia and associated neuropathies.

The above method of treatment is applicable, for example, where a mammal has or is at risk of having a condition, disorder, or disease state associated with the cellular release of inositol-1,4,5-triphosphate or diacylglycerol. The method is also applicable when the mammal has or is at risk for hyperactivity and the compound in binding to the $A_3$ adenosine receptors functions as a locomotor depressant.

The present inventive method is also applicable when the mammal has or is at risk for hypertension and the compound in binding to the $A_3$ adenosine receptors functions as a hypotensive agent. The method is also applicable when the mammal has or is at risk for anxiety and the compound in binding to the $A_3$ adenosine receptors functions as an anxiolytic agent. The method is furthermore applicable when the mammal has or is at risk for cerebral ischemia and the compound in binding to the $A_3$ adenosine receptors functions as a cerebroprotectant. The method is also applicable when the mammal has or is at risk for seizures and the compound in binding to the $A_3$ adenosine receptors functions as an antiseizure agent.

The present inventive method can be administered chronically as well as acutely. The present inventive method includes the administration to an animal, such as a mammal, particularly a human, in need of the desired $A_3$ receptor-dependent response of an-effective amount, e.g., a therapeutically effective amount, of one or more of the aforementioned present inventive compounds or pharmaceutically acceptable salts or derivatives thereof, alone or in combination with one or more other pharmaceutically active compounds.

In an embodiment, the present invention provides a method for activating $A_3$ and $A_1$ adenosine receptors in a mammal comprising administering to the mammal an effective amount of a compound that has affinity for both the receptors. Accordingly, the present invention provides a method of cardioprotecting a patient in need thereof comprising administering to the patient an agonist having affinity for both the $A_1$ and $A_3$ adenosine receptors in an effective amount of a compound to activate the $A_1$ and $A_3$ adenosine receptors in the heart of said patient. Cardioprotecting comprises preventing or reducing ischemic damage to the heart.

One skilled in the art will appreciate that suitable methods of administering a compound of the present invention to an animal are available, and, although more than one route can be used to administer a particular compound, a particular route can provide a more immediate and more effective reaction than another route. Accordingly, the above-described methods are merely exemplary and are in no way limiting.

The dose administered to an animal, particularly a human, in the context of the present invention should be sufficient to effect a prophylactic or other therapeutic response in the animal over a reasonable time frame. One skilled in the art will recognize that dosage will depend upon a variety of factors including the strength of the particular compound employed, the age, species, condition, and body weight of the animal, as well as the severity/stage of the disease or condition. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states, in particular chronic conditions or disease states, may require prolonged treatment involving multiple administrations.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day if desired. In proper doses and with suitable administration of certain compounds, the present invention provides for a wide range of selective $A_3$ adenosine receptor-dependent responses, as well as $A_3$ and $A_1$ adenosine receptor dependent responses. Exemplary dosages range from about 0.01 to about 100 mg/kg body weight of the animal being treated/day. Preferred dosages range from about 0.1 to about 10 mg/kg body weight/day.

The present invention further provides a method for activating an $A_3$ adenosine receptor, or both $A_3$ and $A_1$ adenosine receptors, in a cell comprising contacting the cell with a compound of the invention. The contacting can take place in vivo or in vitro.

The following examples further illustrate the invention but, of course, should not be construed as in any way limiting its scope.

EXAMPLE 1

This example demonstrates a method of preparing some of the compounds in accordance with embodiments of the invention.

The synthesis shown in FIG. 1 started with commercially available 2,3-O-isopropylidene-D-erythronolactone (105), which was reduced with DIBAL-H to provide 2,3-O-isopropylidene-D-erythrose (106) according to published methods. Gao et al., *J. Amer. Chem. Soc.* 1983, 105, 3661-3672. This lactol underwent Wittig olefination with the corresponding methylenetriphenylphosphine ylid to afford the ring-opened alcohol 107 in 60% yield. At this stage, a Swern oxidation protocol was chosen among several methods tested to oxidize 107 to the corresponding aldehyde 108. The resulting aldehyde was found to be unstable and therefore it was utilized immediately for the next reaction. Oxidation of the aldehyde to the acid 109 with sodium chlorite, followed by Dieckmann condensation of the activated acid with ethyl 2-lithioacetate, afforded the desired β-ketoester 110 (59%) plus an unwanted epimerized derivative 111 (9%) as a mixture of separable diastereoisomers. This epimerization problem was surmounted by treating aldehyde 4a directly with ethyl diazoacetate in the presence of tin (II) chloride to provide the keto ester 110 as the sole product in 36% overall yield from alcohol 107. Using a standard protocol, the unsaturated keto ester 110 was converted to the diazo compound 112, which underwent a thermally-induced intramolecular cyclopropanation to give the bicyclo[3.1.0]hexan-2-one derivatives 113 and 114 in a combined 48% yield with a favorable diastereoisomeric ratio (3:1) for the desired isomer 113. The bicyclo derivative 113 was isolated chromatographically and reduced stereospecifically with $NaBH_4$ to give alcohol 115 as a single product in 72% yield. The structure of 115 was confirmed by X-ray analysis, which unambiguously validated the suitability of our synthetic approach to construct (N)-methanocarba carbocyclic nucleosides.

Figure 2:
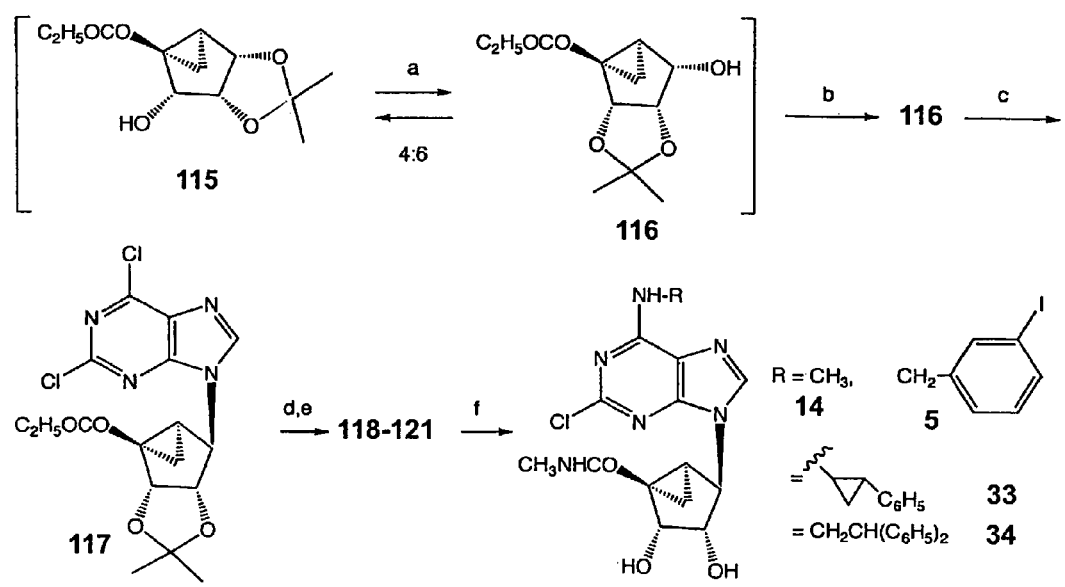
FIG. 2 depicts a reaction scheme for the synthesis of compounds 33 and 34 in accordance with an embodiment of the invention. Reagents and conditions: (a) p-TsOH, acetone, reflux; (b) crystallization; (c) 2,6-dichloropurine, DIAD, TPP, THF, room temperature; (d) 3-iodobenzylamine.HCl, TEA (for 5), 40% aq. $MeNH_2$ (for 14), trans-2-phenylcyclopropylamine.HCl, TEA (for 33), 2,2-diphenylethylamine (for 34), in MeOH room temperature; (e) 40% aq. $MeNH_2$; (f) 10% $CF_3COOH$ in MeOH, $H_2O$, room temperature.
Figure 3:
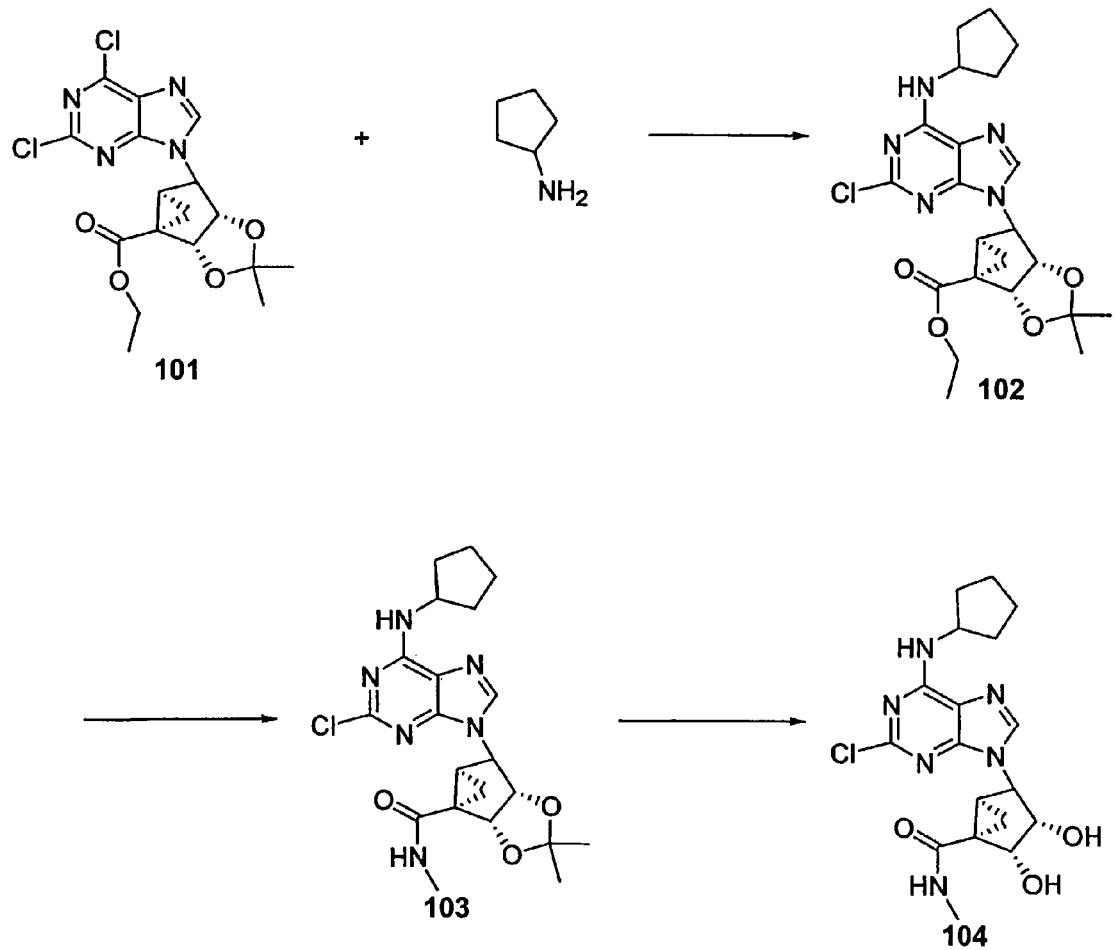
FIG. 3 depicts a reaction scheme for the synthesis of compound 104 in accordance with an embodiment of the invention.

The nucleobase coupling was carried out via a Mitsunobu reaction (FIG. 2). Accordingly, alcohol 115 was subjected to an acid-catalyzed equilibration to produce the isomeric acetonide 116, which was isolated in 90% yield (based on recovery of alcohol 115) by careful crystallization from cyclohexane. The requisite alcohol 116 when subjected to a Mitsunobu coupling reaction with 2,6-dichloropurine afforded the condensed product 117 in 36% yield. Treatment of 117 with excess of $CH_3NH_2$ followed by deprotection of the acetonide group afforded authentic (N)-methanocarba nucleoside 14 (MRS 2346), whose spectral properties matched those reported in the literature. Lee et al., *Bioorg. Med. Chem. Lett.* 2001, 11, 1333-1337. In addition, reaction of 117 with 3-iodobenzylamine in the presence of $Et_3N$, followed by reaction with excess of $CH_3NH_2$, provided compound 119. Removal of the acetonide by standard methods produced the other target 5 (MRS 1898) in 74% yield. The spectral properties of 5 matched those of the identical compound reported in the literature. Lee et al. supra. To demonstrate the generality of this route, other novel $N^6$-substituted (N)-methanocarba nucleosides, e.g., 33 and 34, were prepared in reasonable yields.

Synthetic reagents were purchased from Sigma Chemical Co. (St. Louis, Mo.) and Aldrich (Milwaukee, Wis.). $^1$H-NMR spectra were obtained with a Varian Gemini-300 spectrometer (300 MHz) with $D_2O$, $CDCl_3$, $CD_3OD$, and DMSO-$d_6$ as solvents. Low-resolution mass spectra were measured with a Finnigan-Thermoquest LCQ with APCI (Atmospheric Pressure Chemical Ionization) interface. Low-resolution and high-resolution FAB (fast atom bombardment) mass spectrometry was performed with a JEOL SX102 spectrometer with 6-kV Xe atoms following desorption from a glycerol matrix.

2,3-O-Isopropylidene-D-erythrose (106) was prepared from commercially available 2,3-O-isopropylidene-D-erythronolactone (105) by the procedure of Cohen et al. (*J. Amer. Chem. Soc.* 1983, 105, 3661-3672) in 90% yield.

(4R,5S)-(2,2-Dimethyl-5-vinyl-1,3-dioxolan-4-yl) methan-1-ol (107). To a solution containing methyltriphenyl phosphonium bromide (7.85 g, 22 mmol) in dry THF (60 mL) was added potassium-tert-butoxide (2.2 g, 20.0 mmol). The resulting reaction mixture was stirred at room temperature for 1 h under nitrogen. The lactol 36b (1.60 g, 10 mmol) in dry THF (20 ml) was added at −78° C., and the reaction was allowed to reach room temperature. After stirring for an additional 3 h, it was treated with saturated brine (100 mL). The aqueous layer was extracted with ethyl acetate (50 mL). The combined organic layers were washed with brine, dried ($Na_2SO_4$) and concentrated. Purification by column chromatography (silica gel; EtOAc:hexanes, 25:75) gave 107 (0.94 g, 60%) as an oil; $[\alpha]_D^{25}$+41.2 (c 2.5 $CHCl_3$) [Rao et al., *J. Carbohydr. Chem.* 1996, 15, 975-984] $[\alpha]_D^{25}$+40.1] with identical spectral properties as reported in Rao et al.

Ethyl (4S,5S)-3-[2,2-dimethyl-5-vinyl(1,3-dioxolan-4-yl)]-3-oxopropanoate 110. Method A. From compound 107, the acid 109 was prepared according to the work of Rao et al., supra. A stirred solution of 109 (0.35 g, 2.03 mmol) in THF (3 mL) maintained 0° C. was treated with 1,1'-carbonyldiimidazole (0.43 mg, 2.64 mmol). After 30 min, the temperature was raised to 30° C. and additional stirring continued for 2 h. After cooling to room temperature, this solution was added via cannula to a −78° C. solution of $LiCH_2CO_2CH_2CH_3$ obtained from EtOAc (0.6 mL, 6.14 mmol) and LDA (0.48 g, 6.1 mmol) in anhydrous THF (5 mL) during 1.5 h at −78° C. The reaction was quenched at the same temperature with 1N HCl (6.1 mL), stirred further at −78° C. for 10 min, allowed to warm up to 0° C., adjusted to pH 3, and extracted with EtOAc (80 mL). The combined organic extract was washed with brine, dried ($MgSO_4$) and concentrated under reduced pressure. The residue was purified by silica gel column chromatography (hexanes:EtOAc, 7:1) to give the desired β-keto ester 110 (0.293 g, 59%) as a clear oil. A small amount of the (4R,5S)-isomer 111 (0.038 g, 8%) was also obtained as a clear oil.

110: IR (neat) 1748, 1722 cm$^{-1}$; $[\alpha]_D^{25}$=−42.7° (c 0.26, $CHCl_3$); $^1$H NMR ($CDCl_3$); δ12.08 (s, 0.1 H, $D_2O$ exchangeable, enolic OH), 5.92-6.06 (m, 1 H), 5.37-5.56 (m, 2 H), 4.51-4.62 (m, 1 H), 4.20-4.38 (m, 3 H), 3.75 (AB q, 2 H, J=16.4 Hz), 1.54-1.57 (m, 6 H, 2), 1.34-1.41 (m, 3 H); FAB MS m/z (relative intensity) 185 (7.2), 243 (MH$^+$, 2).

111: IR (neat) 1750, 1721 cm$^{-1}$; $[\alpha]_D^{25}$=+29.9° (c 1.23 $CHCl_3$); δ12.00 (s, 1 H, $D_2O$ exchangeable, enolic OH), 5.72-5.90 (m, 1 H), 5.30-5.57 (m, 2 H), 4.85-4.99 (m, 1 H), 4.22-4.33 (m, 2 H), 3.69 (d, 1 H, J=16.4 Hz), 3.43 (d, 1 H, J=16.4 Hz), 1.70 (s, 3 H), 1.48 (s, 3 H), 1.32-1.40 (m, 3 H); FAB MS m/z (relative intensity) 185 (98), 243 (MH$^+$, 38).

Method B. A solution of dry DMSO (1.75 g, 22.4 mmol) in dry $CH_2Cl_2$ (20 mL) was added to a solution of $(COCl)_2$ (1.52 g, 12 mmol) in dry $CH_2Cl_2$ (40 mL), which had been cooled to −78° C. under a nitrogen atmosphere. The resulting reaction mixture was further stirred at the same temperature for another 15 min before a solution of alcohol 107 (1.27 g, 8 mmol) in dry $CH_2Cl_2$ (15 mL) was added carefully over 10 min, while the temperature was kept at −78° C. The stirring was continued for 30 min and then dry $Et_3N$ (8.0 g, 80 mmol) was added at the same temperature. The mixture was allowed to warm to room temperature, $CH_2Cl_2$ (100 mL) was subsequently added, and again it was cooled to −78° C. The solution was treated with saturated NaCl (40 mL) and then the reaction mixture was allowed to warm to room temperature. The organic layer was separated, dried ($Na_2SO_4$), and concentrated under reduced pressure. The crude aldehyde 36d (3.0 g) was dissolved in $CH_2Cl_2$ (40 mL) and treated with $SnCl_2$ (5.10 g, 24 mmol) and ethyl diazoacetate (1.14 g, 10 mmol). The mixture was stirred at room temperature for 3 h. The reaction mixture was filtered through a pad of Celite (20.0 g), and the resulting organic layer was concentrated. The desired keto ester was purified by column chromatography (silica gel; hexanes:EtOAc-hexanes, 95:5) to furnish 110 as oil (0.69 g, 36%) with identical spectroscopic properties as those reported under Method A.

Ethyl (4S,5S)-3-[2,2-dimethyl-5-vinyl(1,3-dioxolan-4-yl)]-2-diazo-3-oxopropanoate 112. To a stirred solution of keto ester 110 (4.84 g, 20 mmol) in acetonitrile (40 mL) was successively added tosyl azide (4.13 g, 21 mmol) and $Et_3N$ (4.4 g, 40 mmol). The resulting reaction mixture was concentrated after stirring for 30 min at room temperature. The diazo derivative was purified by column chromatography (silica gel; hexanes:EtOAc, 95:5) to furnish 112 (3.75 g, 70%) as an oil; IR (neat) 2141, 1713 cm$^{-1}$; $[\alpha]_D^{25}$=+81.0° (c 2.02, $CHCl_3$); $^1$H NMR ($CDCl_3$) δ5.77 (ddd, 1 H, J=17.3, 10.1, 7.3 Hz), 5.70 (d, 1 H, J=7.6 Hz), 5.45 (dm, 1 H, J=17.1 Hz), 5.30 (dm, 1 H, J=10.2 Hz), 5.05 (t, 1 H, J=7.5 Hz), 4.36 (q, 2 H, J=7.1 Hz), 1.74 (s, 3 H), 1.51 (s, 3 H), 1.41 (t, 3 H, J=7.1 Hz); FAB MS m/z (relative intensity) 269 (MH$^+$, 86). This compound was used for the next step without further purification.

Ethyl (1S,3S,4S,5S)-3,4-O-isopropylidene-2-oxobicyclo [3.1.0]-hexanecarboxylate 113. To a stirred solution of diazo compound 36h (5.36 g, 20 mmol) in dry toluene (15 mL) was added CuI (0.190 g, 1 mmol) at room temperature and the reaction mixture was refluxed for 8 h. The reaction mixture was cooled to room temperature, concentrated and purified by column chromatography (silica gel; hexanes:EtOAc, 75:25) to provide bicylic compound 113 (1.72 g, 36%) and compound 114 (0.57 g, 12%).

113: IR (neat) 1751, 1719 cm$^{-1}$; $[\alpha]_D^{25}$=+33.60° (c 1.69, $CHCl_3$); $^1$H NMR ($CDCl_3$) δ5.12 (ddd, 1 H, J=8.3, 5.4, 1.0 Hz), 4.45 (d, 1 H, J=8.3 Hz), 4.29 (q, 2 H, J=7.1 Hz), 2.84 (dt, 1 H, J=8.3, 5.3 Hz), 2.18 (dd, 1 H, J=8.1, 5.1 Hz), 1.89 (t, 1 H, J~5.2 Hz), 1.59 (s, 3 H), 1.39 (s, 3 H), 1.36 (t, 3 H, J=7.1 Hz); FAB MS m/z (relative intensity) 241 (MH$^+$, 100). Anal. calcd for $C_{12}H_{16}O_5$: C, 59.99; H, 6.71. Found: C, 59.95; H, 6.80.

114: IR (neat) 1755, 1722 cm$^{-1}$; $[\alpha]_D^{25}$=+67.90° (c 1.12, $CHCl_3$); $^1$H NMR ($CDCl_3$) δ4.8(d, 1 H, J=5.1 Hz), 4.38 (dd, 1 H, J=4.8, 1.7 Hz), 4.32 (dq, 2 H, J=7.1, 1.5 Hz), 2.96 (dd, 1 H, J=8.7, 5.7 Hz), 2.21 (ddd, 1 H, J=8.8, 5.7, 1.7 Hz), 1.53 (s, 3 H), 1.45 (s, 3 H), 1.37 (t, 3 H, J=4.1 Hz), 1.35 (irregular t, 1 H); FAB MS m/z (relative intensity) 241 (MH$^+$, 100). Anal. calcd for $C_{12}H_{16}O_5$.0.45 $H_2O$: C, 58.03; H, 6.86. Found: C, 57.96; H, 6.76.

Ethyl (1S,2R,3S,4S,5S)-3,4-O-isopropylidene-2-hydroxybicyclo[3.1.0]hexane-carboxylate 115. To a stirred solution of 113 (1.20 g, 5 mmol) in methanol (20 mL) at room temperature was added $NaBH_4$ (0.19 g, 5 mmol) while stirring continued for an additional 1 h. The reaction mixture was then treated with acetone (2 mL) and concentrated to dryness.

The residue was purified by column chromatography (silica gel; hexanes:EtOAc, 70:30) to give compound 115 (0.87 g, 72%) as a white solid; m.p. 1090° C. (cyclohexane); $[\alpha]_D^{25}=+72.0°$ (c 0.15, CH$_2$Cl$_2$); $^1$H NMR (CDCl$_3$) δ4.95 (t, 1 H, J=7.5 Hz), 4.88 (t, 1 H, J=6 Hz), 4.60 (t, 1 H, J=7 Hz), 4.12-4.24, (m, 2 H), 2.48 (d, 1 H, J=12 Hz, OH), 2.16-2.26 (m, 1 H), 1.48-1.61 (m, 5 H), 1.32 (s, 3 H), 1.26 (t, 3 H, J=6.5 Hz). FAB MS m/z (relative intensity) 243 (MH$^+$, 100). Anal. calcd for C$_{12}$H$_{18}$O$_5$: C, 59.49; H, 7.49, Found: C, 59.36; H, 7.54.

Ethyl (1S,2R,3S,4S,5S)-2,3-O-(isopropylidene)-4-hydroxybicyclo[3.1.0]hexane-carboxylate 116. A solution of 37 (0.48 g, 2.0 mmol) and p-TsOH.H$_2$O (0.19 g, 1 mmol) in acetone (20 mL) was refluxed for 8 h. Following the addition of NEt$_3$ (1 mL), the solution was concentrated under reduced pressure. Flash column chromatography (silica gel; CHCl$_3$:MeOH, 9:1) of the residue furnished a mixture of isomerized alcohols 115 and 116 in a 6:4 ratio based on NMR. This crude mixture was further purified by careful crystallization from cyclohexane to obtain the requisite pure 116 (0.196 g, 41%) as colorless crystals. The remaining alcohol 115 was recycled.

116: m.p. 80° C.; $[\alpha]_D^{25}=+124.0°$ (c 0.15, CH$_2$Cl$_2$); $^1$H NMR (CDCl$_3$) δ 5.38 (d, 1 H, J=5.5 Hz), 4.42-4.64 (m, 2 H), 4.08-4.21 (m, 2 H), 2.39-2.45 (m, 2 H), 1.42-1.62 (m, 5 H), 1.35 (s, 3 H), 1.12 (t, 2 H, J=3.2 Hz); FAB MS m/z (relative intensity) 243.1 (MH$^+$, 100). Anal. calcd for C$_{12}$H$_{18}$O$_5$: C, 59.49; H, 7.49. Found: C, 59.46; H, 7.59.

Ethyl (1'S,2'R,3'S,4'R,5'S)-4'-(2,6-dichloropurin-9-yl]-2',3'-O-(isopropylidene)-bicyclo[3.1.0]hexanecarboxylate 117. A mixture of triphenyl phosphine (0.104 g, 0.4 mmol), 2,6-dichloropurine (0.075 g, 0.4 mmol) in dry THF (2 mL) was treated with diisopropylazodicarboxylate (0.80 g, 0.4 mmol) at room temperature. After 20 min stirring, a solution of 116 (0.048 g, 0.2 mmol) in THF (1 mL) was added and the mixture was stirred further for 8 h. Concentration and purification of the residue by column chromatography (silica gel; CHCl$_3$:MeOH, 9:1) furnished 117 (0.029 g, 36%) as a white solid; m.p. 104° C.; $[\alpha]_D^{25}=+34°$ (c 0.1, CH$_2$Cl$_2$); $^1$H NMR (CDCl$_3$) δ8.09 (s, 1 H), 5.85 (d, 1 H, 6.5 Hz), 4.91 (s, 1 H), 4.72 (d, 1 H, J=5.5 Hz), 4.05-4.38 (m, 2 H), 2.14-2.2 (m, 1 H), 1.75-1.82 (m, 1 H), 1.52-1.62 (m, 4 H), 1.15-1.38 (m, 6 H); FAB MS m/z (relative intensity) 413.1 (MH$^+$, 100). Anal. calcd for C$_{17}$H18C$_{12}$N$_4$O$_4$: C, 49.41; H, 4.39; N, 13.56. Found: C, 49.14; H, 4.64; N, 13.26.

(1'S,2'R,3'S,4'R,5'S)-{4'-[2-chloro-6-(methylamino)purin-9-yl]-2',3'-O-(isopropylidene)bicyclo[3.1.0]hexyl}-N-methylcarboxamide 118. A stirred solution of 37b (0.041 g, 0.1 mmol) in MeOH (2 mL) was treated with aqueous CH$_3$NH$_2$ (0.5 mL, 40%) for 8 h at room temperature The reaction mixture was concentrated to dryness and the product was purified by preparative TLC using CHCl$_3$:MeOH, 9:1 as the mobile phase to afford 118 (0.022 g, 60%) as white solid; m.p. 221° C.; $[\alpha]_D^{25}=+10.0°$ (c 0.05, MeOH); $^1$H NMR (CDCl$_3$) δ7.71 (s, 1 H), 6.92 (br s, 1 H), 6.08 (s, 1 H), 5.65 (d, 1 H, J=5.4 Hz), 4.63-4.84 (m, 2 H), 3.11 (br s, 3 H), 2.95 (d, 3 H, J=3.8 Hz), 1.95-2.06 (m, 1 H), 1.61-1.66 (m, 1 H), 1.56 (s, 3 H), 1.08-1.24 (m, 4 H); FAB MS m/z (relative intensity) 393.1 (MH$^+$, 100). Anal. calcd for C$_{17}$H$_{21}$ClN$_6$O$_3$: C, 51.98; H, 5.39; N, 21.39. Found: C, 51.71; H, 5.86; N, 20.82.

(1'S,2'R,3'S,4'R,5'S)-{4'-[2-chloro-6-(methylamino)purin-9-yl)]2',3'-dihydroxy-bicyclo[3.1.0]hexyl}-N-methylcarboxamide (14). A mixture of amide 118 (0.016 g, 0.04 mmol) containing 10% trifluoroacetic acid/MeOH (5 mL) and H$_2$O (0.5 mL) was heated at 70° C. for 3 h. The solvent was removed and the residue was dried by coevaporation with toluene. The residue was purified using preparative TLC (CHCl$_3$:MeOH, 9:1) to afford 14 (0.010 g, 71%) as a white solid; m.p. 248° C. dec.; $[\alpha]_D^{25}=+16.0°$ (c 0.05, CH$_2$Cl$_2$); $^1$H NMR (DMSO-d$_6$) δ 8.22 (br s, 1 H), 8.05 (s, 1 H), 7.55 (br s, 1H), 5.38 (d, 1 H, J=2.5 Hz), 4.80-4.94 (m, 2 H), 4.61 (s, 1 H), 3.76-3.86 (m, 2 H), 3.30 (br s, 3 H), 2.74(d, 3 H, J=2.5 Hz), 1.74-1.83 (m, 1 H), 1.61 (t, 1 H, J=2.4 Hz), 1.21-132 (m, 1 H); FAB MS m/z (relative intensity) 353.07 (MH$^+$, 100). Anal. calcd for C$_{14}$H$_{17}$ClN$_6$O$_3$.0.25H$_2$O: C, 47.06; H, 4.94; N, 23.52. Found: C, 47.06; H, 5.24; N, 23.98.

(1'S,2'R,3'S,4'R,5'S)-(4'-{2-chloro-6-[(3-iodophenyl)amino]purin-9-yl}-2',3'-O-(isopropylidene)bicyclo[3.1.0]hexyl)-N-methylcarboxamide 119. A solution of 117 (0.042 g, 0.1 mmol) in MeOH (2 mL) was treated with 3-iodobenzylamine hydrochloride (0.078 g, 0.15 mmol) and Et$_3$N (0.5 ml) and stirred at room temperature for 3 h. The reaction mixture was concentrated to dryness and the resulting residue was purified by flash column chromatography (silica gel; CHCl$_3$:MeOH, 9:1). The intermediate product was dissolved in MeOH (3 mL), treated with excess of aqueous CH$_3$NH$_2$ (0.5 ml, 40%), and stirred at room temperature for 6 h. After evaporating to dryness and preparative TLC purification (CHCl$_3$:MeOH, 9:1) 115 (0.028 g, 46%) was obtained as a white solid; m.p.156° C.); $[\alpha]_D^{25}=+7.50°$ (c 0.04, MeOH); $^1$H NMR (CDCl$_3$) δ 7.61-7.78 (m, 3 H), 7.38 (d, 1 H, J=5.4 Hz), 7.09 (t, 1 H, J=5.7 Hz), 6.82 (br s, 1 H), 6.35 (br s, 1 H), 5.63 (d, 1 H, J=6.3 Hz), 4.65-4.82 (m, 3 H), 2.91 (d, 3 H, J=2.5 Hz), 2.02-2.11 (m, 1 H), 1.11-1.92 (m, 8 H); FAB MS m/z (relative intensity) 595.1 (MH$^+$, 100). Anal. calcd for C$_{23}$H$_{24}$ClIN$_6$O$_3$.0.5H$_2$O: C, 45.75; H, 4.17; N, 13.92. Found: C, 45.92; H, 4.16; N, 13.89.

(1'S,2'R,3'S,4'R,5'S)-[4'-(2-chloro-6-{[(3-iodophenyl)methyl]amino}purin-9-yl)-2',3'-dihydroxybicyclo[3.1.0]hexyl]-N-methylcarboxamide (5). A mixture of amide 119 (0.024 g, 0.04 mmol) containing 10% trifluoroacetic acid in MeOH (5 mL) and H$_2$O (0.5 mL) was heated at 70° C. for 3 h. The solvent was removed, and the residue was dried by coevaporation with toluene. The residue was purified using preparative TLC (CHCl$_3$: MeOH, 9:1) to afford 5 (0.016 g, 74%) as a white solid; m.p. 230° C.); $[\alpha]_D^{25}=+7.0°$ (c 0.1, MeOH); $^1$H NMR (DMSO-d$_6$) δ 8.84 (br s, 1 H), 8.11 (s, 1 H), 7.78 (s, 1 H), 7.42-7.62 (m, 2 H), 7.36 (d, 1 H, J=3.5 Hz), 7.14 (t, 1 H, J=4.5 Hz), 5.44 (d, 1 H, J=4.8 Hz), 4.75-4.91 (m, 2 H), 4.56-4.69 (m, 2 H), 3.86-3.92 (m, 1 H), 2.67 (d, 1 H, J=2.5 Hz), 1.81-1.89 (m, 1 H), 1.61-165 (m, 1 H), 1.23-1.29 (m, 1 H); FAB MS m/z (relative intensity) 555.1 (MH$^+$, 100). Anal. calcd for C$_{20}$H$_{20}$ClIN$_6$O$_3$.0.5H$_2$O: C, 42.61; H, 3.75; N, 14.91. Found: C, 42.54; H, 3.76; N, 14.52.

(1'S,2'R,3'S,4'R,5'S)-(4'-{2-chloro-6-[(trans-2-phenylcyclopropyl)amino]purin-9-yl}-2',3'-O-(isopropylidene)bicyclo[3.1.0]hexyl)-N-methylcarboxamide 120. Using the same procedure described for the synthesis of 119, except for the use of trans-2-phenylcyclopropylamine, compound 120 (0.023 g, 48%) was obtained as a solid; m.p. 168° C.; $[\alpha]_D^{25}=+4.0°$ (c 0.1, MeOH); $^1$H NMR (CDCl$_3$) δ 7.71 (s, 1 H), 7.19-7.38, (m, 5 H), 6.98 (br s, 1 H), 6.18 (bs, 1 H), 5.68 (d, 1 H, J=5.2 Hz), 5.76-5.82 (m, 3 H), 2.91 (d, 1 H, J=3.6 Hz), 2.18-2.23 (m, 1 H), 1.97-2.08 (m, 1 H), 1.54-1.78 (m, 5 H), 1.22-1.34 (m, 5 H); FAB MS m/z (relative intensity) 495.3 (MH$^+$, 100). Anal. calcd for C$_{25}$H$_{27}$ClN$_6$O$_3$.0.25H$_2$O: C, 58.02; H, 5.75; N, 16.24. Found: C, 58.17; H, 5.46; N, 15.85.

(1'S,2'R,3'S,4'R,5'S)-(4'-{6-[(2,2-diphenylethyl)amino]-2-chloropurin-9-yl}-2',3'-O-(isopropylidene)bicyclo[3.1.0]hexyl)-N-methylcarboxamide 121. Using the same procedure described for the synthesis of 119, except for the use of 2,2-diphenylethylamine, compound 121 (0.023 g, 42%) was obtained as a solid; m.p. 145° C.; $[\alpha]_D^{25}=+8.0°$ (c 0.1, MeOH); $^1$H NMR (CDCl$_3$) δ 7.21-7.78 (m, 11 H), 6.83 (br s, 1 H), 6.26 (br s, 1H), 5.66 (d, 1 H, J=5.6 Hz), 4.21-4.83 (m, 5

H), 2.91 (d, 3 H, J=4.8 Hz), 1.97-2.03 (m, 1 H), 1.23-1.78 (m, 8 H); FAB MS m/z (relative intensity) 559.3 (MH$^+$, 100). Anal. Calcd for $C_{30}H_{31}ClN_6O_3 \cdot H_2O$: C, 63.43; H, 5.68; N, 14.79. Found: C, 63.19; H, 5.71; N, 15.05.

(1'S,2'R,3'S,4'R,5'S)-(4'-{2-chloro-6-[(trans-2-phenylcyclopropyl)amino]purin-9-yl}-2',3'-dihydroxybicyclo[3.1.0] hexyl)-N-methylcarboxamide (33). Starting from compound 120 and following the same procedure described for the synthesis of 5, compound 33 (0.013 g, 72%) was obtained as a solid; m.p. 230° C. dec; $[\alpha]_D^{25}$=+19.0° (c 0.1, MeOH); $^1$H NMR (CDCl$_3$) δ 7.82 (s, 1 H), 7.23-7.38 (m, 5 H), 6.92 (br s, 1 H), 6.31 (br s, 1 H), 4.98 (d, 1 H, J=4.8 Hz), 4.83 (s, 1 H), 4.08-4.29 (m, 2 H), 2.92 (d, 3 H, J=4.8 Hz), 2.08-2.23 (m, 1 H), 1.62-1.96 (m, 2 H), 1.21-1.44 (m, 3 H); FAB MS m/z (relative intensity) 455.2 (MH$^+$, 100). Anal. calcd for $C_{22}H_{23}ClN_6O_3 \cdot 0.5H_2O$: C, 56.96; H, 5.21; N; 18.12. Found: C, 57.17; H, 4.93; N, 16.47.

[(2,2-diphenylethyl)amino]-2-chloropurin-9-yl}dihydroxybicyclo[3.1.0]hexyl)-N-methylcarboxamide (34). Starting from compound 121 and following the same procedure described for the synthesis of 14, compound 34 (0.014 g, 70%) was obtained as a solid; m.p. 232° C. dec; $[\alpha]_D^{25}$=+6.0° (c 0.1, MeOH); $^1$H NMR (CDCl$_3$) δ 7.76 (s, 1 H), 7.21-7.38 (m, 10 H), 6.83 (br s, 1 H), 5.97 (br s, 1 H), 4.96 (d, 1 H, J=4.8 Hz), 4.80 (br s, 1H), 4.02-4.38 (m, 4 H), 2.91 (d, 3 H, J=4.8 Hz), 2.12-2.21 (m, 1 H), 1.21-1.39 (m, 2 H); FAB MS m/z (relative intensity) 519.3 (MH$^+$, 100). Anal. calcd for $C_{27}H_{27}ClN_6O_3 \cdot H_2O$: C, 60.39; H, 5.44; N, 15.65. Found: C, 60.61; H, 5.34; N, 15.64.

Figure 4:
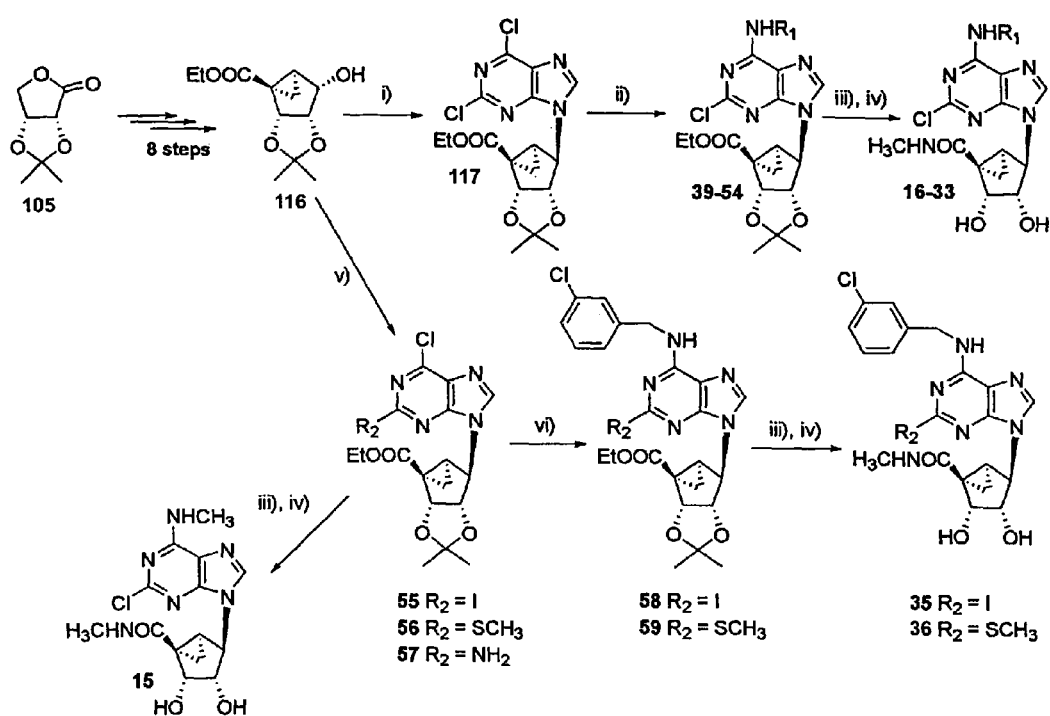
FIG. 4 depicts a reaction scheme for the synthesis of compounds 15-33, 35-36, and 55-59 in accordance with an embodiment of the invention.
Figure 5:
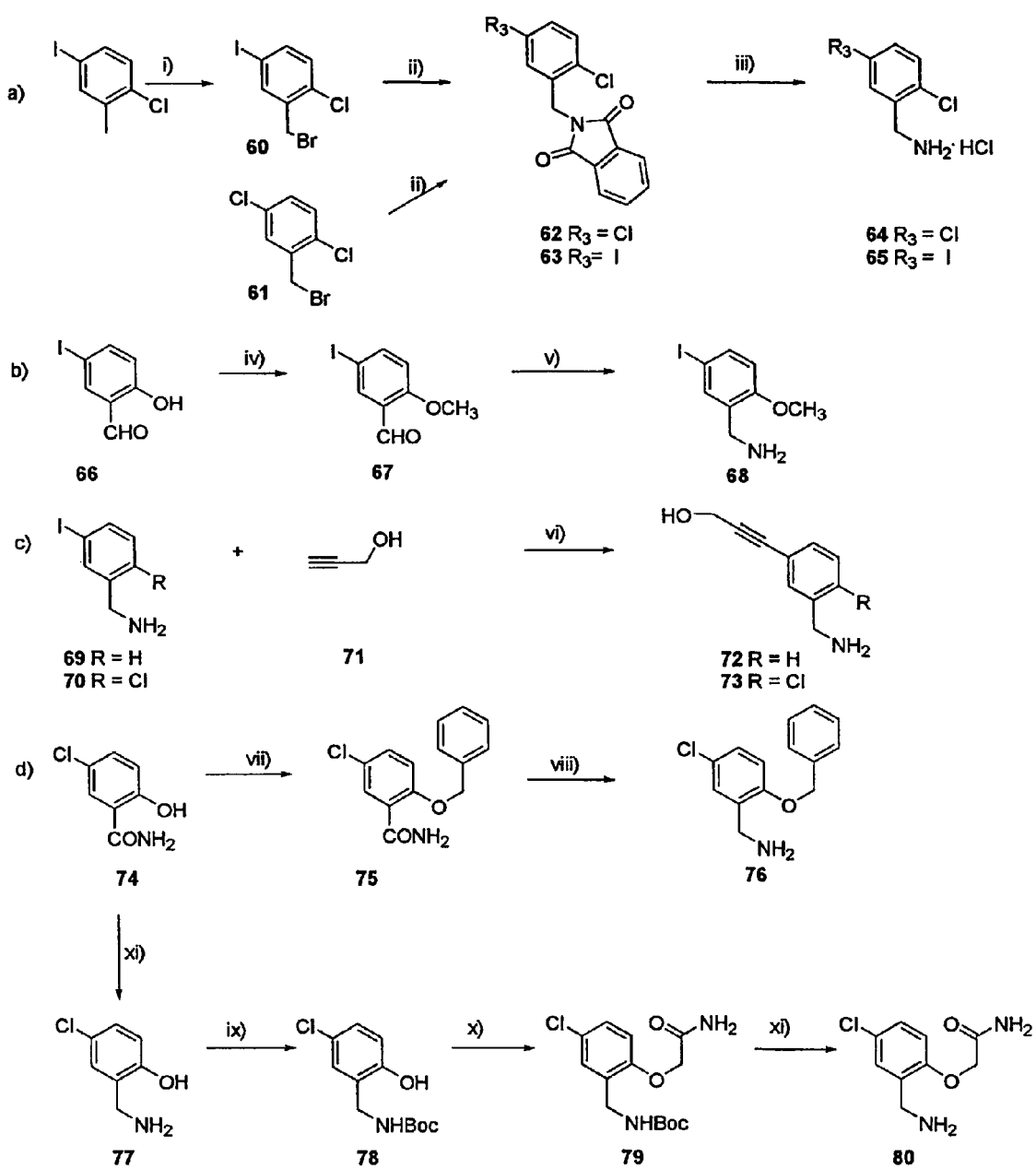
FIG. 5 depicts a reaction scheme for the synthesis of intermediate compounds 60-80 useful for the preparation of certain compounds in accordance with an embodiment of the invention.
Figure 6:
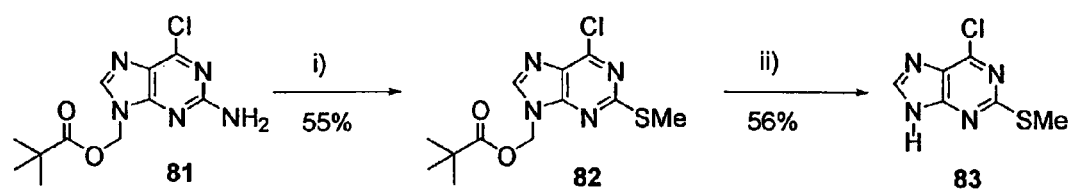
FIG. 6 depicts a reaction scheme for the synthesis of intermediate compounds 81-83 useful for the preparation of certain compounds in accordance with an embodiment of the invention.
Figure 7:
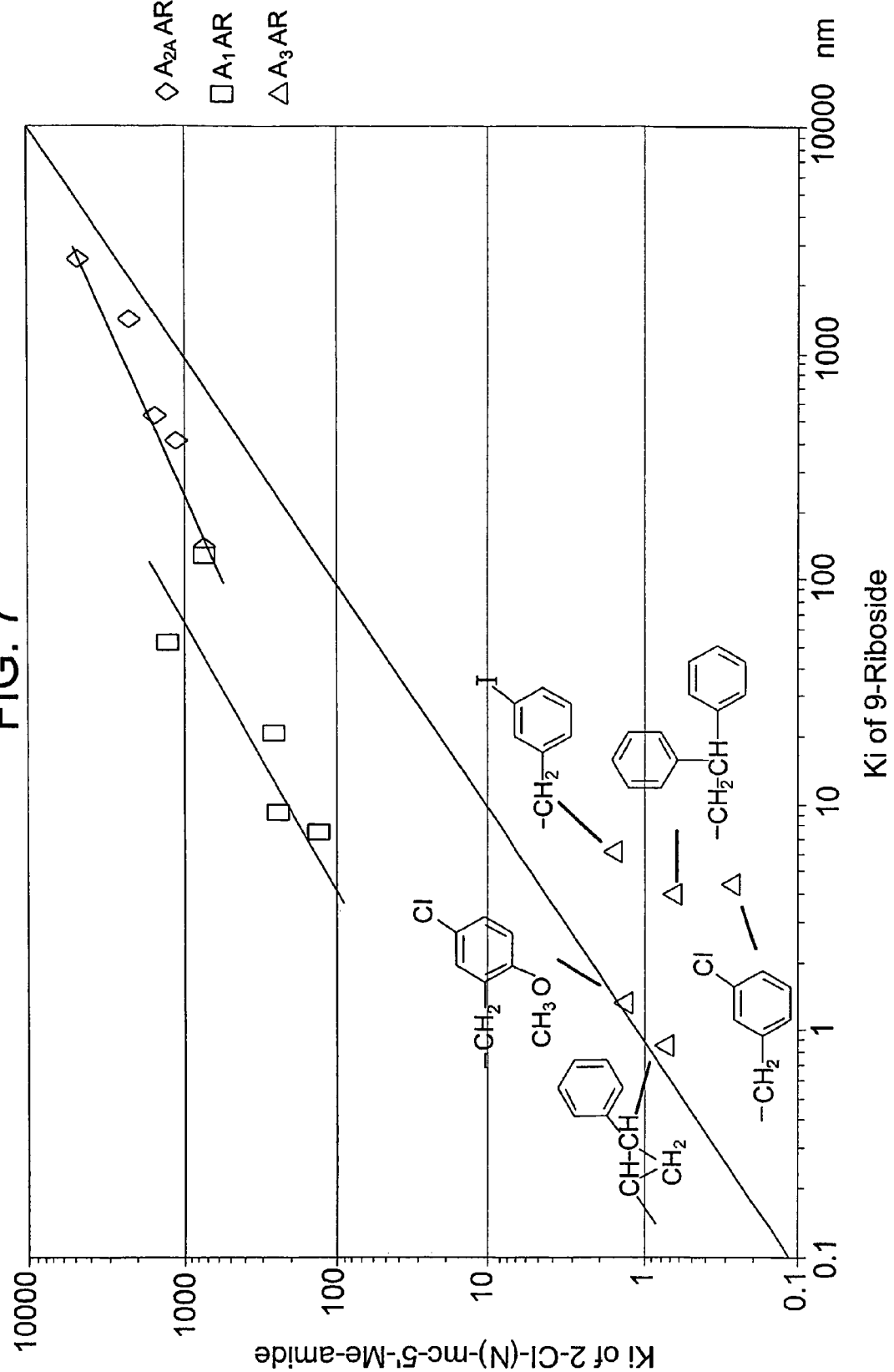
FIG. 7 depicts a correlation of the binding constant (Ki) at human adenosine receptors in two structural series. The X-axis represents the Ki value of compounds having a riboside at the 9-position. The Y-axis represents the Ki value of 2-chloro substituted 5'-methyl uronamide having a 9-position substituent which is ring constrained with a Northern conformation. For $A_1$ (squares) and $A_2$ (diamonds) adenosine receptors, the observed values fall on the predicted solid lines; for the $A_3$ (triangles), the observed Ki values fall below the predicted line, thereby indicating that the of $A_3$ selectivity is surprisingly enhanced by the inclusion of the constrained 9-position substituent relative to the selectivity to $A_1$ and $A_2$ adenosine receptors.

Compounds 15 and 17-36 were synthesized as shown in FIGS. 4-6. Most analogues contained a 2-chloro substituent, although 2-amino (15), 2-iodo (35), and 2-alkylthio (36) groups were also included.

The general synthetic route follows the method of Joshi et al., supra. The protected (N)-methanocarba ring system 116 containing a carbonyl group at the 5'-position was prepared in 8 steps from isopropylidene erythronolactone 105. Compound 37 and the nucleobase precursor, 2,6-dichloropurine, were condensed using a Mitsunobu coupling. Substitution of the 6-chloro of 117 was then carried out by treating with an excess of the appropriate amine, such as a substituted benzylamine, to provide the series of protected nucleoside 5'-esters 39-54. Following appropriate substitution at the N$^6$ position, the 5'-esters were treated with an excess of methylamine, and the isopropylidene group was removed from the 2'-and 3'-hydroxyl groups upon acid treatment to provide compounds 16-33.

The various benzylamine derivatives used in this study, when not commercially available, were synthesized by the methods shown in FIG. 5. 2,5-Dichlorobenzylamine 64 and 2-chloro-5-iodobenzylamine 65 were prepared from the corresponding benzyl bromides. Compound 60 was prepared from 2-chloro-5-iodotoluene by bromination with N-bromosuccinimide in CCl$_4$. Wilson et al., J. Med. Chem 1989, 32, 1057-1062. 60 and 61 were treated with potassium phthalimide in N,N-dimethylformamide at 60° C. to obtain compounds 62 and 63 as white solids in 95% yield. Deprotection with hydrazine gave 64 and 65 in 80% yield. Treu et al., Molecules 2002, 7, 743-750.

5-Iodo-2-methoxybenzylamine 68 was prepared starting from 5-iodosalicylaldehyde 66. Accordingly, compound 66 was methylated with methyl iodide in the presence of K$_2$CO$_3$ in N,N-dimethylformamide and subsequently, the formyl moiety was transformed to methylamino by reductive amination with NaCNBH$_4$ in the presence of ammonium acetate. William s et al., JOC 1989, 52, 2615-2617.

Compounds 72 and 73 were synthesized through a Sonogashira-type reaction in high yield using CuI and (Ph$_3$P)PdCl$_2$ as catalysts. Sonogashira et al., Tet. Lett. 1975, 4467-4470. For the preparation of both 5-chloro-2-benzyloxybenzylamine 76 and 5-chloro-2-(aminocarbonylmethyloxy)benzylamine 80, 5-chloro-2-hydroxybenzamide 74 was used as starting material. Compound 74 was treated with benzyl bromide in the presence of K$_2$CO$_3$ in N,N-dimethylformamide to obtain 5-chloro-2-benzyloxybenzamide 75 in 98% yield. Finally, the amide 75 was reduced to the corresponding amine 76 with LiAlH$_4$ in tetrahydrofuran.

Reduction of compound 74 with LiAlH$_4$ in tetrahydrofuran gave 5-chloro-2-hydroxybenzylamine 77 in 88% yield. This preparation showed an improvement over the reported procedure, based on the hydrogenation of 5-chloro-2-hydroxybenzaldehyde oxime. Tucker et al., J. Med. Chem., 1998,41, 3210-3219. The amine 77 was protected as a t-butylcarbamate 78, and the hydroxyl group was alkylated with 2-bromoacetamide in the presence of K$_2$CO$_3$ in N,N-dimethylformamide. The subsequent deprotection of the amino group with 15% trifluoroacetic acid in dichloromethane gave the final product 80 as a white solid.

Substitution at the 2-position by groups other than chloro was possible and accomplished by condensing the appropriate 2-substituted nucleobases with the (N)-methanocarba sugar moiety 116 to provide the protected nucleoside esters 55 and 56 FIG. 4. Successive treatment with 3-chlorobenzylamine and methylamine followed by subsequent acid hydrolysis afforded the 2-iodo and 2-thiomethyl analogues 35 and 36. Alternatively, the 2-amino substituted analogue was obtained by first condensing the 2-amino substituted nucleobase with 116 followed by the direct interaction with excess methylamine and subsequent hydrolysis to afford 15.

The requisite 6-chloro-2-iodopurine was prepared by a literature procedure, Brun et al., Tet. Lett., 2001, 42 8161-8164 while 6-chloro-2-methylthiopurine was prepared as delineated in FIG. 6. Accordingly, 6-chloro-2-methylthiopurin-9-yl-methyl 2,2-dimethylpropionate (Kim et al., J. Med. Chem., 2003, 46, 4974-4987) 81 was diazotized with tert-butyl nitrite, and the resulting diazo intermediate was trapped with an excess of methyl disulfide to afford 82, which upon hydrolysis of the pivaloylmethyloxy protecting group with aqueous NaOH, gave the requisite 2-methylthiopurine 83.

Materials and instrumentation. Compound 11 was purchased from Sigma (St. Louis, Mo.), and compounds 3 and 4 were prepared as reported. Gallo-Rodriguez et al., J. Med. Chem. 1994, 37, 636-646; Kim et al., J. Med. Chem. 1994, 37, 3614-3621. Compounds 9 and 10 were prepared as reported. Ohno et al., Bioorg. med. chem. 2004, 12, 2995-3007; Tchilibon et al., Bioorg. Med. Chem. 2004, 12, 2021-2034.

Reagents and solvents were purchased from Sigma-Aldrich (St. Louis, Mo.). $^1$H NMR spectra were obtained with a Varian Gemini 300 spectrometer using CDCl$_3$, CD$_3$OD or DMSO-d$_6$ as solvents. The chemical shifts are expressed as ppm downfield from TMS. Melting points were determined with a Thomas-Hoover apparatus (A. H. Thomas Co.) and are uncorrected.

Purity of compounds was checked using a Hewlett-Packard 1100 HPLC equipped with a Luna 5μ RP-C18(2) analytical column (250×4.6 mm; Phenomenex, Torrance, Calif.). System A: linear gradient solvent system: H$_2$O/CH$_3$CN from 95/5 to 20/80 in 20 min; the flow rate was 1 mL/min. System B: linear gradient solvent system: 5 mM TBAP/CH$_3$CN from 80/20 to 20/80 in 20 min, then isocratic for 2 min; the flow rate was 1 mL/min. Peaks were detected by UV absorption with a diode array detector. All derivatives tested for biological activity showed >96% purity in the HPLC systems.

TLC analysis was carried out on aluminum sheets precoated with silica gel F$_{254}$ (0.2 mm) from Aldrich. Low-resolution mass spectrometry was performed with a JEOL SX102 spectrometer with 6-kV Xe atoms following desorption from a glycerol matrix or on LC/MS 1100 Agilent, 1100 MSD, with Waters Atlantis Column C18. High resolution mass measurements were performed on a proteomics optimized Q-TOF-2 (Micromass-Waters) using external calibration using polyalanine. Observed mass accuracies are those expected based on known instruments performance as well as the trends in observed masses of standard compounds measured at intervals during the series of measurements. Reported masses are observed masses uncorrected for this time dependent drift in mass accuracy.

Bromomethyl-2-chloro-5-iodobenzene (60). A mixture of 2-chloro-5-iodo-toluene (0.5 g, 1.98 mmol), N-bromosuccinimide (0.422 g, 2.35 mmol) and benzoyl peroxide (21.5 mg, 0.089 mmol) in dry CCl$_4$ (5 mL) was stirred and heated to reflux for 3 h. After cooling, the mixture-was filtered, and the red filtrate was washed with a saturated solution of sodium thiosulfate (2×10 mL). The organic phase was washed with brine, dried over Na$_2$SO$_4$, filtered and concentrated. The residue was purified by flash chromatography on silica gel (petroleum ether), to give 60 as a white solid (361 mg, 55%). $^1$H NMR (CDCl$_3$, 300 MHz) δ 7.76 (d, J=2.4 Hz, 1H), 7.56 (dd, J=8.7, 2.1 Hz, 1H), 7.12 (d, J=8.4 Hz, 1H), 4.49 (s, 2H). MS (m/e) (positive FAB) 332.1 (M+H)$^+$, m.p. 94-95° C.

N-(2-Chloro-5-iodobenzyl)phthalimide (63). Bromomethyl-2-chloro-5-iodo-benzene (60) (400 mg, 1.2 mmol) and potassium phthalimide (693 mg, 1.5 mmol) were stirred in dry DMF (20 mL) and heated to 80° C. for 3 hours. After cooling, the suspension was filtered and concentrated in vacuo, and the residue was partitioned between water (30 mL) and Et$_2$O (30 mL). The aqueous phase was extracted with ether (20 mL×3). The combined organic phases were dried over Na$_2$SO$_4$, filtered and concentrated to give 63 (455 mg, 95%). $^1$H NMR (CDCl$_3$, 300 MHz) δ 7.92-7.86 (m, 2H), 7.78-7.75 (m, 2H), 7.54-7:50 (m, 2H), 7.10 (d, J=8.4 Hz, 1H), 4.93 (s, 2H). MS (m/e) (API-ES) 397.9 (M)$^+$, m.p. 134-136° C.

N-(2,5-Dichlorobenzyl phthalimide) (62). Compound 62 was prepared by the same procedure as compound 63. $^1$H NMR (CDCl$_3$, 300 MHz) δ 7.93-7.89 (m, 2H), 7.79-7.75 (m, 2H), 7.32 (d, J=6 Hz, 1H), 7.21-7.16 (m, 2H), 4.96 (s, 2H). MS (m/e) (API-ES) 306.12 (M)$^+$, m.p. 145-146° C.

2-Chloro-5-iodo-benzylamine hydrochloride (65). Compound 63 (350 mg, 0.88 mmol) was dissolved in dry EtOH (15 mL) and hydrazine (0.1 mL) was added. The stirred mixture was refluxed for 24 h, cooled and the EtOH evaporated. The residue was dissolved in Et$_2$O (3 mL) and treated with HCl/Et$_2$O. The precipitated hydrochloride salt was filtered and triturated with dry Et$_2$O (3×2 mL), obtaining 200 mg of product (yield 75%). $^1$H NMR (D$_2$O, 300 MHz) δ 7.88 (s, 1H), 7.80 (dd, J=8.4, 1.8 Hz, 1H), 7.31 (d, J=7.8 Hz, 1H), 4.27 (s, 2H). MS (m/e) (positive FAB) 268.1 (M−Cl)$^+$, m.p. 207-210° C.

2,5-Dichlorobenzylamine hydrochloride (64). 64 was prepared by the same procedure as compound 65. $^1$H NMR (D$_2$O, 300 MHz) δ 7.59-7.47(m, 3H), 4.33 (s, 2H). MS (m/e) (positive FAB) 177.1. (M−Cl)$^+$, m.p. >220° C.

2-Methoxy-5-iodobenzaldehyde (67). 5-Iodo-salicylaldehyde (1.0 g, 4.0 mmol) was dissolved in DMF (10 mL) and to the stirred solution K$_2$CO$_3$ (0.828 g, 6.0 mmol) and CH$_3$I (1.14 g, 8.0 mmol) were added. The mixture was stirred at room temperature overnight. The suspension was concentrated in vacuo, and the residue was partitioned between water (30 mL) and Et$_2$O (30 mL). The aqueous phase was separated and extracted with ether (20 mL×2). The combined organic phases were dried over Na$_2$SO$_4$, filtered and concentrated to give 67 (1.02 g, 98%). $^1$H NMR (CDCl$_3$, 300 MHz) δ 10.34(s, 1H), 7.82-7.78 (m, 1H), 7.26 (s, 1H), 6.78 (d, J=8.7 Hz, 1H), 3.91 (s, 3H). MS (m/e) (positive FAB) 262.1 (M+H)$^+$, m.p. 140-142° C.

2-Methoxy-5-iodobenzylamine (68). To a stirred solution of 67 (500 mg, 1.9 mmol) and ammonium acetate (1.5 g, 19.4 mmol) in dry methanol (6 mL) NaCNBH$_3$ (170 mg, 2.66 mmol) was added in one portion. The resulting mixture was stirred at room temperature for 48 h. Concentrated HCl was added until pH<2. The methanol was evaporated and the resulting white residue was dissolved in water (10 mL) and washed with Et$_2$O (2×10 mL). The aqueous phase was then basified with aqueous KOH (45%), saturated with NaCl and extracted with CH$_2$Cl$_2$ (10 mL×4). The combined organic phases were dried over Na$_2$SO$_4$, filtered and concentrated to give 68 as a yellow oil (200 mg, 40%). $^1$H NMR (CDCl$_3$, 300 MHz) δ 7.55-7.45 (m, 2H), 6.46-6.58 (m, 1H), 3.82-3.72 (m, 5H), 1.63 (br s, 2H). MS (m/e) (positive FAB) 264.1 (M+H)$^+$, m.p. 95-97° C.

3-(3-Hydroxypropynyl)-benzylamine (72). Cuprous iodide (1.06 mg, 0.0056 mmol) was added to a mixture of (PPh$_3$)$_2$PdCl$_2$ (7.84 mg, 0.011 mmol) and 3-iodobenzylamine (262 mg, 1.12 mmol) in dry diethylamine (7 mL) under a nitrogen atmosphere. Then a solution of propargyl alcohol (41.2 μL, 0.73 mmol) in dry diethylamine (3 mL) was added. The resulting solution was stirred at room temperature for 3 h. The solvent was concentrated in vacuo and the residue was partitioned between water (20 mL) and CHCl$_3$ (20 mL). The aqueous phase was separated and extracted with CHCl$_3$ (20 mL×2). The combined organic phases were dried over Na$_2$SO$_4$, filtered and concentrated. The residue was purified by PTLC (chloroform/methanol 9:1) to give 72 (106 mg, 90% yield). $^1$H NMR (CDCl$_3$, 300 MHz) δ 7.39-7.26 (m, 4H), 4.48 (s, 2H), 3.85 (s, 2H), 1.73 (br s,22H). MS (m/e) (positive FAB) 162.1 (M+H)$^+$.

2-Chloro-5-(3-hydroxypropynyl)-benzylamine (73). Compound 73 was prepared by the same procedure as compound 72, using compound 65 as starting material. $^1$H NMR (CDCl$_3$, 300 MHz) δ 7.48(s, $^1$H) 7.28-7.25(m, 3H), 4.48 (s, 2H), 3.92 (s, 2H), 1.92 (br s, 2H). MS (m/e) (positive FAB) 196.1 (M+H)$^+$.

5-Chloro-2-(methoxybenzyl)-benzamide (75). 5-Chloro-2-hydroxy-benzamide (1.5 g, 8.7 mmol) was dissolved in DMF (120 mL) and to the stirred solution K$_2$CO$_3$ (1.38 g, 10 mmol) and benzylbromide (1.71 g, 10 mmol) were added. The mixture was stirred at room temperature overnight. The suspension was concentrated in vacuo, and the residue was partitioned between water (30 mL) and Et$_2$O (30 mL). The aqueous phase was separated and extracted with ether (20 mL×2). The combined organic phases were dried over Na$_2$SO$_4$, filtered and concentrated. The residue was purified by flash chromatography on silica gel (petroleum ether/ethyl acetate 90/10), to give 75 as a white solid (2.15 g, 95%). $^1$H NMR (CDCl$_3$, 300 MHz) δ8.20 (d, J=3 Hz, 1H), 7.67 (br s, 1H), δ7.44-7.38(m, 6H), 7.99 (d, J=9 Hz, 1H), 5.85 (br s, 1H), 5.17 (s, 2H). MS (m/e) (positive FAB) 262.1 (M+H)$^+$. m.p. 110-112° C.

5-Chloro-2-(methoxybenzyl)-benzylamine hydrochloride (76). To a suspension of LiAlH$_4$ (280 mg, 7.37 mmol) in dry tetrahydrofuran (20 mL) under nitrogen atmosphere, a solution of 75 (1.0 g, 3.83 mmol) in THF (10 mL) was added and the mixture was refluxed for 3 h. After cooling, the excess of LiAlH$_4$ was destroyed with a saturated solution of sodium sulfate. The mixture was filtered on MgSO$_4$ and the filtrate concentrated in vacuo. The residue was partitioned between water (30 mL) and CH$_2$Cl$_2$ (30 mL). The aqueous-phase was separated and extracted with CH$_2$Cl$_2$ (20 mL×2). The combined organic phases were dried over Na$_2$SO$_4$, filtered and concentrated. The residue was dissolved in Et$_2$O (5 mL) and treated with HCl/Et$_2$O. The precipitated hydrochloride salt was filtered and triturated with dry Et$_2$O (3×2 mL), obtaining 760 mg of product (yield 70%). $^1$H NMR (CD$_3$OD, 300 MHz) δ 7.50-7.33 (m, 7H), 7.15 (d, J=9 Hz, 1H), 5.22 (s, 2H), 4.13 (s, 2H). MS (m/e) (API-ES) 248 (M−Cl)$^+$. m.p 119-121° C.

5-Chloro-2-hydroxy-benzylamine (77). To a suspension of LiAlH$_4$ (437 mg, 11.5 mmol) in dry tetrahydrofuran (30 mL) under nitrogen atmosphere, a solution of 5-chloro-2-hydroxybenzamide 74 (1.5 g, 5.7 mmol) in THF (10 mL) was added and the mixture was refluxed for 3 h. After cooling, the excess of LiAlH$_4$ was destroyed with a saturated solution of sodium sulfate. The mixture was filtered on MgSO$_4$ and the filtrate concentrated in vacuo. The residue was partitioned between water (30 mL) and CH$_2$Cl$_2$ (30 mL). The aqueous phase was separated and extracted with CH$_2$Cl$_2$ (20 mL×2). The combined organic phases were dried over Na$_2$SO$_4$, filtered and concentrated. The obtained solid was recrystallized from ethanol obtaining 787 mg of pure product (yield 88%). $^1$H NMR (CDCl$_3$, 300 MHz) δ 7.10 (dd, J=6.6, 2.7 Hz, 1H), 6.94 (d, J=2.4 Hz, 1H), 6.76 (d, J=8.7 Hz, 1H), 4.10 (br s, 2H), 1.61 (br s, 2H). MS (m/e) (API-ES) 158 (M+H)$^+$, m.p. 160-162° C.

(5-Chloro-2-hydroxy-benzyl)-carbamic acid tert-butyl ester (78). Compound 77 (300 mg, 1.9 mmol) was dissolved in a dry solution at 10% of triethylamine in MeOH (12 mL) and a solution of di-t-butylcarbamate (1 M in THF, 3.8 mL, 3.8 mmol) was added. The solution was stirred at 45° C. for 1 h and then concentrated in vacuo. The residue was purified by flash chromatography on silica gel (petroleum ether/ethyl acetate 90/10), to give 78 as a white solid (350 mg, 80%). $^1$H NMR (CDCl$_3$, 300 MHz) δ9.02 (br s, 1H), δ 7.1.(dd, J=8.4, 2.4 Hz, 1H), 6.94 (d, J=2.4 Hz, 2H), 6.76 (d, J=8.7 Hz, 1H), 5.23 (br s, 1H), 4.17 (d, J=6.9 Hz, 2H), 1.44 (s, 9H). MS (m/e) (API-ES) 258 (M+H)$^+$, m.p 124-126° C.

(2-Carbamoylmethoxy-5-chloro-benzyl)-carbamic acid tert-butyl ester (79). 5-Chloro-2-hydroxy-benzyl)-carbamic acid tert-butyl ester 78 (210 mg, 0.8 mmol) was dissolved in DMF (6 mL) and to the stirred solution K$_2$CO$_3$ (13.8 mg, 1 mmol) and 2-bromoacetamide (138 mg, 1 mmol) were added. The mixture was stirred at room temperature overnight. The suspension was concentrated in vacuo, and the residue was partitioned between water (20 mL) and CH$_2$Cl$_2$ (10 mL). The aqueous phase was separated and extracted with CH$_2$Cl$_2$ (20 mL×2). The combined organic phases were dried over Na$_2$SO$_4$, filtered and concentrated. The residue was purified by flash chromatography on silica gel (petroleum ether/ethyl acetate 80/20), to give 79 as a white solid (226 mg, 90%). $^1$H NMR (CDCl$_3$, 300 MHz) δ7.88 (br s, 1H), 7.27-7.18 (m, 2H), 6.76 (d, J=8.7 Hz, 1H), 5.54 (br s, 1H), 4.78( br s, 1H), 4.47 (s, 1H), 4.36 (d, J=6.3 Hz), 1.43 (s, 9H). MS (m/e) (API-ES) 337.0 (MNa)$^+$. m.p 142-143° C.

5-Chloro-2-(aminocarbonyl-methyloxy)-benzylamine (80). Compound 79 (200 mg, 0.63 mmol) was treated with a solution at 15% of TFA in CH$_2$Cl$_2$ at room temperature for 45 min. The solution was concentrated in vacuo and water (10 mL) was added. The aqueous phase was washed with Et$_2$O, basified with aqueous 2N NaOH, and extracted with CHCl$_3$ (10 mL×3) obtaining 130 mg of a white solid (80) (yield 96%). $^1$H NMR (CDCl$_3$, 300 MHz) δ8.37 (br s, 1H), 7.29-7.22 (m, 2H), 6.82 (d, J=9.3 Hz, 1H), 5.44 (br s, 1H), 3.8(s, 2H), 3.89 (s, 2H). MS (m/e) (API-ES) 215 (M+H)$^+$, m.p. 135-137° C.

General procedure for the synthesis of compounds 39-54 and 16-33. (1'S,2'R,3'S,4'S,5'S)-4'-[6-(3-Bromobenzylamino)-2-chloro-purin-9-yl]-2',3'-O-isopropylidene-bicyclo[3.1.0]hexane-1'-carboxylic acid ethyl ester (39). 3-Bromobenzylamine hydrochloride (122 mg, 0.55 mml) was added to a solution of 117 (50 mg, 0.12 mmol) and triethylamine (1 mL) in methanol (3 mL). The mixture was stirred at room temperature for 3 h. It was concentrated in vacuo to dryness and the residue was purified by PTLC (chloroform/methanol 15:1) to give 39 (55 mg, 82%). $^1$H NMR(CDCl$_3$, 300 MHz) δ 7.70 (s, 1H), 7.52 (s, 1H), 7.31-7.18 (m, 2H), 6.18 (br s, 1H), 5.87 (d, J=7.2 Hz, 1H), 4.85-4.71 (m, 4H), 4.32-4.16 (m, 2H), 2.24-2.19 (m, 1H), 1.75-1.70(m, 1H),-1.55-1.49 (m, 4H), 1.35(t, J=7.8, 3H), 1.29 (s, 3H). MS (m/e) (positive FAB) 564.1 (M+H)$^+$.

(1'S,2'R,3'S,4'S,5'S)-4'-[6-(3-Fluorobenzylamino)-2-chloro-purin-9-yl]-2',3'-O-isopropylidene-bicyclo[3.1.0]hexane-1'-carboxylic acid ethyl ester (40). $^1$H NMR (CDCl$_3$, 300 MHz) δ7.65 (s, 1H), 7.34-7.26 (m, 1H), 7.15-6.57 (m, 3H), 6.22 (br s, 1H), 5.87 (d, J=8.4 Hz, 1H), 4.85 (br s, 3H), 4.72 (d, J=7.2 Hz, 1H), 4.34-4.17 (m, 2H), 3.48 (d, J=5.1 Hz, 1H), 2.24-2.18 (m, 1H), 1.75-1.69 (m, 1H), 1.55 (s, 3H), 1.34 (t, J=7.8, 3H), 1.29 (s, 3H). MS (m/e) (ASI-ES) 502.1 (M+H)$^+$.

(1'S,2'R,3'S,4'S,5'S)-4'-[6-(3-Chlorobenzylamino)-2-chloro-purin-9-yl]-2',3'-O-isopropylidene-bicyclo[3.1.0]hexane-1'-carboxylic acid ethyl ester (41). $^1$H NMR (CDCl$_3$, 300 MHz) $^1$H NMR (CDCl$_3$, 300 MHz) δ 1.20-1.42 (m, 3H), 1.44-1.83 (m, 8H), 2.20-2.26 (m, 1H), 4.05-4.38 (m, 2H), 4.82-4.94 (m, 3H), 5.38 (d, J=4.5 Hz, 1H), 5.86 (d, J=8 Hz, 1H), 6.15 (br s, 1H), 7.21-7.40 (m, 4H), 7.67 (s, 1H), MS (m/e) (positive-FAB) 518.1 (M+1)$^+$.

(1'S,2'R,3'S,4'S,5'S)-4'-[6-(2,5-Dichlorobenzylamino)-2-chloro-purin-9-yl]-2',3'-O-isopropylidene-bicyclo[3.1.0]hexane-1'-carboxylic acid ethyl ester (42). $^1$H NMR (CDCl$_3$, 300 MHz) δ7.68 (s, 1H), 7.51 (s, 1H), 7.33 (d, J=8.7 Hz, 1H), 7.23-7.19 (m, 1H), 6.28 (br s, 1H), 5.57 (d, J=8.4 Hz, 1H), 4.85 (br s, 3H), 4.7 (d, J=6 Hz, 1H), 4.32-4.16 (m, 2H), 2.21-2.19 (m, 1H), 1.75-1.70 (m, 1H), 1.55-1.50 (m, 4H), 1.35 (t, J=7.8 Hz, 3H), 1.28 (s, 3H). MS (m/e) (positive FAB) 554.1 (M+H)$^+$.

(1'S,2'R,3'S,4'S,5'S)-4'-[6-(2-Chloro-5-iodo-benzylamino)-2-chloro-purin-9-yl]-2',3'-O-isopropylidene-bicyclo[3.1.0]hexane-1'-carboxylic acid ethyl ester (43). $^1$H NMR (CDCl$_3$, 300 MHz) δ7.85 (s, 1H), 7.67 (s, 1H), 7.57-7.53 (dd, J=8.1, 1.8 Hz, 1H), 7.12 (d, J=8.4 Hz, 1H), 6.32 (br s, 1H), 5.58 (d, J=8.4 Hz, 1H), 4.85 (br s, 3H), 4.73 (d, J=6 Hz, 1H), 4.33-4.14 (m, 2H), 2.24-2.19 (m, 1H), 1.75-1.70 (m, 1H), 1.55-1.50 (m, 4H), 1.35 (t, J=7.8 Hz, 3H), 1.29 (s, 3H). MS (m/e) (positive FAB) 644.1 (M)$^+$.

(1'S,2'R,3'S,4'S,5'S)-4'-[6-(5-Chloro-2-mehoxybenzylamino)-2-chloro-purin-9-yl]-2',3'-isopropylidene-bicyclo[3.1.0]hexane-1'-carboxylic acid ethyl ester (44). $^1$H NMR (CDCl$_3$, 300 MHz) δ 1.11-1.23 (m, 6H), 1.36-1.81 (m, 5H), 1.09-1.23 (m, 1H), 3.86 (s, 3H), 4.08-4.41 (m, 2H), 4.60-4.83 (m, 3H), 5.30 (s, 1H), 5.85 (d, J=4.5 Hz, 1H), 6.21-6.29 (m, 1H), 6.81 (d, J=12 Hz, 1H), 7.21-7.42 (m, 3H), 7:67 (br s, 1H), MS (m/e) (positive-FAB) 548.1 (M+1)$^+$.

(1'S,2'R,3'S,4'S,5'S)-4'-[6-(5-Chloro-2-(aminoycarbonyl-methyloxy)-benzylamino)-2-chloro-purin-9-yl]-2',3'-O-isopropylidene-bicyclo[3.1.0]hexane-1'-carboxylic acid ethyl ester (45). $^1$H NMR (CDCl$_3$, 300 MHz) δ7.66 (s, 1H), 7.36 (s, 1H), 7.30-7.27 (m, 1H), 7.07-7.05 (m, 1H), 6.81 (d, J=8.7 Hz, 1H), 6.12 (br s, 1H), 5.85 (d, J=8.4 Hz, 1H), 5.65 (br s, 1H), 5.01-4.85 (br s,.3H), 4.73 (d, J=6 Hz, 1H), 4.50 (s, 1H), 4.34-4.21 (m, 2H), 2.23-2.18 (m, 1H), 1.74-1.69 (m, 1H), 1.55-1.50 (m, 4H), 1.34 (t, J=7.8 Hz, 3H), 1.29 (s, 3H). MS (m/e) (API-ES) 591.1 (M+H)$^+$.

(1'S,2'R,3'S,4'S,5'S)-4'-[6-(5-Chloro-2-benzyloxy-benzylamino)-2-benzyloxy-benzylamino)-2chloro-purin-9-yl]-2',3'-O-isopropylidene-bicyclo[3.1.0]hexane-1'-carboxylic acid ethyl ester (46). $^1$H NMR (CDCl$_3$, 300 MHz) δ 7.62 (s, 1H), 7.39-7.30 (m, 6H), 7.18 (dd, J=8.7, 2.7 Hz, 1H), 6.86 (d, J=8.7 Hz, 1H), 6.33 (br s, 1H), 5.86 (d, J=8.4 Hz, 1H), 5.81 (s, 2H), 4.85 (br s, 3H), 4.70 (d, J=6 Hz, 1H), 4.32-4.19 (m, 2H), 2.23-2.18 (m, 1H), 1.74-1.69 (m, 1H), 1.55-1.50 (m, 4H), 1.34 (t, J=7.8 Hz, 3H), 1.28 (s, 3H). MS (m/e) (positive FAB) 624.2 (M+H)$^+$.

(1'S,2'R,3'S,4'S,5'S)-4'-[6-(5-Iodo-2-methoxy-benzylamino)-2-chloro-purin-9-yl]-2',3'-O-isopropylidene-bicyclo[3.1.0]hexane-1'-carboxylic acid ethyl ester (47). $^1$H NMR (CDCl$_3$, 300 MHz) δ 7.71-7.64 (m, 2H), 7.57-7.53,(m, 2H), 6.21 (br s, 1H), 5.57 (d, J=8.4 Hz, 1H), 4.84 (s, 2H), 4.75-4.69 (m, 2H), 4.32-4.20.(m, 2H), 3.85 (s, 3H), 2.23-2.18 (m, 1H), 1.74-1.69 (m, 1H), 1.55-1.50 (m, 4H), 1:34 (t, J=7.8 Hz, 3H), 1.28 (s, 3H). MS (m/e) (positive FAB) 640.1 (M+H)$^+$.

(1'S,2'R,3'S,4'S,5'S)-4'-[6-(2,5-Dimethoxy-benzylamino)-2-chloro-purin-9-yl]-2',3'-O-isopropylidene-bicyclo[3.1.0]hexane-1'-carboxylic acid ethyl ester (48). $^1$H NMR (CDCl$_3$, 300 MHz) δ 7.62 (s, 1H), 7.03 (s, 1H), 7.79 (s, 2H), 6.39 (br s, 1H), 5.57 (d, J=8.4 Hz, 1H), 4.83-4.69 (m, 4H), 4.31-4.19 (m, 2H), 3.83 (s, 3H), 3.76 (s, 3H), 2.21-2.17 (m, 1H), 1.73-1:68 (m, 1H), 1.55-1.49 (m, 4H), 1.35.(t, J=7.8 Hz, 3H), 1.28 (s, 3H). MS (m/e) (positive FAB) 544.2 (M+H)$^+$.

(1'S,2'R,3'S,4'S,5'S)-4'-[6-(2-Methyl-benzylamino)-2-chloro-purin-9-yl]-2',3'-O-isopropylidene-bicyclo[3.1.0]hexane-1'-carboxylic acid ethyl ester (49). $^1$H NMR (CDCl$_3$, 300 MHz) δ 7.58 (s, 1H), 7.32 (d, J=6.9 Hz, 1H), 7.23-7.16 (m, 2H), 6.07 (br s, 1H), 5.57 (d, J=8.4 Hz, 1H), 4.83-4.69 (m, 4H), 4.32-4.16 (m, 2H), 2.37 (s, 3H), 2.23-2.18 (m, 1H), 1.74-1.69 (m, 1H), 1.55-1.50 (m, 4H), 1.35 (t, J=7.8 Hz, 3H), 1.28 (s, 3H). MS (m/e) (positive FAB) 498.3 (M)$^+$.

(1'S,2'R,3'S,4'S,5'S)-4'-[6-(3-Methyl-benzylamino)-2-chloro-purin-9-yl]-2',3'-O-isopropylidene-bicyclo[3.1.0]hexane-1'-carboxylic acid ethyl ester (50). $^1$H NMR,(CDCl$_3$, 300 MHz) δ7.56 (s, 1H), 7.26-7.09 (m, 4H), 6.27 (br s, 1H), 5.87 (d, J=8.4 Hz, 1H), 4.83-4.71 (m, 4H), 4.30-4.20 (m, 2H), 2.33 (s, 3H), 2.22-2.17 (m, 1H), 1.74-1.69 (m, 1H), 1.55-1.50 (m, 4H), 1.34 (t, J=7.8 Hz, 3H), 1.28 (s, 3H). MS (m/e) (positive FAB) 498.3 (M)$^+$.

(1'S,2'R,3'S,4'S,5'S)-4'-[6-(3-(3-Hydroxypropynyl)-benzylamino)-2-chloro-purin-9-yl]-2',3'-O-isopropylidene-bicyclo[3.1.0]hexane-1'-carboxylic acid ethyl ester (51). $^1$H NMR (CDCl$_3$, 300 MHz) δ 7.56 (s, 1H), 7.38 (s, 1H), 7.34-7.26 (m, 2H), 6.73 (br s, 1H), 5.87 (d, J=8.4 Hz, 1H), 4.82-4.70 (m, 4H), 4.46 (d, J=6 Hz, 2H), 4.32-4.20 (m, 2H), 2.41 (br s, 1H), 2.23-2.18 (m, 1H), 1.75-1.70 (m, 1H), 1.55-1.50 (m, 4H), 1.35 (t, J=7.8 Hz, 3H), 1.28 (s, 3H). MS (m/e) (positive FAB) 538.2 (M+1)$^+$.

(1'S,2'R,3'S,4'S,5'S)-4'-[6-(2-Chloro-5-(3-hydroxypropynyl)-benzylamino)-2-chloro-purin-9-yl]-2',3'-O-isopropylidene-bicyclo[3.1.0]hexane-1'-carboxylic acid ethyl ester (52). $^1$H NMR (CDCl$_3$, 300 MHz) δ7.63(s, 1H), 7.48 (s, 1H), 7.32-7.22 (m, 2H), 6.63 (br s, 1H), 5.87 (d, J=8.4 Hz, 1H), 4.88-4.79 (m, 4H), 4.71 (d, J=4.8 Hz, 1H), 4.45 (d, J=6 Hz, 2H), 4.32-4.19 (m, 2H), 2.35 (s, 3H), 2.23-2.18 (m, 1H), 1.75-1.68 (m, 1H), 1.55 (s, 3H), 1.35 (t, J=7.8 Hz, 3H), 1.28 (s, 3H). MS (m/e) (positive FAB) 572.1 (M+1)$^+$.

(1'S,2'R,3'S,4'S,5'S)-4'-[6-(4-Amino-benzylamino)-2-chloro-purin-9-yl]-2',3'-O-isopropylidene-bicyclo[3.1.0]hexane-1'-carboxylic acid ethyl ester (53). $^1$H NMR (CDCl$_3$, 300 MHz) δ 7.59(s, 1H), 7.17(d, J=8.1 Hz, 2H), 6.65 (d, J=8.1 Hz, 2H), 6.12 (br s, 1H), 5.87 (d, J=8.4 Hz, 1H), 4.84 (s, 1H), 4.73-4.58 (m, 3H), 4.33-4.20 (m, 2H), 3.17 (br s, 2H), 2.26-2.18 (m, 1H), 1.75-1.69 (m, 1H), 1.56-1.50 (m, 4H), 1.35 (t, J=7.8 Hz, 3H), 1.28 (s, 3H). MS (m/e) (positive FAB) 499.2 (M+1)$^+$.

(1'S,2'R,3'S,4'S,5'S)-4'-[6-(3-Pyridylmethylamino)-2-chloro-purin-9yl]-2',3'-O-isopropylidene-bicyclo[3.1.0]hexane-1'-carboxylic acid ethyl ester (54). $^1$H NMR (CDCl$_3$, 300 MHz) δ 8.66 (br s, 1H), 8.54(br s, 1H), 7.73 (d, J=6.6 Hz, 1H), 7.67 (s, 1H), 7.34-7.27 (m, 1H) 6.26 (br s, 1H), 5.88.(d, J=8.4 Hz, 1H), 4.85 (br s, 3H), 4.72 (d, J=4.8 Hz, 1H), 4.45 (d, J=6 Hz, 2H), 4.33-4.20 (m, 2H), 2.24-2.18 (m, 1H), 1.75-1.70 (m, 2H), 1.56 (s, 3H), 1.35 (t, J=7.8 Hz, 3H), 1.28 (s, 3H). MS (m/e) (positive FAB) 485.2 (M+1)$^+$.

(1'S,2'R,3'S,4'S,5'S)-4'-[6-(3-Bromobenzylamino)-2-chloro-purin-9-yl]-2',3'-dihydroxy-bicyclo[3.1.0]hexane-1'-carboxylic acid methyl amide (17). The ester 39 (45 mg, 0.08 mmol) was dissolved in methanol (3 mL) and treated with an aqueous solution of methylamine (1 mL, 40%). This mixture was stirred at room temperature overnight, then the solvent was-evaporated to dryness, and the white residue was purified by PTLC (chloroform/methanol 9:1) to give the uronamide 17 (19.6 mg, 40%). $^1$H NMR (CDCl$_3$, 300 MHz) δ 7.68 (s, 1H), 7.51 (s, 1H), 7.31-7.19 (m, 2H), 6.83 (br s, 1H), 6.30 (br s, 1H), 5.67 (d, J=6.9 Hz, 1H), 4.79-4.78 (m, 4H), 2.92 (d, J=4.5 Hz, 3H), 2.07-2.02 (m, 1H), 1.70-1.65 (m, 2H), 1.55 (s, 3H), 1.27 (s, 3H). MS (m/e) (positive FAB) 549.1 (M+1)$^+$.

The above intermediate (18 mg, 0.03 mmol) was treated with a solution of trifluoroacetic acid in MeOH (5 mL, 10%) and H$_2$O (0.5 mL) and the mixture was heated at 70° C. for 3 h. The solution was cooled and the solvent removed to dryness by coevaporation with toluene in vacuo. The white residue was purified by PTLC (chloroform/methanol 9:1) to give the final product 17 (10 mg, 70%/o). $^1$H NMR (CDCl$_3$, 300 MHz) δ7.83 (s, 1H), 7.52-7.50 (m, 1H), 7.43-7.39 (m, 1H), 7.31-7.17 (m, 2H), 6.90 (br s, 1H), 6.63 (br s, 1H), 4.95-4.78 (m, 5H), 4.07 (d, J=6Hz, 1H), 2.90 (d, J=5.1 Hz, 3H), 2.24-2.19 (m, 1H), 1.72 (br s, 2H), 1.36-1.32 (m, 1H). HRMS (M+1)$^+$: calculated 507.0547, found 507.0686. HPLC (System A) 20.4 min (99%) (System B), 12.9 min (99%).

(1'S,2'R,3'S,4'S,5'S)-4'-[6-(3-Chlorobenzylamino)-2-chloro-purin-9-yl]-2',3'-dihydroxy-bicyclo[3.1.0]hexane-1'-carboxylic acid methylamide (18). $^1$H NMR (CDCl$_3$, 300 MHz) δ 1.17-1.39 (m, 1H), 1.45-1.61 (m, 1H), 2.01-2.09 (m, 1H), 2.81 (d, J=4.5 Hz, 1H), 3.91-4.08 (m, 2H), 4.78-5.05 (m, 5H), 6.71 (br s, 1H), 7.04 (br s, 1H), 7.11-7.29 (m, 4H), 7.74 (s, 1H), HRMS (M+1)$^+$: calcd 463.0974, Found 463.1052. HPLC (System A) 14.8 min (99%) (System B), 12.5 min (99%).

(1'S,2'R,3'S,4'S,5'S)-4'-[6-(3-Fluorobenzylamino)-2-chloro-purin-9-yl]-2',3'-dihydroxy-bicyclo[3.1.0]hexane-1'-carboxylic acid methylamide (19) $^1$HNMR (CDCl$_3$, 300 MHz), 7.84 (s, 1H), 7.34-7.26 (m, 1H), 7.15-6.95 (m, 3H), 6.86 (br s, 1H), 6.56 (br s, 1H), 4.88-4.80 (m, 4H), 4.08 (d, J=6Hz, 1H), 2.91 (d, J=5.1 Hz, 3H), 2.27-2.23 (m, 1H), 1.78 (br s, 2H), 1.36-1.32 (m, 1H). HRMS (M+1)$^+$: calculated 447.1347, found 447.1378. HPLC (System A) 13.6 min (99%) (System B), 16.8 min (98%).

(1'S,2'R,3'S,4'S,5'S)-4'-[6-(2,5-Dichlorobenzylamino)-2-chloro-purin-9-yl]-2',3'-dihydroxy-bicyclo[3.1.0]hexane-1'-carboxylic acid methyl amide (20). $^1$H NMR (CDCl$_3$, 300 MHz) δ 7.94 (s, 1H), 7.60 (s, 1H), 7.43 (d, J=8.4 Hz, 1H), 7.34-7.30 (m, 1H), 7.04 (br s, 1H), 6.61 (br s, 1H), 5.12-4.92

(m, 1H), 431-4.22 (m, 1H), 3.03 (d, J=5.1 Hz, 3H), 2.31-2.27 (m, 1H), 1.54-1.46 (m, 1H). HRMS (M+1)$^+$: calculated 497.0662, found 497.0797. HPLC (System A) 17.2 min (98%) (System B), 13.8 min (97%).

(1'S,2'R,3'S,4'S,5'S)-4'-[6-(2-Chloro-5-iodo-benzylamino)-2-chloro-purin-9-yl]-2',3'-dihydroxy-bicyclo[3.1.0]hexane-1'-carboxylic acid methylamide (21). $^1$H NMR (CDCl$_3$, 300 MHz) δ 7.83 (m, 2H), 7.55 (d, J=8.4 Hz, 1H), 7.12 (d, J=8.4 Hz, 1H), 6.86 (br s, 1H), 6.43 (br s, 1H), 4.96-4.80 (m, 3H), 4.13-4.08 (m, 2H), 2.91 (d, J=5.1 Hz, 3H), 2.24-2.19 (m, 1H), 1.72 (br s, 2H), 1.36-1.32 (m, 1H). HRMS (M+1)$^+$: calculated 589.0018, found 589.0250. HPLC (System A) 16.6 min (98%) (System B), 14.6 min (97%).

(1'S,2'R,3'S,4'S,5'S)-4'-[6-(5-Chloro-2-methoxy-benzylamino)-2-chloro-purin-9-yl]-2',3'-dihydroxy-bicyclo[3.1.0]hexane-1'-carboxylic acid methylamide (22). $^1$H NMR (CDCl$_3$, 300 MHz) δ 1.12-1.42 (m, 2H), 2.21-2.27 (m, 1H), 2.91 (d, J=4.8 Hz, 3H), 3.86 (s, 3H), 4.01-4.22 (m, 2H), 4.65-4.83 (m, 3H), 4.95-5.01 (m, 1H), 6.42 (br s, 1H), 6.81 (d, J=12 Hz, 1H), 6.95 (br s, 1H), 7.21-7.43 (m, 3H), 7.81 (s, 1H). HRMS (M+1)$^+$: calculated 493.1080, found 493.1158. HPLC (System A) 15.1 min (99%) (System B), 12.9 min (98%).

(1'S,2'R,3'S,4'S,5'S)-4'-[6-(5-Chloro-2-(aminocarbonylmethyloxy)-benzylamino)-2-chloro-purin-9-yl]-2',3'-dihydroxy-bicyclo[3.1.0]hexane-1'-carboxylic acid methylamide (23). $^1$H NMR (CD$_3$OD, 300 MHz) δ 8.04 (s, 1H), 7.38 (s, 1H), 7.25 (d, J=8.4 Hz, 1H), 6.94 (d, J=8.4 Hz, 1H), 5.07 (d, J=6.3 Hz, 1H) 4.59 (s, 2H), 4.99 (d, J=6.3 Hz, 1H) 2.99-2.68 (m, 5H), 2.05-2.02 (m, 1H), 1.38-1.34 (m, 1H). HPLC (System A) 12.3 min (97%) (System B), 9.1 min (98%).

(1'S,2'R,3'S,4'S,5'S)-4'-[6-(5-Chloro-2-benzyloxy-benzylamino)-2-chloro-purin-9-yl]-2',3'-dihydroxy-bicyclo[3.1.0]hexane-1'-carboxylic acid methylamide (24). $^1$H NMR (CDCl$_3$, 300 MHz) δ7.80 (s, 1H), 7.41-7.31 (m, 6H), 7.18 (dd, J=8.7, 2.7 Hz, 1H), 6.90-6.84 (m, 2H), 6.57 (br s, 1H), 5.09 (s, 2H), 4.87-4.77 (m, 5H), 4.07 (d, J=6Hz, 1H), 2.90 (d, J=5.1 Hz, 3H), 2.54-2.21 (m, 1H), 1.92 (br s, 2H), 1.36-1.32 (m, 1H). HRMS (M+1)$^+$: calculated 569.1471, found 569.1625. HPLC (System A) 17.2 min (98%) (System B), 16.7 min (98%).

(1'S,2'R,3'S,4'S,5'S)-4'-[6-(5-Iodo-2-methoxy-benzylamino)-2-chloro-purin-9-yl]-2',3'-dihydroxy-bicyclo[3.1.0]hexane-1'-carboxylic acid methylamide (25). $^1$H NMR (CDCl$_3$, 300 MHz) δ 7.79 (s, 1H), 7.67 (s, 1H), 7.54 (dd, J=8.7, 2.7 Hz, 1H), 6.94 (br s, 1H), 6.65 (d, J=8.7 Hz, 1H), 6.48 (br s, 1H), 4.97-4.57 (m, 5H), 4.07 (m, 1H), 3.85 (s, 3H), 2.91 (d, J=5.1 Hz, 3H), 2.24-2.19 (m, 1H), 1.94-1.85 (br s, 2H), 1.38-1.33 (m, 1H). HRMS (M+1)$^+$: calculated 585.0514 found 585.0639. HPLC (System A) 18.7 min (98%) (System B), 13.9 min (99%).

(1'S,2'R,3'S,4'S,5'S)-4'-[6-(2,5-Dimethoxy-benzylamino)-2-chloro-purin-9-yl]-2',3'-dihydroxy-bicyclo[3.1.0]hexane-1'-carboxylic acid methylamide (26). $^1$H NMR (CDCl$_3$, 300 MHz) δ 7.77 (s, 1H), 6.99-6.97 (m, 2H), 6.78-6.75 (m, 2H), 6.90 (br s, 1H), 6.63 (br s, 1H), 4.91 (d, J=6.3 Hz, 1H), 4.77-4.74 (m, 3H), 4.05 (d, J=6 Hz, 1H), 3.82 (s, 3H), 3.75 (s, 3H), 2.90 (d, J=5.1 Hz, 3H), 2.21-2.15 (m, 3H), 1.36-1.32 (m, 1H). HRMS (M+1)$^+$: calculated 489.1653 found 489.1771. HPLC (System A) 17.5 min (98%) (System B), 11.3 min (98%).

(1'S,2'R,3'S,4'S,5'S)-4'-[6-(2-Methyl-benzylamino)-2-chloro-purin-9-yl]-2',3'-dihydroxy-bicyclo[3.1.0]hexane-1'-carboxylic acid methylamide (27). $^1$H NMR (CDCl$_3$, 300 MHz) δ7.76 (s, 1H), 7.31 (d, J=6.9 Hz, 1H), 7.22-7.14 (m, 3H), 6.97 (br s, 1H), 6.20 (br s, 1H), 5.07 (br s, 1H), 4.79 (br s, 2H), 4.34 (br s, 1H), 4.11 (d, J=6Hz, 1H), 3.14 (br s, 1H), 2.92 (d, J=5.1 Hz, 3H), 2.37 (s, 3H), 2.19-2.14 (m, 3H), 1.97 (br s, 1H), 1.38-1.33 (m, 1H). HRMS (M+1)$^+$: calculated 443.1598 found 443.1704. HPLC (System A) 14.3 min (99%) (System B), 12.1 min (99%).

(1'S,2'R,3'S,4'S,5'S)-4'-[6-(3-Methyl-benzylamino)-2-chloro-purin-9-yl]-2',3'-dihydroxy-bicyclo[3.1.0]hexane-1'-carboxylic acid methylamide (28). $^1$H NMR (CDCl$_3$, 300 MHz) δ7.79 (s, 1H), 7.23-7.09 (m, 4H), 6.93 (br s, 1H), 6.42 (br s, 1H), 4.95 (d, J=6.3 Hz, 1H), 4.79 4.70 (m, 3H), 4.09 (d, J=6Hz, 1H), 2.91 (d, J=5.1 Hz, 3H), 2.33 (s, 3H), 2.22-2.17 (m, 1H), 1.97 (br s, 2H), 1.37-1.31 (m, 1H). HRMS (M+1)$^+$: calculated 443.1598 found 443.1633. HPLC (System A) 14.5 min (99%) (System B), 12.0 min (99%).

(1'S,2'R,3'S,4'S,5'S)-4'-[6-(3-(3-Hydroxypropynyl)-benzylamino)-2-chloro-purin-9-yl]-2',3'-dihydroxy-bicyclo[3.1.0]hexane-1'-carboxylic acid methylamide (29). $^1$H NMR (CDCl$_3$, 300 MHz) δ8.02 (s, 1H), 7.70 (s, 1H), 7.61 (br s, 1H), 7.33-7.22 (m, 2H), 5.62 (br s, 1H), 5.20 (br s, 1H), 5.11-5.03 (m, 1H), 4.94 (br s, 1H), 4.80 (s, 1H), 4.67 (d, J=6 Hz, 1H), 4.45-4.31 (m, 1H), 3.96 (br s, 1H), 2.97 (d, J=5.1 Hz, 3H), 2.27-2.24 (m, 1H), 2.07 (br s, 1H), 1.36-1.32 (m, 1H). HRMS (M+1)$^+$: calculated 483.1547 found 483.1596. HPLC (System A) 16.8 min (97%) (System B), 9.2 min (98%).

(1'S,2'R,3'S,4'S,5'S)-4'-[6-(2-Chloro-5-(3-hydroxypropynyl)-benzylamino)-2-chloro-purin-9-yl]-2',3'-dihydroxy-bicyclo[3.1.0]hexane-1'-carboxylic acid methylamide (30). $^1$H NMR (CDCl$_3$, 300 MHz) δ7.93 (s, 1H), 7.75 (s, 1H), 7.38-7.26 (m, 2H), 5.37-5.26 (m, 1H), 4.80-4.75 (m, 2H), 4.65-4.59 (m, 1H), 4.50-4.41 (m, 2H), 4.02 (br s, 1H), 3.72-3.70 (m, 1H), 3.10-3.07 (m, 1H), 2.99 (d, J=5.1 Hz, 3H), 2.29-2.23 (m, 1H), 2.01 (br s, 1H), 1.36-1.32 (m, 1H). HRMS (M+1)$^+$: calculated 517.1158 found 517.1278. HPLC (System A) 17.3 min (98%) (System B), 11.1 min (98%).

(1'S,2'R,3'S,4'S,5'S)-4'-[6-(4-Amino-benzylamino)-2-chloro-purin-9-yl]-2',3'-dihydroxy-bicyclo[3.1.0]hexane-1'-carboxylic acid methylamide (31a). $^1$H NMR (CD$_3$OD, 300 MHz) δ8.02 (s, 1H), 7.15 (d. J=8.1 Hz, 2H), 6.70 (d. J=8.1 Hz, 2H), 5.09 (d, J=6.6 Hz, 1H), 4.81 (s, 1H), 4.61 (s, 2H), 4.02 (d, J=6.6 Hz, 1H), 2.88 (s, 3H), 2.07-2.05 (m, 1H), 1.40-1.35 (m, 1H). HRMS (M+1)$^+$: calculated 444.1551 found 444.1688. HPLC (System A) 10.8 min (98%) (System B), 7.1 min (98%).

(1'S,2'R,3'S,4'S,5'S)-4'-[6-(3-Pyridylmethylamino)-2-chloro-purin-9-yl]-2',3'-dihydroxy-bicyclo[3.1.0]hexane-1'-carboxylic acid methylamide (32). $^1$H NMR (CD$_3$OD, 300 MHz) δ 8.57 (s, 1H), 8.37 (s, 1H), 7.99 (s, 1H), 7.85 (d. J=8.1 Hz, 1H), 7.38-7.34 (m, 1H), 5.05 (d, J=6.6 Hz, 1H), 4.76 (br s, 3H), 3.97 (d, J=6.6 Hz, 1H), 2.26 (s, 3H), 2.04-1.99 (m, 1H), 1.35-1.295 (m, 2H). HRMS (M+1)$^+$: calculated 430.1394 found 430.1467. HPLC (System A) 9.9 min (99%) (System B), 2.7 min (97%).

6-Chloro-2-methylthiopurin-9-ylmethyl 2,2-dimethylpropionate (82). To a stirred solution of 2-amino-6-chloropurin-9-yl-methyl 2,2-dimethylpropionate 81 (0.566 g, 2 mmol) in acetonitrile (2 mL) was added methyl disulfide (0.94 g, 10 mmol), and tert-butyl nitrite (90%, 1.14 g, 10 mmol) and the resulting reaction mixture was stirred at room temperature for 8 h. The reaction mixture was concentrated in vacuo, and the resulting crude product was subjected to silica gel column chromatography (AcOEt/petroleum ether=1/10), which furnished 82 (0.364 g, 55%): $^1$H NMR (CDCl$_3$, 300 MHz) δ 8.19 (s, 1H), 6.12 (s, 2H), 2.65 (s, 3H), 1.17 (s, 9H). MS (m/e) (positive-FAB) 315 (M+1)$^+$.

6-Chloro-2-methylthiopurine (83). To a solution of 6-chloro-2-methylthiopurin-9-ylmethyl 2,2-dimethylpropionate (82) (0.314 g, 1 mmol) in i-PrOH (10 mL) and THF (25 mL) was added 2N aq NaOH (2 mL) and the resulting reaction mixture was stirred at room temperature for 12 hr. The reaction mixture was concentrated under reduced pressure and the residue obtained was purified by silica gel column chromatography (AcOEt/petroleum ether=3/7) which afforded 83 (0.112 g, 56%): 1H NMR (DMSO-d6, 300 MHz) δ 8.54 (s, 1H), 2.58 (s, 3H) MS (m/e) (positive-FAB) 200.9 (M+1)+.

(1 'S,2'R,3'S,4'S,5'S)-4'-[6-Chloro-2-iodo-purin-9-yl]-2',3'-isopropylidene-bicyclo[3.1.0]hexane-1'-carboxylic acid ethyl ester (55). To a solution of triphenylphosphine (0.262 g, 1 mmol) and 6-chloro-2-iodopurine (0.175 g, 0.63 mmol) in THF (3 mL) was added DIAD (0.202 g, 1 mmol), and the reaction mixture was stirred for 10 min. A solution of the alcohol 116 (0.121 g, 0.5 mmol) in THF was added to the reaction mixture, and the mixture was further stirred for 10 h. The solvent was removed in vacuo, and the residue obtained was purified by silica gel column chromatography (AcOEt/petroleum ether=4/6) which afforded 55 (0.136 g, 54%): $^1$H NMR (CDCl$_3$, 300 MHz) δ 1.30-136 (m, 4H), 1.57 (s, 6H), 1.75-180 (m, 1H), 2.12-2.22 (m, 1H), 4.1-4.2 (m, 2H), 4.75 (d, J=14 Hz, 1H), 4.92 (s, 1H), 5.85 (d, J=15 Hz, 1H), 7.98 (s, 1H), MS (m/e) (positive-FAB) 505.0 (M+1)$^+$.

(1'S,2'R,3'S,4'S,5'S)-4'-[6-Chloro-2-methylthio-purin-9-yl]-2',3'-isopropylidene-bicyclo[3.1.0]hexane-1'-carboxylic acid ethyl ester (56). To a solution of triphenylphosphine (0.262 g, 1 mmol) and 6-chloro-2-methylthiopurine 83 (0.125 g, 0.63 mmol) in THF (3 mL) was added DIAD (0.202 g, 1 mmol) and the reaction mixture was stirred for 10 min. After which time alcohol 116 (0.121 g, 0.5 mmol) in THF was added and the reaction mixture was further stirred for 10 hr. The solvent was removed in vacuo and the residue obtained was purified by silica gel column chromatography (AcOEt/petroleum ether=4/6) which afforded 56 (0.112 g, 53%): $^1$H NMR (CDCl$_3$, 300 MHz) δ 1.25-1.55 (m, 4H), 1.56 (s, 6H), 1.75-1.82 (m, 1H), 2.25-2.32 (m, 1H), 2.64 (s, 3H), 4.18-4.29 (m, 2H), 4.82 (d, J=12 Hz, 1H), 4.92 (s, 1H), 5.85 (d, J=11 Hz, 1H), 7.90 (s, 1H), MS (m/e) (positive-FAB) 425.10 (M+1)$^+$.

(1'S,2'R,3'S,4'S,5'S)-4'-[6-Chloro-2-amino-purin-9-yl]-2',3'-isopropylidene-bicyclo[3.1.0]hexane-1'-carboxylic acid ethyl ester (57). To a solution of triphenylphosphine (0.262 g, 1 mmol) and 2-amino-6-chloropurine (0.169 g, 1 mmol) in THF (3 mL) was added DIAD (0.202 g, 1 mmol) and the reaction mixture was stirred for 10 min. After which time alcohol 116 (0.121 g, 0.5 mmol) in THF was added to the reaction mixture was further stirred for 10 h. The solvent was removed in vacuo, and the residue obtained was purified by silica gel column chromatography (AcOEt/petroleum ether=5/5) which afforded 57 (0.041 g, 21%): $^1$H NMR (CDCl$_3$, 300 MHz) δ 1.20-1.55 (m, 6H), 1.52 (m, 4H), 1.75-1.85 (m, 1H), 2.12-2.24 (m, 1H), 4.11-4.24 (m, 2H), 4.67 (d, J=11 Hz, 1H), 4.77 (s, 1H), 5.23 (br s, 2H), 5.88 (d, J=12 H), 7.72 (s, 1H), MS (m/e) (positive-FAB) 394.2 (M+1)$^+$.

(1'S,2'R,3'S,4'S,5'S)-4'-[6-(3-Chlorobenzylamino)-2-iodo-purin-9-yl]-2',3'-isopropylidene-bicyclo[3.1.0]hexane-1'-carboxylic acid ethyl ester (58). $^1$H NMR (CDCl$_3$, 300 MHz) δ 1.11-1.22 (m, 4H), 1.23-1.79 (m, 7H), 2.18-2.24(m, 1H), 4.10-4.21 (m, 2H), 4.66-4.87 (m, 3H), 5.30 (s, 1H), 5.85 (d, J=4.5 Hz, 1H), 6.05-6.16 (m, 1H), 7.21-7.26 (m, 4H), 7.58 (s, 1H), MS (m/e) (positive-FAB) 610.1 (M+1)$^+$.

(1'S,2'R,3'S,4'S,5'S)-4'-[6-(3-Chlorobenzylamino)-2-iodo-purin-9-yl]-2',3'-dihydroxy-bicyclo[3.1.0]hexane-1'-carboxylic acid ethyl ester (35). $^1$H NMR (CDCl$_3$, 300 MHz) δ 1.15-1.22 (m, 1H), 1.65-1.70 (m, 1H), 2.08-2.13 (m, 1H), 2.94 (d, J=4.5 Hz, 3H), 4.02-4.23 (m, 2H), 4.61-4.82 (m, 3H), 5.02-5.12 (m, 1H), 6.22-6.31 (m, 1H), 6.61-6.72 (m, 1H), 7.11-7.21 (m, 4H), 7.76 (s, 1H), MS (m/e) (positive-FAB) 515.2 (M+1)$^+$. HPLC (System A) 15.7 min (98%) (System B), 13.5 min (99%).

(1'S,2'R,3'S,4'S,5'S)-4'-[6-(3-Chlorobenzylamino)-2-methylthio-purin-9-yl]-2',3'-isopropylidene-bicyclo[3.1.0]hexane-1'-carboxylic acid ethyl ester (59). $^1$H NMR (CDCl$_3$, 300 MHz) δ 1.15-1.40 (m, 7H), 1.42-1.81 (m, 5H), 2.53 (s, 3H), 4.15-4.38 (m, 2H), 4.78-4.92 (m, 4H), 5.84 (d, J=8.5 Hz), 6.02 (br s, 1H), 7.19-7.40 (m, 4H), 7.56 (s, 1H), MS (m/e) (positive-FAB) 555.0 (M+1)$^+$.

(1'S,2'R,3'S,4'S,5'S)-4'-[6-(3-Chlorobenzylamino)-2-methylthio-purin-9-yl]-2',3'-dihydroxy-bicyclo[3.1.0]hexane-1'-carboxylic acid ethyl ester (36). $^1$H NMR (CDCl$_3$, 300 MHz) δ 1.12-1.18 (m, 1H), 1.62-176 (m, 1H), 2.22-2.29 (m, 1H), 2.51 (s, 3H), 2.90 (d, J=3.5 Hz, 3H), 4.16 (d, J=4.5 Hz, 1H), 4.65-4.98 (m, 4H), 6.21-6.32 (m, 1H), 6.71-6.81 (m, 1H), 7.11-7.42 (m, 4H), 7.72 (s, 1H), MS (m/e) (positive-FAB) 475.1 (M+1). HPLC (System A) 15.4 min (98%) (System B), 13.1 min (99%).

(1'S,2'R,3'S,4'S,5'S)-4'-[6-Methylamino-2-amino-purin-9-yl]-2',3'-dihydroxy-bicyclo[3.1.0]hexane-1'-carboxylic acid methylamide (15). To a stirred solution of compound 57 (0.039 g, 0.1 mmol) in MeOH was added aq. CH$_3$NH$_2$ solution (0.5 mL, 40%) and the reaction mixture was stirred for 12 h. It was concentrated to dryness, and the residue was dissolved in the mixture containing 10% trifluoroacetic acid/MeOH (4 mL) and H$_2$O (0.5 mL) was heated at 70° C. for 3 h. The solvent was removed, and the residue was dried by coevaporation with dry toluene. The residue was purified using preparative TLC (CHCl$_3$-MeOH, 80:20) to afford 15 (0.011 g, 36%): $^1$H NMR (DMSO-d$_6$, 300 MHz) δ 1.11-1.23 (m, 1H), 1.45-1.58 (m, 1H), 1.62-1.78 (m, 1H), 2.65 (d, J=3.5 Hz, 3H), 2.91 (br s, 3H), 3.18 (d, J=4 hz, 1H), 3.84-3.88 (m, 1H), 4.56 (s, 1H), 4.75 (d, J=10 Hz, 1H), 5.08 (t, J=4.5 Hz, 1H), 5.24 (d, J=6.5 Hz), 5.82 (br s, 2H), 7.1 (br s, 1H), 7.55-7.75 (m, 2H), MS (m/e) (positive-FAB) 334.1 (M+1). HPLC (System A) 6.6 min (98%) (System B), 5.0 min (98%).

(1'S,2'R,3'S,4'S,5'S) -4'-[6-(cyclopentylamino)-2-chloro-purin-9-yl]-2',3'-O-isopropylidene-bicyclo[3.1.0]hexane-1'-carboxylic acid ethyl ester (102). Cyclopentylamine (45.5 mg, 0.53 mmol) was added to a solution of 101 (45 mg, 0.11 mmol) and triethylamine (1 mL) in methanol (3 mL). The mixture was stirred at room temperature for 3 h. Then it was concentrated in vacuo to dryness and the residue was purified by PTLC (chloroform/methanol 20:1) to give 102 (43 mg, 85%). $^1$H NMR (CDCl$_3$, 300 MHz) δ7.64 (s, 1H), 5.95 (br s, 1H), 5.87 (d, J=7.2 Hz, 1H), 5.37 (d, J=6.6 Hz, 1H), 4.85 (s, 1H), 4.72 (d, J=6.9 Hz, 1H), 4.62-4.51 (m, 2H), 2.60-243 (m, 2H), 2.23-2.10 (m, 4H), 1.79-1.70 (m; 5H), 1.56 (s, 3H), 1.35 (t, J=7.8, 3H), 1.32-1.24 (m, 6H). MS (m/e) (positive API-ES) 462.1 (M+H)$^+$.

(1'S,2'R,3'S,4'S,5'S) -4'-[6-(cyclopentylamino)-2-chloro-purin-9-yl]-2',3'-dihydroxy-bicyclo[3.1.0]hexane-1'-carboxylic acid methyl amide (104). The ester 102 (35 mg, 0.07 mmol) was dissolved in methanol (3 mL) and treated with an aqueous solution of methylamine (1 mL, 40%). This mixture was stirred at room temperature overnight, then the solvent was evaporated to dryness, and the white residue was purified by PTLC (chloroform/methanol 9:1) to give the uronamide 103 (15.6 mg, 50%). $^1$H NMR (CDCl$_3$, 300 MHz) δ7.68 (s, 1H), 6.97 (br s, 1H), 6.02 (br s, 1H), 5.67 (d, J=7.8 Hz, 1H), 4.79-4.76 (m, 2H), 4.61-4.54 (m, 1H), 2.91 (d, J=5.1 Hz, 3H), 2.17-2.11 (m, 2H), 2.04-1.81 (m, 2H), 1.78-1.65 (m, 5H), 1.58-1.48 (m, 5H), 1.27 (s, 3H). MS (m/e) (positive API-ES) 447.2 (M+1)$^+$.

The above intermediate (14 mg, 0.03 mmol) was treated with a solution of trifluoroacetic acid in MeOH (5 mL, 10%) and H$_2$O (0.5 mL) and the mixture was heated at 70° C. for 3 h. The solution was cooled and the solvent removed to dryness by coevaporation with toluene in vacuo. The white residue was purified by PTLC (chloroform/methanol 9:1) to give the final product 104 (10.1 mg, 80%). $^1$H NMR (CDCl$_3$, 300 MHz) δ7.81 (s, 1H), 6.96 (br s, 1H), 6.19 (br s, 1H), 5.06 (br s, 1H), 4.88 (br s, 1H), 4.80 (s, 1H), 4.61-4.48 (m, 1H), 4.07 (d, J=6.6 Hz), 3.62 (m, 1H), 2.91 (d, J=4.8 Hz, 3H), 2.58-2.10 (m, 7H), 1.77-1.53 (m, 4H). MS (m/e) (positive API-ES) 407.1 (M+1)$^+$.

EXAMPLE 2

This example illustrates some of the biological properties of compounds in accordance with an embodiment of the invention.

[$^{125}$I]N$^6$-(4-amino-3-iodobenzyl)adenosine-5'-N-methyluronamide (I-AB-MECA; 2000 Ci/mmol), [$^3$H]R—PIA (R—N$^6$-[phenylisopropyl]adenosine, 34 Ci/mmol), [$^3$H] CGS21680 (2-[p-(2-carboxyethyl)phenylethylamino]-5'-N-ethylcarboxamido-adenosine, 47 Ci/mmol) and [$^3$H]cyclic AMP (40 Ci/mmol) were from Amersham Pharmacia Biotech (Buckinghamshire, UK).

CHO (Chinese hamster ovary) cells expressing the recombinant human A$_3$ adenosine receptor were cultured in DMEM supplemented with 10% fetal bovine serum, 100 units/ml penicillin, 100 μg/ml streptomycin, 2 μmol/ml glutamine and 800 μg/ml geneticin. The CHO cells expressing rat A$_3$ adenosine receptor were cultured in DMEM and F12 (1:1). Cells were harvested by trypsinization. After homogenization and suspension, cells were centrifuged at 500 g for 10 min, and the pellet was re-suspended in 50 mM Tris.HCl buffer (pH 8.0) containing 10 mM MgCl$_2$, 1 mM EDTA and 0.1 mg/ml CHAPS. The suspension was homogenized with an electric homogenizer for 10 sec, and was then re-centrifuged at 20,000 g for 20 min at 4° C. The resultant pellets were resuspended in buffer in the presence of 3 Units/ml adenosine deaminase, and the suspension was stored at −80° C. until the binding experiments. Striatal and forebrain tissues from Wistar rats were homogenized in ice-cold 50 mM Tris-HCl buffer, pH 7.4, using an electric homogenizer. The homogenate was centrifuged at 20,000 g for 10 min at 4° C., and the pellet was washed in fresh buffer. The final pellet was stored at −80° C. until the binding experiments. The protein concentration was measured using the Bradford assay. Bradford et al., *Anal. Biochem.* 1976, 72, 248-254.

Binding assays at the A$_1$ and A$_{2A}$ receptors. For binding to rat A$_1$ receptors, the radioligand [$^3$H]CCPA (0.5 nM) was incubated with rat brain membranes. For binding to human A$_1$ receptors, [$^3$H]R—PIA (N$^6$—[(R)-phenylisopropyl]adenosine, 2 nM) was incubated with membranes (40 μg/tube) from CHO cells stably expressing human A$_1$ receptors at 25° C. for 60 min in 50 mM Tris.HCl buffer (pH 7.4; MgCl$_2$, 10 mM) in a total assay volume of 200 μl. Nonspecific binding was determined using 10 μM of CPA (N$^6$-cyclopentyladenosine). For human A$_{2A}$ receptor binding, membranes (20 μg/tube) from HEK-293 cells stably expressing human A$_{2A}$ receptors were incubated with [$^3$H]CGS21680 (2-[p-(2-carboxyethyl) phenyl-ethylamino]-5'-N-ethylcarboxamido-adenosine, 15 nM) at 25° C. for 60 min in 200 μl 50 mM Tris.HCl, pH 7.4, containing 10 mM MgCl$_2$. NECA (10 μM) was used to define nonspecific binding. Reaction was terminated by filtration with GF/B filters.

Binding assay for the A$_3$ adenosine receptor was performed using [$^{125}$I]4-amino-3-iodobenzyl)adenosine-5'-N-methyluronamide. Each tube in the competitive binding assay (Olah et al., *Mol. Pharmacol.* 1994, 45, 978-982) contained 100 μl membrane suspension (20 μg protein), 50 μl [$^{125}$I]4-amino-3-iodobenzyl)adenosine-5'-N-methyluronamide (1.0 nM), and 50 μl of increasing concentrations of the test ligands in Tris.HCl buffer (50 mM, pH 8.0) containing 10 mM MgCl$_2$, 1 mM EDTA. Nonspecific binding was determined using 10 μM of 5'-N-ethylcarboxamido-adenosine in the buffer. The mixtures were incubated at 37° C. for 60 min. Binding reactions were terminated by filtration through Whatman GF/B filters under reduced pressure using a MT-24 cell harvester (Brandell, Gaithersburg, Md.). Filters were washed three times with 9 ml ice-cold buffer. Radioactivity was determined in a Beckman 5500B γ-counter.

The cyclic AMP accumulation assay was performed as follows. Intracellular cyclic AMP levels were measured with a competitive protein binding method. Nordstedt et al., *Anal. Biochem.* 1990, 189, 231-234; Post et al., *Methods Mol. Biol.* 2000, 126, 363-374. CHO cells that expressed recombinant human and rat A$_3$ or the human A$_1$ adenosine receptors were harvested by trypsinization. After centrifugation and resuspension in medium, cells were plated in 24-well plates in 1.0 ml medium. After 24 hr, the medium was removed and cells were washed three times with 1 ml DMEM, containing 50 mM HEPES, pH,7.4. Cells were then treated with agonists and/or test compounds in the presence of rolipram (10 μM) and adenosine deaminase (3 units/mL). After 45 min forskolin (10 μM) was added to the medium, and incubation was continued an additional 15 min. The reaction was terminated by removing the supernatant, and cells were lysed upon the addition of 200 μL of 0.1 M ice-cold HCl. The cell lysate was resuspended and stored at −20° C. For determination of cyclic AMP production, protein kinase A (PKA) was incubated with [$^3$H]cyclic AMP (2 nM) in K$_2$HPO$_4$/EDTA buffer (K$_2$HPO$_4$, 150 mM; EDTA, 10 mM), 20 μL of the cell lysate, and 30 μL 0.1 M HCl or 50 μL of cyclic AMP solution (0-16 pmol/200 μL for standard curve). Bound radioactivity was separated by rapid filtration through Whatman GF/C filters and washed once with cold buffer. Bound radioactivity was measured by liquid scintillation spectrometry.

Anti-ischemic Cardioprotection. Langendorff perfusion of the mouse hearts was carried out. Mice were anesthetized with 60 mg/kg sodium pentobarbital (i.p.), and heart excised in ice-cold perfusion buffer. The aorta was cannulated and retrograde perfused in the Langendorff mode at a pressure of 55 mmHg. To assess isovolumic function, fluid-filled polyvinyl plastic film balloons were inserted into the left ventricle via the left atrium. Balloons were connected to a fluid-filled pressure transducer to measure the left ventricular developed pressure (LVDP), +dP/dt, −dP/dt, and heart rate. To induce normothermic global ischemia and reperfusion, retrograde perfusion of the aorta was stopped, and hearts were immersed in the same perfusion buffer in a water-jacketed bath maintained at 37° C. After 35-min ischemia and 30-min reperfusion, the recovery of left ventricular function was determined by quantifying the LVDP, +dP/dt, and −dP/dt. To quantify the infarct, the hearts were retrograde perfused with 1% triphenyltetrazolium chloride (TTC) in perfusion buffer for 10 minutes after 120-min reperfusion, which allowed washout of pyridine nucleotides from necrotic cells as required for TTC staining. The heart was then immersed in the same TTC buffer for another 10 minutes. The hearts were frozen, cut into six or seven 1 mm slices from apex to base, and scanned for measurement of infarct size by computer morphometry (Image-Pro Plus, version 5.0, Media Cybernetics, Inc, Silver Spring, Md.). The infarct size was quantified as the area of necrosis normalized to the total ventricular area. To assess the anti-ischemic cardioprotective effect of adenosine receptor agonists, vehicle (0.1% DMSO in perfusion buffer) or compound 104 (30 nM) dissolved in DMSO and diluted in buffer were administered in Langendorff mode for five minutes prior to the normothermic global ischemia/reperfusion.

Statistical analysis Binding and functional parameters were calculated using Prism 5.0 software (GraphPAD, San Diego, Calif., USA). IC$_{50}$ values obtained from competition curves were converted to K$_i$ values using the Cheng-Prusoff equation. Cheng et al., *Biochem. Pharmacol.* 1973, 22, 3099-3108. Data were expressed as mean±standard error in Table 1 below.

TABLE 1

Potency of adenosine derivatives at human $A_1$, $A_{2A}$, $A_{2B}$ and $A_3$ Adenosine receptors (ARs) and the rat $A_3$ ARs and maximal agonist effects at human $A_3$ ARs expressed in CHO cells.[a]

1, 6-13

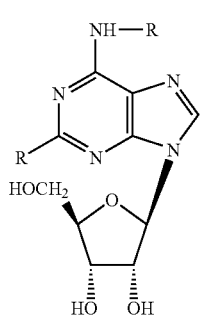

5, 14-36

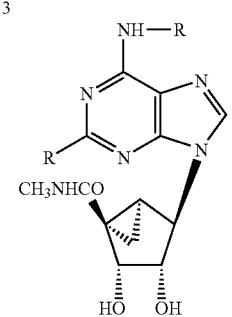

and compound 104.

| Compound | $N^6$-R' | C2-R | $K_i$(h$A_1$AR) nM[a] or % displ. at 10 μM | $K_i$(h$A_{2A}$AR) nM[a] or % displ. at 10 μM | % Activation (h$A_{2B}$AR)[b] at 10 μM | $K_i$(h$A_3$A nM[a]) | % Activation (h$A_3$AR) [b]at 10 μM | $K$(r$A_3$AR)$_i$ |
|---|---|---|---|---|---|---|---|---|
| | Riboside derivatives | | | | | | | |
| 6[c] | CH$_3$ | H | 6000 ± 2000 | 17% | 16 | 9.3 ± 0.4 | 96 ± 3 | 6400 ± 1600[d] |
| 7[c] | CH$_3$ | NH$_2$ | 480 ± 20 | 15% | 11 | 39 ± 2 | 98 ± 3 | >10,000 |
| 1a[c] | 3-iodobenzyl | H | 7.4 ± 1.7 | 140 ± 20 | 58 | 5.8 ± 0.4 | 46 ± 8 | 9.5 ± 1.4 |
| 1b[c] | 3-iodobenzyl | Cl | 17 ± 2 | 200 ± 30 | 16 | 1.8 ± 0.1 | 0 | 2.7 ± 1.2 |
| 8 | 3-chlorobenzyl | H | 20 ± 3 | 1400 ± 200 | ND | 4.4 ± 1.7[d] | 80 ± 3[d] | 35 ± 20[d] |
| 9[c] | 5-chloro-2-methyloxybenzyl | H | 9.2 ± 0.5 | 400 ± 10 | 57 | 1.3 ± 0.2 | 53 ± 3 | ND |
| 10[c] | trans-2-phenyl-cyclopropyl | H | 120 ± 30 | 2500 ± 700 | 26 | 0.86 ± 0.09 | 101 ± 5 | 400 ± 30 |
| 11[d] | 2-methylbenzyl | H | 39 ± 8 | 760 ± 110 | ND | 47 ± 11 | 100 ± 3 | 38 ± 15 |
| 12[d] | 3-pyridylmethyl | H | 42 ± 4 | 2300 ± 120 | ND | 4.5 ± 1.1 | 100 ± 6 | 290 ± 70 |
| 13[f] | 2,2-diphenylethyl | H | 50 ± 16 | 510 ± 50 | 70 | 3.9 ± 0.7 | 0 | 540 ± 200 |
| | 5'-N-Methyluronamido riboside derivatives | | | | | | | |
| 2a | 3-iodobenzyl | H | 51 ± 5 | 2900 ± 600[d] | 0[h] | 1.8 ± 0.7[d] | 100 | 1.1 ± 0.3[i] |
| 2b | 3-iodobenzyl | Cl | 220 ± 20 | 5400 ± 2500[d] | 0[h] | 1.4 ± 0.3[d] | 100 ± 4 | 0.33 ± 0.08[i] |
| | (N)-Methanocarba derivatives | | | | | | | |
| 3 | 3-iodobenzyl | H | 35 ± 3 | 860 ± 70 | ND | 9.2 ± 0.7[d] | 13 ± 1 | ND |
| 4 | 3-iodobenzyl | Cl | 65 ± 17 | 1600 ± 400 | ND | 1.9 ± 0.7[d] | 3 ± 2 | ND |
| | 5'-N-Methyluronamido (N)-methanocarba derivatives | | | | | | | |
| 14 | CH$_3$ | Cl | 2100 ± 1700 | 6% | ND | 2.2 ± 0.6 | 104 ± 7 | 160 ± 30 |
| 15 | CH$_3$ | NH$_2$ | 1600 ± 200 | 17% | ND | 1.6 ± 0.3 | 117 ± 21 | ND |
| 16 | 3-iodobenzyl | H | 700 ± 270 | 6200 ± 100 | ND | 2.4 ± 0.5[e] | 100[e] | ND |
| 5 | 3-iodobenzyl | Cl | 136 ± 22[g] | 784 ± 97[g] | ND | 1.5 ± 0.2[e] | 100[e] | 1.1 ± 0.1 |
| 17 | 3-bromobenzyl | Cl | 270 ± 70 | 1300 ± 100 | 38 | 0.38 ± 0.11 | 100 ± 11 | 0.76 ± 0.08 |
| 18 | 3-chlorobenzyl | Cl | 260 ± 60 | 2300 ± 100 | 38 | 0.29 ± 0.04 | 103 ± 7 | 1.0 ± 0.10 |
| 19 | 3-fluorobenzyl | Cl | 640 ± 140 | 5100 ± 200 | 28 | 2.4 ± 0.1 | 101 ± 5 | 1.6 ± 0.1 |
| 20 | 2,5-dichloro-benzyl | Cl | 540 ± 70 | 1300 ± 100 | 32 | 0.56 ± 0.06 | 102 ± 3 | ND |
| 21 | 2-chloro-5-iodobenzyl | Cl | 340 ± 20 | 480 ± 20 | 58 | 0.83 ± 0.19 | 105 ± 6 | ND |
| 22 | 5-chloro-2-methoxybenzyl | Cl | 240 ± 50 | 1200 ± 100 | 37 | 1.5 ± 0.0 | 107 ± 15 | ND |
| 23 | 5-chloro-2-(aminocarbonyl-methyloxy)benzyl | Cl | 81 ± 10 | 800 ± 70 | ND | 5.3 ± 0.4 | 106 ± 12 | ND |
| 24 | 5-chloro-2-benzyloxybenzyl | Cl | 1200 ± 200 | 850 ± 160 | 49 | 5.2 ± 1.3 | 110 ± 10 | 11 ± 3 |
| 25 | 5-iodo-2-methoxybenzyl | Cl | 200 ± 20 | 430 ± 30 | 46 | 0.58 ± 0.12 | 101 ± 10 | ND |
| 26 | 2,5-dimethoxy-benzyl | Cl | 1600 ± 200 | 52% | 0 | 1.4 ± 0.2 | 107 ± 10 | 0.87 ± 0.24 |
| 27 | 2-methylbenzyl | Cl | 710 ± 300 | 3800 ± 200 | 24 | 3.7 ± 0.6 | 100 ± 3 | ND |
| 28 | 3-methylbenzyl | Cl | 450 ± 80 | 3700 ± 600 | 46 | 0.63 ± 0.18 | 106 ± 3 | ND |
| 29 | 3-(3-hydroxypropynyl)benzyl | Cl | 2600 ± 300 | 56% | 28 | 2.9 ± 0.7 | 102 ± 5 | 1.6 ± 0.6 |
| 30 | 2-chloro-5-(3-hydroxypropynyl)benzyl | Cl | 14% | 12% | 6 | 217 ± 27 | 108 ± 5 | ND |

TABLE 1-continued

Potency of adenosine derivatives at human $A_1$, $A_{2A}$, $A_{2B}$ and $A_3$ Adenosine receptors (ARs) and the rat $A_3$ ARs and maximal agonist effects at human $A_3$ ARs expressed in CHO cells.[a]

Structures for 1, 6-13 (left) and 5, 14-36 (right) and compound 104.

| Compound | $N^6$-R' | C2-R | $K_i(hA_1AR)$ $nM^a$ or % displ. at 10 μM | $K_i(hA_{2A}AR)$ $nM^a$ or % displ. at 10 μM | % Activation $(hA_{2B}AR)^b$ at 10 μM | $K_i(hA_3A$ $nM^a)$ | % Activation $(hA_3AR)$ [b] at 10 μM | $K(rA_3AR)_i$ |
|---|---|---|---|---|---|---|---|---|
| 31a | 4-aminobenzyl | Cl | 4100 ± 100 | 28% | 22 | 14 ± 3 | 98 ± 10 | ND |
| 31b | 4-amino-3-iodobenzyl | Cl | 48 ± 2 | 1100 ± 100 | ND | 3.1 ± 0.1 | 103 ± 7 | ND |
| 32 | 3-pyridylmethyl | Cl | 2600 ±1200 | 33% | 4 | 11 ± 3 | 106 ± 7 | ND |
| 33 | trans-2-phenyl-1- | Cl | 770 ± 50 | 4800 ± 200 | 48 | 0.78 ± 0.06 | 110 ± 7 | ND |
| 34 | 2,2-diphenylethyl | Cl | 1300 ± 100 | 1600 ± 100 | 46 | 0.69 ± 0.02 | 107 ± 9 | 10 ± 4 |
| 35 | 3-chlorobenzyl | I | 2200 ± 600 | 43% | ND | 3.6 ± 0.8 | 107 ± 3 | 3.9 ± 0.4 |
| 36 | 3-chlorobenzyl | $SCH_3$ | 610 ± 40 | 52% | ND | 1.5 ± 0.2 | 100 ± 4 | ND |
| 104 | cyclopentyl | Cl | 18.3 ± 6.3 | 3250 ± 300 | | 3.7 ± 0.9 | 101 ± 10 | 5.8 ± 1.6 |

[a]All AR experiments were performed using adherent CHO cells stably transfected with cDNA encoding the human or rat ARs. Percent activation of the human $A_3AR$ was determined at 10 μM. Binding at human $A_1$ and $A_{2A}ARs$ in this study was carried out as described in Methods using [3H]R-PIA or [$^3$H]CGS 21680 as a radioligand. Values from the present study are expressed as mean ± s.e.m., n = 3-5.
[b]Percent activity at 10 μM, relative to 10 μM Cl-IB-MECA ($A_3$).
[c]Data from Ohno et al., supra
[d]Data from Gao et al., J. Med. Chem. 2002, 45, 4471-4484; Biochem. Pharmacol. 2003, 65, 1675-1684.
[e]Data from Lee et al., supra
[f]Data from Tchilibon et al., supra
[g]Data from Jacobson et al., Drug. Devel. Res. 2003, 58, 330-339.
[h]Data from de Zwart et al., Nucleosides and Nucleotides 1998, 17, 969-986.
[i]Data from Kim et al., supra
Nd not determined.

Compound 104 was equipotent in binding to human and rat $A_1$ adenosine receptors with $K_i$ values of 18.3 and 17.4 nM, respectively. Also, the affinity of compound 104 was similar at human and rat $A_3$ adenosine receptors with $K_i$ values of 3.7 and 5.8 nM, respectively. Concentration response curves of inhibition of forskolin-stimulated production of 3',5'-cyclic-adenosine monophosphate (cAMP) in intact transfected CHO cells indicate that compound 104 is a dual acting full agonist with nearly equivalent functional potencies at human $A_1$ ($EC_{50}$=8.2 nM) and $A_3$ ($EC_{50}$=2.8 nM) adenosine receptors.

Compound 104 was tested in an intact mouse heart model of ischemia and reperfusioncompound 104 at 30 nM exerted a potent anti-ischemic cardioprotective effect (Table 2). The mixed-agonist was perfused until the induction of ischemia. The recovery of left ventricular developed pressure, +dP/dt, −dP/dt and heart rate all improved significantly following treatment with the mixed agonist 104. The infarct size determined using computer morphometry after staining with triphenyltetrazolium chloride (TTC) was significantly reduced in the group treated with 104. The percent necrosis in the group treated with 104 was 15±7% compared to 23±8% in the vehicle-treated controls, n=6.

TABLE 2

Recovery of left ventricular function in a mouse heart model of ischemia/reperfusion[a].

| Parameter | Vehicle[b] | Compound 104[c] | Significance |
|---|---|---|---|
| LVDP[d] | 8.5 ± 5.3 | 26.0 ± 4.8 | t = 7.1, P < 0.0001 |
| +dP/dt[d] | 6.3 ± 3.9 | 21.1 ± 4.9 | t = 7.4, P < 0.0001 |
| −dP/dt[d] | 8.2 ± 3.7 | 24.6 ± 7 | t = 7.22, P < 0.0001 |
| HR[d] | 37.1 ± 32.6 | 93.8 ± 19.3 | t = 4.1, P < 0.0005 |
| % necrosis | 23.4 ± 7.8 | 15.0 ± 6.9 | t = 2.32, P[e] = 0.029 |

[a]Values were obtained after 35 global ischemia followed by reperfusion.
[b]DMSO, n = 16.
[c]A concentration of 30 nM 104 (initially dissolved in DMSO) was used, n = 6.
[d]% of baseline prior to ischemia/reperfusion.
[e]Two-tailed.

Figure 8:
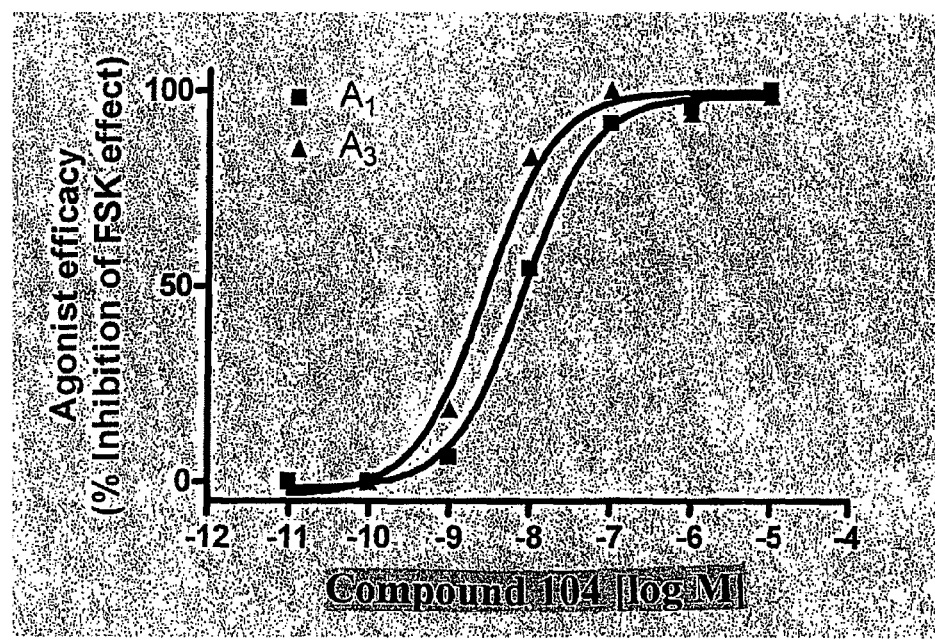
FIG. 8 depicts the inhibition of forskolin-stimulated cyclic AMP production induced by a compound of the invention (compound 104) in CHO cells stably transfected with the human $A_1$ (■) or $A_3$ (σ) adenosine receptor.

Inhibition of forskolin-stimulated cyclic AMP production induced by compound 104 in CHO cells stably transfected with the human $A_1$ (■) or $A_3$ (σ) adenosine receptors in FIG. 8. All experiments were performed in the presence of 10 μM rolipram and 3 Units/ml adenosine deaminase. Forskolin (10 μM) was used to stimulate cyclic AMP levels. The level of cAMP corresponding to 100% was 220±30 pmol/mL. The data shown were from one experiment performed in duplicate and are typical of two independent experiments giving similar results. $EC_{50}$ values were 8.2 and 2.8 nM at the $A_1$ or $A_3$ adenosine receptor, respectively. 100% values are normalized to the maximal effect of NECA (10 μM) as a full agonist at either the $A_1$ or $A_3$ adenosine receptor.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:
1. A compound of the formula:

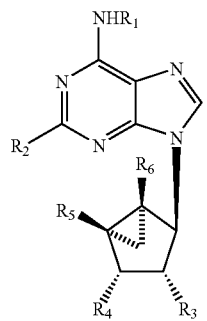

wherein:
$R_1$ is selected from the group consisting of $C_1$-$C_6$ alkyl, $C_1$-$C_6$ alkoxy, hydroxy, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkoxy, heterocyclyl $C_1$-$C_6$ alkyl, heterocyclyl, 4-[[[4-[[[(2-amino $C_1$-$C_6$ alkyl)amino]-carbonyl]-$C_1$-$C_6$ alkyl]anilino]carbonyl]$C_1$-$C_6$ alkyl]$C_6$-$C_{14}$ aryl, and $C_6$-$C_{14}$ aryl $C_3$-$C_8$ cycloalkyl, wherein the aryl or heterocyclyl portion of $R_1$ is optionally substituted with one or more substituents selected from the group consisting of halo, amino, $C_1$-$C_6$ alkyl, $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, aminocarbonyl $C_1$-$C_6$ alkoxy, and $C_6$-$C_{14}$ aryl $C_1$-$C_6$ alkoxy, and any combination thereof; and the alkyl or cycloalkyl portion of $R_1$ is optionally substituted with one or more substituents selected from the group consisting of halo, hydroxy, amino, and any combination thereof;

$R_2$ is selected from the group consisting of hydrogen, halo, amino, $C_1$-$C_6$ alkoxy, $C_1$-$C_6$ alkylthio, $C_2$-$C_6$ alkenyloxy, $C_2$-$C_6$ alkynyloxy, $C_3$-$C_8$ cycloalkyl $C_1$-$C_6$ alkoxy, $C_3$-$C_8$ cycloalkenyloxy, $C_7$-$C_{12}$ bicycloalkyl $C_1$-$C_6$ alkoxy, $C_7$-$C_{12}$ bicycloalkenyl $C_1$-$C_6$ alkoxy, $C_6$-$C_{14}$ aryloxy, $C_6$-$C_{14}$ aryl $C_1$-$C_6$ alkoxy, $C_6$-$C_{14}$ aryl $C_3$-$C_6$ cycloalkoxy, $C_6$-$C_{14}$ aryl $C_1$-$C_6$ alkylamino, $C_6$-$C_{14}$ aryl $C_1$-$C_6$ alkylthio, $C_1$-$C_6$ alkyl $C_6$-$C_{14}$ aryl $C_1$-$C_6$ alkoxy, $C_1$-$C_6$ alkoxy $C_6$-$C_{14}$ aryl $C_1$-$C_6$ alkoxy, halo $C_6$-$C_{14}$ aryloxy, halo $C_6$-$C_{14}$ aryl $C_1$-$C_6$ alkoxy, $C_6$-$C_{14}$ aryl $C_1$-$C_6$ alkylamino, $C_1$-$C_6$ dialkoxy $C_6$-$C_{14}$ aryl $C_1$-$C_6$ alkoxy, heterocyclyl $C_1$-$C_6$ alkoxy, hydrazinyl, and pyrazolyl, said pyrazolyl being optionally substituted with one or more substituents selected from the group consisting of $C_1$-$C_6$ alkyl, $C_6$-$C_{14}$ aryl $C_1$-$C_6$ alkyl, $C_6$-$C_{14}$ haloaryl $C_1$-$C_6$ alkyl, aminocarbonyl, $C_1$-$C_6$ alkyl aminocarbonyl, $C_1$-$C_6$ alkoxyphenyl, $C_6$-$C_{14}$ haloaryl, and heterocyclyl, and any combination thereof;

$R_3$ and $R_4$ are independently selected from the group consisting of hydroxy, amino, mercapto, ureido, $C_1$-$C_6$ alkyl carbonylamino, hydroxy $C_1$-$C_6$ alkyl, and hydrazinyl;

$R_5$ is selected from the group consisting of $C_1$-$C_3$ alkyl aminocarbonyl, $C_1$-$C_3$ alkylthio $C_1$-$C_3$ alkyl, halo $C_1$-$C_3$ alkyl, hydrazinyl, amino $C_1$-$C_3$ alkyl, $C_3$-$C_6$ cycloalkylamino, hydroxylamino, and $C_2$-$C_3$ alkenyl; and $R_6$ is hydrogen or fluorine;

or a pharmaceutically acceptable salt thereof;

with the provisos that (i) when $R_1$ is methyl, $R_2$ is chloro, $R_3$ and $R_4$ are hydroxyl, and $R_5$ is methylaminocarbonyl, $R_6$ is not hydrogen; (ii) when $R_1$ is 3-iodobenzyl, $R_2$ is hydrogen or chloro, $R_3$ and $R_4$ are hydroxyl, and $R_5$ is methylaminocarbonyl, $R_6$ is not hydrogen; and (iii) when $R_1$ is $C_1$-$C_6$ alkyl, $C_3$-$C_8$ cycloalkyl, $C_1$-$C_6$ alkoxy, $C_6$-$C_{14}$ aryl, $C_6$-$C_{14}$ aryl $C_1$-$C_6$ alkyl, heterocyclyl, or $C_7$-$C_{12}$ bicycloalkyl, $R_2$ is hydrogen or halo, $R_3$ and $R_4$ are hydroxy, and $R_6$ is hydrogen, $R_5$ is not alkylamino carbonyl.

2. The compound or pharmaceutically acceptable salt of claim 1, wherein $R_1$ is selected from the group consisting of $C_1$-$C_6$ alkyl, $C_3$-$C_8$ cycloalkyl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_3$-$C_8$ cycloalkyl, and heterocyclyl $C_1$-$C_6$ alkyl, wherein the aryl or heterocyclyl portion of $R_1$ is optionally substituted with one or more substituents selected from the group consisting of halo, amino, $C_1$-$C_6$ alkyl, $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, aminocarbonyl $C_1$-$C_6$ alkoxy, and $C_6$-$C_{14}$ aryl $C_1$-$C_6$ alkoxy, and any combination thereof.

3. The compound or pharmaceutically acceptable salt of claim 2, wherein $R_1$ is selected from the group consisting of $C_1$-$C_6$ alkyl, $C_3$-$C_8$ cycloalkyl, phenyl $C_1$-$C_6$ alkyl, diphenyl $C_1$-$C_6$ alkyl, phenyl $C_3$-$C_8$ cycloalkyl, diphenyl $C_3$-$C_8$ cycloalkyl, and heterocyclyl $C_1$-$C_6$ alkyl, wherein the phenyl or heterocyclyl portion of $R_1$ is optionally substituted with one or more substituents selected from the group consisting of halo, amino, $C_1$-$C_6$ alkyl, $C_1$-$C_6$ alkoxy, phenoxy, hydroxy $C_1$-$C_6$ alkyl, hydroxy $C_2$-$C_6$ alkenyl, hydroxy $C_2$-$C_6$ alkynyl, aminocarbonyl $C_1$-$C_6$ alkoxy, and phenyl $C_1$-$C_6$ alkoxy, and any combination thereof.

4. The compound or pharmaceutically acceptable salt of claim 3, wherein $R_1$ is selected from the group consisting of methyl, cyclopentyl, benzyl, diphenyl ethyl, phenyl cyclopropyl, diphenyl cyclopropyl, and pyridyl methyl, wherein the phenyl or pyridyl portion of $R_1$ is optionally substituted with one or more substituents selected from the group consisting of halo, amino, $C_1$-$C_6$ alkyl, $C_1$-$C_6$ alkoxy, phenoxy, hydroxy $C_1$-$C_6$ alkyl, hydroxy $C_2$-$C_6$ alkenyl, hydroxy $C_2$-$C_6$ alkynyl, aminocarbonyl $C_1$-$C_6$ alkoxy, and phenyl $C_1$-$C_6$ alkoxy, and any combination thereof.

5. The compound or pharmaceutically acceptable salt of claim 4, wherein $R_1$ is benzyl which is optionally substituted with one or more substituents selected from the group consisting of halo, amino, $C_1$-$C_6$ alkyl, $C_1$-$C_6$ alkoxy, phenoxy, hydroxy $C_1$-$C_6$ alkyl, hydroxy $C_2$-$C_6$ alkenyl, hydroxy $C_2$-$C_6$ alkynyl, aminocarbonyl $C_1$-$C_6$ alkoxy, and phenyl $C_1$-$C_6$ alkoxy, and any combination thereof.

6. The compound or pharmaceutically acceptable salt of claim 1, wherein $R_1$ is methyl, cyclopentyl, or 7-norbornyl.

7. The compound or pharmaceutically acceptable salt of claim 5, wherein $R_1$ is selected from the group consisting of 3-iodobenzyl, 3-bromobenzyl, 3-chlorobenzyl, 3-fluorobenzyl, 2,5-dichlorobenzyl, 2-chloro-5-iodobenzyl, 5-chloro-2-methoxybenzyl, 5-chloro-2-(aminocarbonyl methoxy)benzyl, 5-chloro-2-benzyloxybenzyl, 5-iodo-2-methoxybenzyl, 2,5-dimethoxybenzyl, 2-methylbenzyl, 3-(3-hydroxypropynyl)benzyl, 2-chloro-5-(3-hydroxypropynyl)benzyl, 4-aminobenzyl, and 4-amino-3-iodo-benzyl.

8. The compound or pharmaceutically acceptable salt of claim 4, wherein $R_1$ is 3-pyridylmethyl, trans-2-phenyl-1-cyclopropyl, or 2,2-diphenylethyl.

9. The compound or pharmaceutically acceptable salt of claim 1, wherein $R_2$ is selected from the group consisting of halo, amino, and $C_1$-$C_6$ alkylthio.

10. The compound or pharmaceutically acceptable salt of claim 1, wherein $R_3$ and $R_4$ are independently selected from the group consisting of hydroxy, amino, mercapto, and ureido.

11. The compound or pharmaceutically acceptable salt of claim 1, wherein $R_5$ is selected from the group consisting of $C_1$-$C_3$ alkyl aminocarbonyl, $C_1$-$C_3$ alkylthio $C_1$-$C_3$ alkyl, halo $C_1$-$C_3$ alkyl, amino $C_1$-$C_3$ alkyl, hydroxy $C_1$-$C_3$ alkyl, and $C_3$-$C_6$ cycloalkylamino.

12. The compound or pharmaceutically acceptable salt of claim 1, wherein $R_6$ is hydrogen.

13. The compound or pharmaceutically acceptable salt of claim 1, wherein said pyrazolyl is substituted with a heterocyclyl selected from the group consisting of pyridyl, quinolinyl, isoquinolinyl, pyrimidinyl, and benzoxazolyl.

14. The compound or pharmaceutically acceptable salt of claim 1, wherein $R_1$ is methyl, $R_2$ is amino, $R_3$ and $R_4$ are hydroxy, $R_5$ is methylamino carbonyl, and $R_6$ is hydrogen.

15. The compound or pharmaceutically acceptable salt of claim 1, wherein $R_1$ is 3-bromobenzyl, 3-chlorobenzyl, 3-fluorobenzyl, 2,5-dichlorobenzyl, 2-chloro-5-iodobenzyl, 5-chloro-2-methoxybenzyl, 5-chloro-2-(aminocarbonyl methoxy)benzyl, 5-chloro-2-benzyloxybenzyl, 5-iodo-2-methoxybenzyl, 2,5-dimethoxybenzyl, 2-methylbenzyl, 3-methylbenzyl, 3-(3-hydroxypropynyl)benzyl, 2-chloro-5-(3-hydroxypropynyl)benzyl, 4-aminobenzyl, 4-amino-3-iodobenzyl, 3-pyridylmethyl, trans-2-phenyl-l-cyclopropyl, 2,2-diphenylethyl, cyclopentyl, or 7-norbornyl, $R_2$ is chloro, $R_3$ and $R_4$ are hydroxy, $R_5$ is methylamino carbonyl, and $R_6$ is hydrogen.

16. The compound or pharmaceutically acceptable salt of claim 1, wherein $R_1$ is 3-chlorobenzyl, $R_2$ is iodo or methylthio, $R_3$ and $R_4$ are hydroxy, $R_5$ is methylamino carbonyl, and $R_6$ is hydrogen.

17. A compound of the formula:

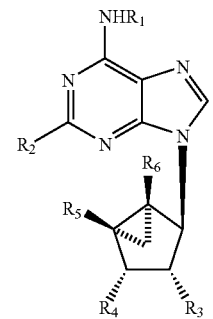

wherein:
(a) $R_1$ is $C_3$-$C_8$ cycloalkyl substituted with aminocarbonylamino;
   $R_2$ is selected from the group consisting of hydrogen, halo, $C_1$-$C_6$ alkoxy, $C_1$-$C_6$ alkylthio, $C_1$-$C_6$ alkylamino;
   $R_3$ is hydroxy;
   $R_4$ is selected from the group consisting of amino, hydroxy, and halo;
   $R_5$ is a $C_1$-$C_3$ alkyl aminocarbonyl; and
   $R_6$ is hydrogen or halo;
(b) $R_1$ is $C_3$-$C_8$ cycloalkyl, optionally substituted with one or more substituents selected from the group consisting of halo, hydroxy, amino, aminocarbonylamino, and any combination thereof;
   $R_2$ is selected from the group consisting of $C_1$-$C_6$ alkoxy and $C_1$-$C_6$ alkylamino;
   $R_3$ is hydroxy;
   $R_4$ is selected from the group consisting of amino, hydroxy, and halo;
   $R_5$ is a $C_1$-$C_3$ alkyl aminocarbonyl; and
   $R_6$ is hydrogen or halo;
(c) $R_1$ is $C_3$-$C_8$ cycloalkyl, optionally substituted with one or more substituents selected from the group consisting of halo, hydroxy, amino, aminocarbonylamino, and any combination thereof;
   $R_2$ is selected from the group consisting of hydrogen, halo, $C_1$-$C_6$ alkoxy, $C_1$-$C_6$ alkylthio, $C_1$-$C_6$ alkylamino;
   $R_3$ is hydroxy;
   $R_4$ is halo;
   $R_5$ is a $C_1$-$C_3$ alkyl aminocarbonyl; and
   $R_6$ is hydrogen or halo; or
(d) $R_1$ is $C_3$-$C_8$ cycloalkyl, optionally substituted with one or more substituents selected from the group consisting of halo, hydroxy, amino, aminocarbonylamino, and any combination thereof;
   $R_2$ is selected from the group consisting of $C_1$-$C_6$ alkoxy and $C_1$-$C_6$ alkylamino;
   $R_3$ is hydroxy;

$R_4$ is selected from the group consisting of amino, hydroxy, and halo;
$R_5$ is a $C_1$-$C_3$ alkyl aminocarbonyl; and
$R_6$ is halo;
or a pharmaceutically acceptable salt thereof 18. A compound of the formula:

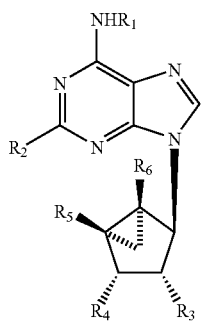

wherein $R_1$ is selected from the group consisting of

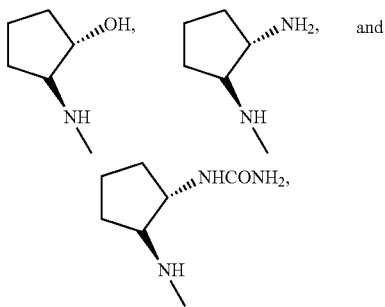

wherein $R_1$ is shown along with the $N^6H$ of the compound;
$R_2$ is selected from the group consisting of hydrogen, halo, $C_1$-$C_6$ alkylthio, $C_1$-$C_6$ alkoxy, and $C_1$-$C_6$ alkylamino;
$R_3$ is hydroxy;
$R_4$ is selected from the group consisting of amino, hydroxy, and halo;
$R_5$ is a $C_1$-$C_3$ alkyl aminocarbonyl; and
$R_6$ is hydrogen or halo; or a pharmaceutically acceptable salt thereof.

19. A compound of the formula

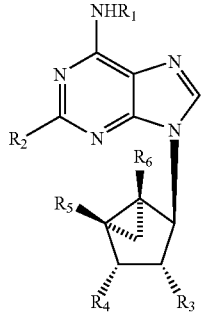

wherein $R_1$ is heterocyclyl;
$R_2$ is selected from the group consisting of hydrogen, halo, $C_1$-$C_6$ alkylthio, $C_1$-$C_6$ alkoxy, and $C_1$-$C_6$ alkylamino;
$R_3$ is hydroxy;
$R_4$ is selected from the group consisting of amino, hydroxy, and halo;
$R_5$ is a $C_1$-$C_3$ alkyl aminocarbonyl; and
$R_6$ is hydrogen or halo; or a pharmaceutically acceptable salt thereof.

20. The compound or pharmaceutically acceptable salt of claim 19, wherein $R_1$ is tetrahydrofuranyl.

21. The compound or pharmaceutically acceptable salt of claim 20, wherein $R_1$ is

wherein $R_1$ is shown along with $N^6H$.

22. A pharmaceutical composition comprising a compound or pharmaceutically acceptable salt of claim 1, and a pharmaceutically acceptable carrier.

23. A method for activating an $A_3$ adenosine receptor in a mammal comprising administering to the mammal an effective amount of a compound or pharmaceutically acceptable salt of claim 1.

24. A method for activating an $A_3$ adenosine receptor in a cell comprising contacting said cell in vivo with a compound or pharmaceutically acceptable salt of claim 1.

25. A method for activating $A_3$ and $A_1$ adenosine receptors in a mammal comprising administering to the mammal an effective amount of a compound or pharmaceutically acceptable salt of claim 17.

26. A method of cardioprotecting a patient in need thereof comprising administering to the patient an agonist having affinity for both the $A_1$ and $A_3$ adenosine receptors in an effective amount of a compound or pharmaceutically acceptable salt of claim 17 to activate the $A_1$ and $A_3$ adenosine receptors in the heart of said patient.

27. The method of claim 26, wherein the cardioprotecting comprises preventing or reducing ischemic damage to the heart.

28. A pharmaceutical composition comprising a compound or pharmaceutically acceptable salt of claim 17 and a pharmaceutically acceptable carrier.

29. A pharmaceutical composition comprising a compound or pharmaceutically acceptable salt of claim 18 and a pharmaceutically acceptable carrier.

30. A pharmaceutical composition comprising a compound or pharmaceutically acceptable salt of claim 19 and a pharmaceutically acceptable carrier.

31. A method for activating an $A_3$ adenosine receptor in a mammal comprising administering to the mammal an effective amount of a compound or pharmaceutically acceptable salt of claim 17.

32. A method for activating an $A_3$ adenosine receptor in a mammal comprising administering to the mammal an effective amount of a compound or pharmaceutically acceptable salt of claim 18.

33. A method for activating an $A_3$ adenosine receptor in a mammal comprising administering to the mammal an effective amount of a compound or pharmaceutically acceptable salt of claim 19.

34. A method for activating $A_3$ and $A_1$ adenosine receptors in a mammal comprising administering to the mammal an effective amount of a compound or pharmaceutically acceptable salt of claim 18.

35. A method for activating $A_3$ and $A_1$ adenosine receptors in a mammal comprising administering to the mammal an effective amount of a compound or pharmaceutically acceptable salt of claim 19.

36. A method of cardioprotecting a patient in need thereof comprising administering to the patient an agonist having affinity for both the $A_1$ and $A_3$ adenosine receptors in an effective amount of a compound or pharmaceutically acceptable salt of claim 18 to activate the $A_1$ and $A_3$ adenosine receptors in the heart of said patient.

37. A method of cardioprotecting a patient in need thereof comprising administering to the patient an agonist having affinity for both the $A_1$ and $A_3$ adenosine receptors in an effective amount of a compound or pharmaceutically acceptable salt of claim 19 to activate the $A_1$ and $A_3$ adenosine receptors in the heart of said patient.

38. The compound, or pharmaceutically acceptable salt thereof, of claim 1, wherein:

$R_1$ is 3-bromobenzyl, $R_2$ is chloro, $R_3$ and $R_4$ are hydroxy, $R_5$ is methylamino carbonyl, and $R_6$ is hydrogen;

$R_1$ is 3-chlorobenzyl, $R_2$ is chloro, $R_3$ and $R_4$ are hydroxy, $R_5$ is methylamino carbonyl, and $R_6$ is hydrogen;

$R_1$ is 3-fluorobenzyl, $R_2$ is chloro, $R_3$ and $R_4$ are hydroxy, $R_5$ is methylamino carbonyl, and $R_6$ is hydrogen;

$R_1$ is 2,5-dichlorobenzyl, $R_2$ is chloro, $R_3$ and $R_4$ are hydroxy, $R_5$ is methylamino carbonyl, and $R_6$ is hydrogen;

$R_1$ is 2-chloro-5-iodobenzyl, $R_2$ is chloro, $R_3$ and $R_4$ are hydroxy, $R_5$ is methylamino carbonyl, and $R_6$ is hydrogen;

$R_1$ is 5-chloro-2-methoxybenzyl, $R_2$ is chloro, $R_3$ and $R_4$ are hydroxy, $R_5$ is methylamino carbonyl, and $R_6$ is hydrogen;

$R_1$ is 5-chloro-2-(aminocarbonylmethoxy)benzyl, $R_2$ is chloro, $R_3$ and $R_4$ are hydroxy, $R_5$ is methylamino carbonyl, and $R_6$ is hydrogen;

$R_1$ is 5-chloro-2-benzyloxybenzyl, $R_2$ is chloro, $R_3$ and $R_4$ are hydroxy, $R_5$ is methylamino carbonyl, and $R_6$ is hydrogen;

$R_1$ is 5-iodo-2-methoxybenzyl, $R_2$ is chloro, $R_3$ and $R_4$ are hydroxy, $R_5$ is methylamino carbonyl, and $R_6$ is hydrogen;

$R_1$ is 2,5-dimethoxybenzyl, $R_2$ is chloro, $R_3$ and $R_4$ are hydroxy, $R_5$ is methylamino carbonyl, and $R_6$ is hydrogen;

$R_1$ is 2-methylbenzyl, $R_2$ is chloro, $R_3$ and $R_4$ are hydroxy, $R_5$ is methylamino carbonyl, and $R_6$ is hydrogen;

$R_1$ is 3-methylbenzyl, $R_2$ is chloro, $R_3$ and $R_4$ are hydroxy, $R_5$ is methylamino carbonyl, and $R_6$ is hydrogen;

$R_1$ is 3-(3-hydroxypropynyl)benzyl, $R_2$ is chloro, $R_3$ and $R_4$ are hydroxy, $R_5$ is methylamino carbonyl, and $R_6$ is hydrogen;

$R_1$ is 2-chloro-5-(3-hydroxypropynyl)benzyl, $R_2$ is chloro, $R_3$ and $R_4$ are hydroxy, $R_5$ is methylamino carbonyl, and $R_6$ is hydrogen;

$R_1$ is 4-aminobenzyl, $R_2$ is chloro, $R_3$ and $R_4$ are hydroxy, $R_5$ is methylamino carbonyl, and $R_6$ is hydrogen;

$R_1$ is 4-amino-3-iodobenzyl, $R_2$ is chloro, $R_3$ and $R_4$ are hydroxy, $R_5$ is methylamino carbonyl, and $R_6$ is hydrogen;

$R_1$ is 3-pyridylmethyl, $R_2$ is chloro, $R_3$ and $R_4$ are hydroxy, $R_5$ is methylamino carbonyl, and $R_6$ is hydrogen;

$R_1$ is trans-2-phenyl-1-cyclopropyl, $R_2$ is chloro, $R_3$ and $R_4$ are hydroxy, $R_5$ is methylamino carbonyl, and $R_6$ is hydrogen;

$R_1$ is 2,2-diphenylethyl, $R_2$ is chloro, $R_3$ and $R_4$ are hydroxy, $R_5$ is methylamino carbonyl, and $R_6$ is hydrogen;

$R_1$ is cyclopentyl, $R_2$ is chloro, $R_3$ and $R_4$ are hydroxy, $R_5$ is methylamino carbonyl, and $R_6$ is hydrogen; or $R_1$ is 7-norbornyl, $R_2$ is chloro, $R_3$ and $R_4$ are hydroxy, $R_5$ is methylamino carbonyl, and $R_6$ is hydrogen.

39. The compound, or phatinaceutically acceptable salt thereof, of claim 38, wherein:

$R_1$ is 3-bromobenzyl, $R_2$ is chloro, $R_3$ and $R_4$ are hydroxy, $R_5$ is methylamino carbonyl, and $R_6$ is hydrogen;

$R_1$ is 3-chlorobenzyl, $R_2$ is chloro, $R_3$ and $R_4$ are hydroxy, $R_5$ is methylamino carbonyl, and $R_6$ is hydrogen;

$R_1$ is 2,5-dichlorobenzyl, $R_2$ is chloro, $R_3$ and $R_4$ are hydroxy, $R_5$ is methylamino carbonyl, and $R_6$ is hydrogen;

$R_1$ is 2-chloro-5-iodobenzyl, $R_2$ is chloro, $R_3$ and $R_4$ are hydroxy, $R_5$ is methylamino carbonyl, and $R_6$ is hydrogen;

$R_1$ is 5-iodo-2-methoxybenzyl, $R_2$ is chloro, $R_3$ and $R_4$ are hydroxy, $R_5$ is methylamino carbonyl, and $R_6$ is hydrogen;

$R_1$ is 2,5-dimethoxybenzyl, $R_2$ is chloro, $R_3$ and $R_4$ are hydroxy, $R_5$ is methylamino carbonyl, and $R_6$ is hydrogen;

$R_1$ is 3-methylbenzyl, $R_2$ is chloro, $R_3$ and $R_4$ are hydroxy, $R_5$ is methylamino carbonyl, and $R_6$ is hydrogen;

$R_1$ is 3-(3-hydroxypropynyl)benzyl, $R_2$ is chloro, $R_3$ and $R_4$ are hydroxy, $R_5$ is methylamino carbonyl, and $R_6$ is hydrogen;

$R_1$ is trans-2-phenyl-1-cyclopropyl, $R_2$ is chloro, $R_3$ and $R_4$ are hydroxy, $R_5$ is methylamino carbonyl, and $R_6$ is hydrogen;

$R_1$ is 2,2-diphenylethyl, $R_2$ is chloro, $R_3$ and $R_4$ are hydroxy, $R_5$ is methylamino carbonyl, and $R_6$ is hydrogen; or $R_1$ is cyclopentyl, $R_2$ is chloro, $R_3$ and $R_4$ are hydroxy, $R_5$ is methylamino carbonyl, and $R_6$ is hydrogen.

40. The compound, or pharmaceutically acceptable salt thereof, of claim 39, wherein:

$R_1$ is 3-bromobenzyl, $R_2$ is chloro, $R_3$ and $R_4$ are hydroxy, $R_5$ is methylamino carbonyl, and $R_6$ is hydrogen;

$R_1$ is 3-chlorobenzyl, $R_2$ is chloro, $R_3$ and $R_4$ are hydroxy, $R_5$ is methylamino carbonyl, and $R_6$ is hydrogen; or $R_1$ is 2,2-diphenylethyl, $R_2$ is chloro, $R_3$ and $R_4$ are hydroxy, $R_5$ is methylamino carbonyl, and $R_6$ is hydrogen.

41. A pharmaceutical composition comprising a compound or a pharmaceutically acceptable salt of claim 38 and a pharmaceutically acceptable carrier.

42. A pharmaceutical composition comprising a compound or a pharmaceutically acceptable salt of claim 39 and a pharmaceutically acceptable carrier.

43. A pharmaceutical composition comprising a compound or a pharmaceutically acceptable salt of claim 40 and a pharmaceutically acceptable carrier.

44. The compound, or a pharmaceutically acceptable salt thereof, of claim 17, wherein $R_1$ is cyclopentyl, optionally substituted with hydroxy, amino, or aminocarbonylamino.

45. The compound, or a pharmaceutically acceptable salt thereof, of claim 18, wherein $R_2$ is chloro, $R_3$ and $R_4$ are hydroxy, $R_5$ is methylaminocarbonyl, and $R_6$ is hydrogen.

46. The compound, or a pharmaceutically acceptable salt thereof, of claim 21, wherein $R_2$ is chloro, $R_3$ and $R_4$ are hydroxy, $R_5$ is methylaminocarbonyl, and $R_6$ is hydrogen.

47. A pharmaceutical composition comprising a compound or a pharmaceutically acceptable salt of claim 44 and a pharmaceutically acceptable carrier.

48. A pharmaceutical composition comprising a compound or a pharmaceutically acceptable salt of claim 45 and a pharmaceutically acceptable carrier.

49. A pharmaceutical composition comprising a compound or a pharmaceutically acceptable salt of claim 46 and a pharmaceutically acceptable carrier.

50. A method for activating an $A_3$ adenosine receptor in a mammal comprising administering to the mammal an effective amount of a compound or pharmaceutically acceptable salt of claim 7.

51. A method for activating an $A_3$ adenosine receptor in a mammal comprising administering to the mammal an effective amount of a compound or pharmaceutically acceptable salt of claim 9.

52. A method for activating an $A_3$ adenosine receptor in a mammal comprising administering to the mammal an effective amount of a compound or pharmaceutically acceptable salt of claim 10.

53. A method for activating an $A_3$ adenosine receptor in a mammal comprising administering to the mammal an effective amount of a compound or pharmaceutically acceptable salt of claim 15.

54. A method for activating an $A_3$ adenosine receptor in a mammal comprising administering to the mammal an effective amount of a compound or pharmaceutically acceptable salt of claim 38.

55. A method of cardioprotecting a patient in need thereof comprising administering to the patient an agonist having affinity for both the $A_1$ and $A_3$ adenosine receptors in an effective amount of a compound or pharmaceutically acceptable salt of claim 44 to activate the $A_1$ and $A_3$ adenosine receptors in the heart of said patient.

56. A method of cardioprotecting a patient in need thereof comprising administering to the patient an agonist having affinity for both the $A_1$ and $A_3$ adenosine receptors in an effective amount of a compound or pharmaceutically acceptable salt of claim 45 to activate the $A_1$ and $A_3$ adenosine receptors in the heart of said patient.

57. A method of cardioprotecting a patient in need thereof comprising administering to the patient an agonist having affinity for both the $A_1$ and $A_3$ adenosine receptors in an effective amount of a compound or pharmaceutically acceptable salt of claim 46 to activate the $A_1$ and $A_3$ adenosine receptors in the heart of said patient.

* * * * *